US007332481B2

(12) United States Patent
Duffy et al.

(10) Patent No.: US 7,332,481 B2
(45) Date of Patent: *Feb. 19, 2008

(54) THROMBOPOIETIN MIMETICS

(75) Inventors: Kevin J. Duffy, Collegeville, PA (US); Connie Erickson-Miller, Collegeville, PA (US); Julian Jenkins, Collegeville, PA (US); Juan Luengo, Collegeville, PA (US); Alan T. Price, Collegeville, PA (US); Antony N. Shaw, Collegeville, PA (US); Sophie Visonneau, San Diego, PA (US); Kenneth Wiggall, Collegeville, PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/620,260

(22) Filed: Jan. 5, 2007

(65) Prior Publication Data
US 2007/0129338 A1 Jun. 7, 2007

Related U.S. Application Data

(63) Continuation of application No. 10/296,688, filed as application No. PCT/US01/16863 on May 24, 2001, now Pat. No. 7,160,870.

(60) Provisional application No. 60/228,929, filed on Aug. 30, 2000, provisional application No. 60/207,084, filed on May 25, 2000.

(51) Int. Cl.
*A61K 31/4152* (2006.01)
*A61K 31/655* (2006.01)

(52) U.S. Cl. ............... 514/150; 514/256; 514/312; 514/341; 514/365; 514/369; 514/381; 514/404

(58) Field of Classification Search ............ 514/150, 514/256, 312, 341, 365, 369, 381, 404
See application file for complete search history.

(56) References Cited

U.S. PATENT DOCUMENTS

| 851,444 | A | 4/1907 | Shulthess |
| 2,809,963 | A | 10/1957 | Hanhart .................. 534/665 |
| 2,950,273 | A | 8/1960 | Pelz |
| 3,366,619 | A | 1/1968 | DeLucia |
| 4,435,417 | A | 3/1984 | Toja et al. |
| 4,510,149 | A | 4/1985 | Cozzi et al. |
| 4,686,285 | A | 8/1987 | Pedrazzi .................. 534/606 |
| 4,880,788 | A | 11/1989 | Moake et al. |
| 4,948,900 | A | 8/1990 | Iijima et al. |
| 5,326,776 | A | 7/1994 | Winn et al. |
| 5,482,546 | A | 1/1996 | Eida |
| 5,532,202 | A | 7/1996 | Yoshida |
| 5,622,818 | A | 4/1997 | Kapp et al. |
| 5,669,967 | A | 9/1997 | Hays |
| 5,746,821 | A | 5/1998 | Hays |
| 5,760,038 | A | 6/1998 | Murugesan et al. |
| 5,932,546 | A | 8/1999 | Barrett et al. |
| 6,214,813 | B1 | 4/2001 | Zhang et al. |
| 6,238,442 | B1 | 5/2001 | Schumacher et al. |
| 6,248,871 | B1 | 6/2001 | Ebenezer et al. |
| 6,280,959 | B1 | 8/2001 | Gleason et al. |
| 6,436,915 | B1 | 8/2002 | Zhang et al. |
| 6,552,008 | B1 * | 4/2003 | Duffy et al. ............. 514/150 |
| 6,608,077 | B2 | 8/2003 | Widdowson et al. |
| 6,642,265 | B1 * | 11/2003 | Luengo et al. ........... 514/407 |
| 7,160,870 | B2 | 1/2007 | Duffy et al. |
| 2003/0060453 | A1 | 3/2003 | Zhang et al. |
| 2004/0063764 | A1 | 4/2004 | Takemoto et al. |
| 2004/0082626 | A1 | 4/2004 | Takemoto et al. |
| 2005/0054643 | A1 | 3/2005 | South et al. |
| 2005/0234020 | A1 * | 10/2005 | Heerding .................. 514/79 |
| 2006/0116417 | A1 * | 6/2006 | Chen et al. ............... 514/418 |
| 2007/0072922 | A1 * | 3/2007 | Brook et al. ............. 514/381 |
| 2007/0105824 | A1 * | 5/2007 | Erickson-Miller et al. .. 514/150 |
| 2007/0129539 | A1 * | 6/2007 | Zhi et al. ................. 534/792 |

FOREIGN PATENT DOCUMENTS

| DE | 193350 | 11/1904 |
| DE | 193350 | 12/1907 |
| DE | 1046220 | 12/1958 |
| EP | 0 638 617 | 8/1994 |
| EP | 1 207 155 | 7/2000 |
| EP | 1 253 142 | 1/2001 |
| EP | 1 104 674 | 6/2001 |
| GB | 826207 | 7/1956 |

(Continued)

OTHER PUBLICATIONS

Nagarajan, et al. Proc. Indian Acad. Sci., 1977, vol. 86A, No. 1, pp. 25-39.

(Continued)

*Primary Examiner*—Fiona T Powers
(74) *Attorney, Agent, or Firm*—Wayne J. Dustman; Stephen Venetianer; Charles M. Kinzig

(57) ABSTRACT

Invented are non-peptide TPO mimetics. Also invented are novel processes and intermediates used in the preparation of the presently invented compounds. Also invented is a method of treating thrombocytopenia, in a mammal, including a human, in need thereof which comprises administering to such mammal an effective amount of a selected hydroxy-1-azobenzene derivative.

26 Claims, No Drawings

FOREIGN PATENT DOCUMENTS

| | | |
|---|---|---|
| GB | 779 880 | 7/1957 |
| JP | 2002-371213 | 12/2002 |
| WO | WO 93/17681 | 9/1993 |
| WO | WO 94/26709 | 11/1994 |
| WO | WO 96/40750 | 12/1996 |
| WO | WO 98/46606 | 10/1998 |
| WO | WO 99/11262 | 3/1999 |
| WO | WO 99/15500 | 4/1999 |
| WO | WO 00/35446 | 6/2000 |
| WO | WO 01/77080 | 1/2001 |
| WO | WO 01/07423 | 2/2001 |
| WO | WO 01/17349 | 3/2001 |
| WO | WO 01/21180 | 3/2001 |
| WO | WO 01/34585 | 5/2001 |
| WO | WO 02/59099 | 1/2002 |
| WO | WO 02/59100 | 1/2002 |
| WO | WO 02/49413 | 6/2002 |
| WO | WO 02/057300 | 7/2002 |
| WO | WO 02/085343 | 10/2002 |
| WO | WO 03/045379 | 6/2003 |
| WO | WO03/074550 | 9/2003 |
| WO | WO03/098992 | 12/2003 |
| WO | WO 03/103686 | 12/2003 |
| WO | WO 2004/054515 | 7/2004 |
| WO | WO 2004/096154 | 11/2004 |
| WO | WO 2005/041867 | 5/2005 |

OTHER PUBLICATIONS

USPTO Office action dated Feb. 22, 2006, (6 pages).
Response to US OA dated Aug. 7, 2006, (15 pages).
Yamazaki, et al., Database HCAPLUS, AN 1995: Abstract, 196968.
A. Esteve, Ann. Pharm. Franc., 1950, vol. 8, No. 9-10, pp. 594-604.
Morris, et al., Anti-Cancer Drugs, 1997, vol. 8, No. 8, pp. 746-755.
Duffy, et al., J. Med. Chem., 2001, vol. 44, No. 22, Abstract No. XP002197261.
Bartley, et al., Cell, 1994, vol. 77, pp. 1117-1124.
Olszewski, et al., Database CAPLUS on STN, 1995, Chem. Abstracts, No. 122:81695.
Olszewski, et al., J. Org. Chem., 1994, vol. 59, pp. 4285-4296.
Lamb, et al., Nucleic Acids Research, 1995, vol. 23, No. 16, pp. 3283-3289.
Seidel, et al., Proc. Natl. Acad. Sci. USA, Mar. 1995, vol. 92, pp. 3041-3045.
Berkhout, et al., J. of Biological Chemistry, Jun. 1997, vol. 272, No. 26, pp. 16404-16413.
Vermeulen, et al., Blood, 1998, vol. 92, No. 3, pp. 894-900.
Hasegawa, et al., Int. J. Immunopharmac, 1996, vol. 18, No. 2, pp. 103-112.
Kumamoto, et al., British Journal of Haematology, 1999, vol. 105, pp. 1025-1033.
Shiotsu, et al., Experimental Hematology, 1998, vol. 26, pp. 1195-1201.
Komatsu, et al., Blood, 1996, vol. 87, No. 11, pp. 4552-4560.
Uguccioni, et al., J. Exp. Med., 1996, vol. 183, pp. 2397-2384.
Taylor, et al., J. Org. Chem., 1987, vol. 52, pp. 4107-4110.
Kuter, et al., Seminars in Hematology, Apr. 2000, vol. 37, No. 2, pp. 41-49.
Ballestrero, et al., Oncology, 2000, vol. 59, pp. 7-13.
Sawai, et al., Journal of Leukocyte Biology, Jul. 2000, vol. 68, pp. 137-143.
Vigon, et al., Proc. Natl. Acad. Sci. USA, Jun. 1992, vol. 89, pp. 5640-5644.
Laurenz, et al., Comp. Biochem Physiol., 1997, vol. 116A, No. 4, pp. 369-377.
Metcalf, et al., Nature, Jun. 16, 1994, vol. 369, pp. 519-520.
Bussel, et al., Seminars in Hematology, 2000, vol. 37, pp. 1-49 (Table of Contents).
McDonald, et al., Am. J. of Pediatric Hematology/Oncology, 1992, vol. 14, No. 1, pp. 8-21.
Souyri, et al., Cell, 1990, vol. 63, pp. 1137-1147.
Bazan, et al., Pro. Natl. Acad. Sci. USA, Sep. 1990, vol. 87, pp. 6934-6938.
Sauvage, et al., Nature, Jun. 16, 1994, vol. 369, pp. 533-538.
Wendling, et al., Nature, Jun. 16, 1994, vol. 369, pp. 571-574.
Kaushansky, et al., Nature, Jun. 16, 1994, vol. 369, pp. 568-571.
King, et al., The Journal of Immunology, 2000, pp. 3774-3782.
Kikuta, et al., Experimental Hematology, 2000, vol. 28, pp. 311-317.
Somlo, et al., Blood, May 1, 1992, vol. 93, No. 9, pp. 2798-2806.
Kirley-Neumann, et al., Cytokines, Cellular & Molecular Therapy, 2000, vol. 6, pp. 47-56.
Egger, et al., Bone Marrow Transplant, 1998, vol. 22, pp. 34-35.
Gaudron, et al., Stem Cells, 1999, vol. 17, pp. 100-106.
Fetscher, et al., Current Opinion in Hematology, 2000, vol. 7, pp. 255-260.
Clemons, et al., Breast Cancer Res. Treatment, 1999, vol. 57, pp. 127.
Greene, "Protective Groups in Organic Synthesis", 1981, Table of Contents.
Methia, et al., Blood, 1993, vol. 82, No. 5, pp. 1395-1401.
Yamazaki, et al., Japn. J. Toxicol. Environ. Health, 1994, vol. 94, No. 5, pp. 448-453.
Duffin, et al., J. of the Chem. Soc., 1954, pp. 408-41.
King, et al., Scand. J. of Immunol., 1999, vol. 49, No. 2, pp. 184-192.
Konica Corp. Derwent No. 92-077508/10, 1992.
Mitsubishi Pharma Corp. Derwent No. 2003-845201/78, 2003.
Mitsubishi Pharma Corp. Derwent No. 2003-767492/72, 2003.
Balli, et al., Dyes. Pigm., 1981, vol. 2, No. 2, pp. 93-124.
Balli, et al., Justus Liebigs Ann. Chem., 1966, vol. 699, pp. 133-134.
Dziomko, et al., Chem. Heterocycl. Compd., 1984, vol. 20, No. 2, pp. 196-200.
Duffy, et al., J. Med. Chem., 2001, vol. 44, No. 22, p. 3730-3745.
Kimura, et al., FEBS Letters, 1998, vol. 428, No. 3, pp. 250-254.
Beckert, et al., Monatshefte Fur Chemie, 1989, vol. 120, pp. 1125-1137.
A. Esteve, Ann. Pharm. Franc., 1950, vol. 8, No. 9-10, 594-604.
PCT/US2004/13468 filed Apr. 29, 2004—(WO 04/096154).
PCT/US2004/034944 filed Oct. 21, 2004—(WO 05/041867).
Minssen-Guette, et al., Bulletin De La Societe Chimique De France, 1986, No. 5, pp. 2106-2110.
European Search report dated Dec. 15, 2003.
European office action dated Feb. 2, 2005.
Bussel, et al., Seminars in Hematology, 2000, vol. 37, pp. 1-49 (whole journal). see ids #7.
Balli, et al., Dyes. Pigm., 1981, vol. 2, No. 2, pp. 93-124 (sent original).
Balli, et al., Justus Liebigs Ann. Chem., 1966, vol. 699, pp. 133-144. (sent original).

* cited by examiner

THROMBOPOIETIN MIMETICS

This application is a continuation of U.S. application Ser. No. 10/296,688, filed Jul. 3, 2003, now U.S. Pat. No. 7,160,870 which is a 371 of International Application No. PCT/US01/16863, filed May 24, 2001, which claims the benefit of U.S. Provisional Application No. 60/207,084, filed May 25, 2000 and 60/228,929, filed Aug. 30, 2000.

FIELD OF THE INVENTION

This invention relates to thrombopoietin (TPO) mimetics and their use as promoters of thrombopoiesis and megakaryocytopoiesis.

BACKGROUND OF THE INVENTION

Megakaryocytes are bone marrow-derived cells, which are responsible for producing circulating blood platelets. Although comprising <0.25% of the bone marrow cells in most species, they have >10 times the volume of typical marrow cells. See Kuter et al. *Proc. Natl. Acad. Aci. USA* 91: 11104-11108 (1994). Megakaryocytes undergo a process known as endomitosis whereby they replicate their nuclei but fail to undergo cell division and thereby give rise to polypoid cells. In response to a decreased platelet count, the endomitotic rate increases, higher ploidy megakaryocytes are formed, and the number of megakaryocytes may increase up to 3-fold. See Harker *J. Clin. Invest.* 47: 458-465 (1968). In contrast, in response to an elevated platelet count, the endomitotic rate decreases, lower ploidy megakaryocytes are formed, and the number of megakaryocytes may decrease by 50%.

The exact physiological feedback mechanism by which the mass of circulating platelets regulates the endomitrotic rate and number of bone marrow megakaryocytes is not known. The circulating thrombopoietic factor involved in mediating this feedback loop is now thought to be thrombopoietin (TPO). More specifically, TPO has been shown to be the main humoral regulator in situations involving thrombocytopenia. See, e.g., Metcalf Nature 369:519-520 (1994). TPO has been shown in several studies to increase platelet counts, increase platelet size, and increase isotope incorporation into platelets of recipient animals. Specifically, TPO is thought to affect megakaryocytopoiesis in several ways: (1) it produces increases in megakaryocyte size and number; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow.

Because platelets (thrombocytes) are necessary for blood clotting and when their numbers are very low a patient is at risk of death from catastrophic hemorrhage, TPO has potential useful application in both the diagnosis and the treatment of various hematological disorders, for example, diseases primarily due to platelet defects (see Harker et al. *Blood* 91: 4427-4433 (1998)). Ongoing clinical trials with TPO have indicated that TPO can be administered safely to patients (see Basser et al. *Blood* 89: 3118-3128 (1997); Fanucchi et al. *New Engl. J. Med.* 336: 404-409 (1997)). In addition, recent studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. (See Harker, *Curr. Opin. Hematol.* 6: 127-134 (1999)).

The gene encoding TPO has been cloned and characterized. See Kuter et al., *Proc. Natl. Acad. Sci. USA* 91: 11104-11108 (1994); Barley et al., *Cell* 77: 1117-1124 (1994); Kaushansky et al., *Nature* 369:568-571 (1994); Wendling et al., *Nature* 369: 571-574 (1994); and Sauvage et al., *Nature* 369: 533-538 (1994). Thrombopoietin is a glycoprotein with at least two forms, with apparent molecular masses of 25 kDa and 31 kDa, with a common N-terminal amino acid; sequence. See, Baatout, *Haemostasis* 27: 1-8 (1997); Kaushansky, *New Engl. J. Med.* 339: 746-754 (1998). Thrombopoietin appears to have two distinct regions separated by a potential Arg-Arg cleavage site. The amino-terminal region is highly conserved in man and mouse, and has some homology with erythropoietin and interferon-a and interferon-b. The carboxy-terminal region shows wide species divergence.

The DNA sequences and encoded peptide sequences for human TPO receptor (TPO-R; also known as c-mpl) have been described. (See, Vigon et al. *Proc. Natl. Acad. Sci. USA* 89: 5640-5644 (1992)). TPO-R is a member of the haematopoietin growth factor receptor family, a family characterized by a common structural design of the extracellular domain, including for conserved C residues in the N-terminal portion and a WSXWS motif close to the transmembrane region. (See Bazan *Proc. Natl. Acad. Sci. USA* 87: 6934-6938 (1990)). Evidence that this receptor plays a functional role in hematopoiesis includes observations that its expression if restricted to spleen, bone marrow, or fetal liver in mice (see Souyri et al. *Cell* 63: 1137-1147 (1990)) and to megakaryocytes, platelets, and CD34+ cells in humans (see Methia et al. *Blood* 82: 1395-1401 (1993)). Further evidence for TPO-R as a key regulator of megakaryopoiesis is the fact that exposure of CD34+ cells to synthetic oligonucleotides antisense to TPO-R RNA significantly inhibits the appearance of megakaryocyte colonies without affecting erythroid or myeloid colony formation. Some workers postulate that the receptor functions as a homodimer, similar to the situation with the receptors for G-CSF and erythropoietin. (see Alexander et al. *EMBO J.* 14: 5569-5578 (1995)).

The slow recovery of platelet levels in patients suffering from thrombocytopenia is a serious problem, and has lent urgency to the search for a blood growth factor agonist able to accelerate platelet regeneration (see Kuter, *Seminars in Hematology,* 37: Supp 4: 41-49 (2000)).

It would be desirable to provide compounds which allow for the treatment of thrombocytopenia by acting as a TPO mimetic.

As disclosed herein it has unexpectedly been discovered that certain hydroxy-1-azo-benzene derivatives are effective as agonists of the TPO receptor, they are potent TPO mimetics.

SUMMARY OF THE INVENTION

This invention relates to compounds of Formula (I):

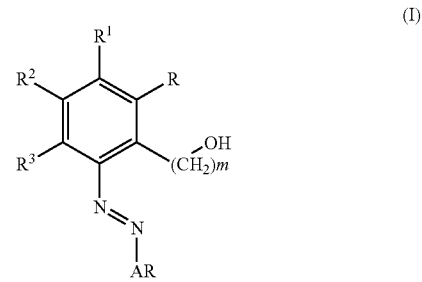

wherein:

R, $R^1$, $R^2$ and $R^3$ are each independently selected from hydrogen, $C_{1-6}$alkyl, $-(CH_2)_pOR^4$, $-C(O)OR^4$, formyl, nitro, cyano, halogen, aryl, substituted aryl, substituted alkyl, —S(O)$_n$R$^4$, cycloalkyl, —NR$^5$R$^6$, protected OH, —CONR$^5$R$^6$, phosphonic acid, sulfonic acid, phosphinic acid, —SO$_2$NR$^5$R$^6$, and a heterocyclic methylene substituent as represented by Formula (III),

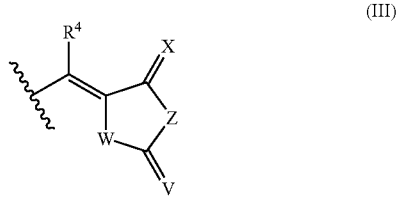

(III)

where, p is 0-6, n is 0-2,

V, W, X and Z are each independently selected from O, S and NR$^{16}$, where R$^{16}$ is selected from: hydrogen, alkyl, cycloalkyl, C$_1$-C$_{12}$aryl, substituted alkyl, substituted cycloalkyl and substituted C$_1$-C$_{12}$aryl, R$^4$ is selected from: hydrogen, alkyl, cycloalkyl, C$_1$-C$_{12}$aryl, substituted alkyl, substituted cycloalkyl and substituted C$_1$-C$_{12}$aryl, and R$^5$ and R$^6$ are each independently selected from hydrogen, alkyl, substituted alkyl, C$_{3-6}$cycloalkyl, and aryl, or R$^5$ and R$^6$ taken together with the nitrogen to which they are attached represent a 5 to 6 member saturated ring containing up to one other heteroatom selected from oxygen and nitrogen;

m is 0-6; and

AR is a cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, —C(O)OR$^4$, —C(O)NR$^{10}$R$^{11}$, —S(O)$_2$NR$^{10}$R$^{11}$, —S(O)$^r$R$^4$ and protected —OH, where n is 0-2, R$^4$ is hydrogen, alkyl, cycloalkyl, C$_1$-C$_{12}$aryl, substituted alkyl, substituted cycloalkyl and substituted C$_1$-C$_{12}$aryl, and R$^{10}$ and R$^{11}$ are independently hydrogen, cycloalkyl, C$_1$-C$_{12}$aryl, substituted cycloalkyl, substituted C$_1$-C$_{12}$aryl, alkyl or alkyl substituted with one or more substituents selected from the group consisting of: alkoxy, acyloxy, aryloxy, amino, N-acylamino, oxo, hydroxy, —C(O)OR$^4$, —S(O)$_n$R$^4$, —C(O)NR$^4$R$^4$, —S(O)$_2$NR$^4$R$^4$, nitro, cyano, cycloalkyl, substituted cycloalkyl, halogen, aryl, substituted aryl and protected —OH, or R$^{10}$ and R$^{11}$ taken together with the nitrogen to which they are attached represent a 5 to 6 member saturated ring containing up to one other heteroatom selected from oxygen and nitrogen, where R$^4$ is as described above and n is 0-2;

and pharmaceutically acceptable salts, hydrates, solvates and esters thereof;

provided that at least one of R, R$^1$, R$^2$ and R$^3$ is a substituted aryl group or a heterocyclic methylene substituent as represented in Formula (III).

This invention relates to a method of treating thrombocytopenia, which comprises administering to a subject in need thereof an effective amount of a TPO mimetic compound of Formula (I).

The present invention also relates to the discovery that the compounds of Formula (I) are active as agonists of the TPO receptor.

In a further aspect of the invention there is provided novel processes and novel intermediates useful in preparing the presently invented TPO mimetic compounds.

Included in the present invention are pharmaceutical compositions comprising a pharmaceutical carrier and compounds useful in the methods of the invention.

Also included in the present invention are methods of co-administering the presently invented TPO mimetic compounds with further active ingredients.

DETAILED DESCRIPTION OF THE INVENTION

This invention relates to compounds of Formula (I) as described above.

Included among the presently invented compounds of Formula (I) are those having Formula (V):

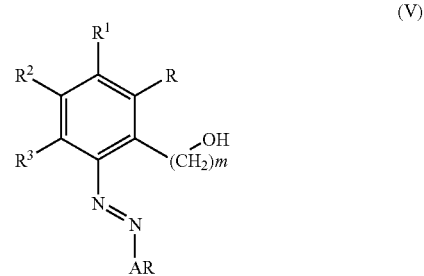

(V)

wherein:

R, R$^1$, R$^2$ and R$^3$ are each independently selected from hydrogen, C$_{1-6}$alkyl, C$_{1-6}$alkoxy, —(CH$_2$)$_p$OR$^4$, —C(O)OR$^4$, formyl, nitro, cyano, halogen, aryl, substituted aryl, substituted alkyl, —S(O)$_n$R$^4$, cycloalkyl, —NR$^5$R$^6$, protected —OH, —CONR$^5$R$^6$, phosphonic acid, sulfonic acid, phosphinic acid and —SO$_2$NR$^5$R$^6$, where, p is 0-6, n is 0-2, R$^4$ is selected from: hydrogen, alkyl, cycloalkyl, C$_1$-C$_{12}$aryl, substituted alkyl, substituted cycloalkyl and substituted C$_1$-C$_{12}$aryl, and R$^5$ and R$^6$ are each independently selected from hydrogen, alkyl, substituted alkyl, C$_{3-6}$cycloalkyl, and aryl, or R$^5$ and R$^6$ taken together with the nitrogen to which they are attached represent a 5 to 6 member saturated ring containing up to one other heteroatom selected from oxygen and nitrogen;

m is 0-6; and

AR is a cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, —C(O)OR$^4$, —C(O)NR$^{10}$R$^{11}$, —S(O)$_2$NR$^{10}$R$^{11}$, —S(O)$_n$R$^4$ and protected —OH, where n is 0-2, R$^4$ is hydrogen, alkyl, cycloalkyl, C$_1$-C$_{12}$aryl, substituted alkyl, substituted cycloalkyl and substituted C$_1$-C$_{12}$aryl; and R$^{10}$ and R$^{11}$ are independently hydrogen, cycloalkyl, C$_1$-C$_{12}$aryl, substituted cycloalkyl, substituted C$_1$-C$_{12}$aryl, alkyl or alkyl substituted with one or more substituents selected from the group consisting of: alkoxy, acyloxy, aryloxy, amino, N-acylamino, oxo, hydroxy, —C(O)OR$^4$, —S(O)$_n$R$^4$, —C(O)NR$^4$R$^4$, —S(O)$_2$NR$^4$R$^4$, nitro, cyano, cycloalkyl, substituted cycloalkyl, halogen, aryl, substituted aryl and protected —OH, or R$^{10}$ and R$^{11}$ taken together with the nitrogen to which they are attached represent a 5 to 6 member saturated ring containing up to one other heteroatom selected from oxygen and nitrogen, where R$^4$ is as described above and n is 0-2;

and pharmaceutically acceptable salts, hydrates, solvates and esters thereof;

provided that at least one of R, R$^1$, R$^2$ and R$^3$ is a substituted aryl group.

Preferred among the presently invented compounds of Formula (I) are those having Formula (II):

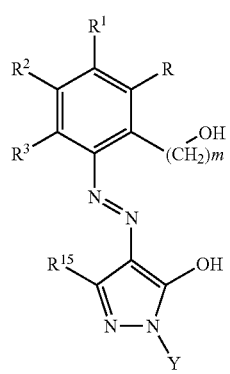

(II)

wherein:

R, R$^1$, R$^2$ and R$^3$ are each independently selected from hydrogen, C$_{1-6}$alkyl, —(CH$_2$)$_p$OR$^4$, —C(O)OR$^4$, formyl, nitro, cyano, halogen, aryl, substituted aryl, substituted alkyl, —S(O)$_n$R$^4$, cycloalkyl, —NR$^5$R$^6$, protected —OH, —CONR$^5$R$^6$, phosphonic acid, sulfonic acid, phosphinic acid, —SO$_2$NR$^5$R$^6$, and a heterocyclic methylene substituent as represented by Formula (III),

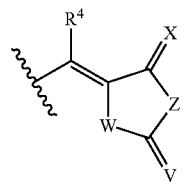

(III)

where
p is 0-6,
n is 0-2,
V, W, X and Z are each independently selected from O, S, and NR$^{16}$, where R$^{16}$ is selected from: hydrogen, alkyl, cycloalkyl, C$_1$-C$_{12}$aryl, substituted alkyl, substituted cycloalkyl and substituted C$_1$-C$_{12}$aryl,
R$^4$ is hydrogen, alkyl, cycloalkyl, C$_1$-C$_{12}$aryl, substituted alkyl, substituted cycloalkyl and substituted C$_1$-C$_{12}$aryl, and
R$^5$ and R$^6$ are each independently selected from hydrogen, alkyl, substituted alkyl, C$_{3-6}$cycloalkyl, and aryl, or R$^5$ and R$^6$ taken together with the nitrogen to which they are attached represent a 5 to 6 member saturated ring containing up to one other heteroatom selected from oxygen and nitrogen;
R$^{15}$ is selected from the group consisting of alkyl, C$_1$-C$_{12}$aryl, hydroxy, alkoxy, substituted alkyl, substituted C$_1$-C$_{12}$aryl and halogen;
m is 0-6; and
Y is selected from alkyl, substituted alkyl and a cyclic or polycyclic aromatic ring containing from 3 to 14 carbon atoms and optionally containing from one to three heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, C$_1$-C$_{12}$aryl, substituted cycloalkyl, substituted C$_1$-C$_{12}$aryl, hydroxy, aryloxy, alkoxy, cycloalkyl, nitro, cyano, halogen and protected —OH;

and pharmaceutically acceptable salts, hydrates, solvates and esters thereof;

provided that at least one of R, R$^1$, R$^2$ and R$^3$ is a substituted aryl group or a heterocyclic methylene substituent as represented in Formula (III).

Included among the presently invented compounds of Formula (II) are compounds in which R$^{15}$ is not alkoxy.

Included among the presently invented compounds of Formula (II) are those having Formula (VI):

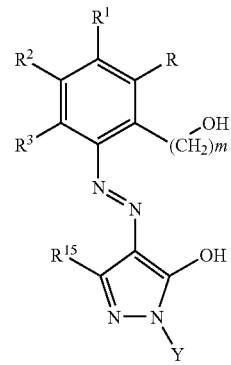

(VI)

wherein:
R, $R^1$, $R^2$ and $R^3$ are each independently selected from hydrogen, $C_{1-6}$alkyl, $C_{1-6}$alkoxy, —$(CH_2)_pOR^4$, —$C(O)OR^4$, formyl, nitro, cyano, halogen, aryl, substituted aryl, substituted alkyl, —$S(O)_nR^4$, cycloalkyl, —$NR^5R^6$, protected OH, —$CONR^5R^6$, phosphonic acid, sulfonic acid, phosphinic acid and —$SO_2NR^5R^6$, where
p is 0-6,
n is 0-2,
$R^4$ is hydrogen, alkyl, cycloalkyl, $C_1$-$C_{12}$aryl, substituted alkyl, substituted cycloalkyl and substituted $C_1$-$C_{12}$aryl, and
$R^5$ and $R^6$ are each independently selected from hydrogen, alkyl, substituted alkyl, $C_{3-6}$cycloalkyl, and aryl,
or $R^5$ and $R^6$ taken together with the nitrogen to which they are attached represent a 5 to 6 member saturated ring containing up to one other heteroatom selected from oxygen and nitrogen;
$R^{15}$ is selected from the group consisting of alkyl, $C_1$-$C_{12}$aryl, hydroxy, alkoxy, substituted alkyl, substituted $C_1$-$C_{12}$aryl and halogen;
m is 0-6; and
Y is selected from alkyl, substituted alkyl and a cyclic or polycyclic aromatic ring containing from 3 to 14 carbon atoms and optionally containing from one to three heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, $C_1$-$C_{12}$aryl, substituted cycloalkyl, substituted $C_1$-$C_{12}$aryl, hydroxy, aryloxy, alkoxy, cycloalkyl, nitro, cyano, halogen and protected OH;
and pharmaceutically acceptable salts, hydrates, solvates and esters thereof;
provided that at least one of R, $R^1$, $R^2$ and $R^3$ is a substituted aryl group.

Also included among the presently invented compounds of Formula (II) are compounds of Formula (VI) in which $R^{15}$ is not alkoxy.

Preferred among the presently invented Formula VI compounds are those in which, either:
R is a substituted aryl; and $R^1$ is hydrogen; or:
R is hydrogen; and $R^1$ is a substituted aryl; and in either case:
$R^2$ and $R^3$ are each independently selected from hydrogen, $C_{1-6}$alkyl, $C_{1-6}$alkoxy, nitro, cyano, halogen, aryl, substituted aryl, substituted alkyl, cycloalkyl, phosphonic acid, phosphinic acid and sulfonic acid;
$R^{15}$ is selected from the group consisting of alkyl, substituted alkyl, $C_1$-$C_{12}$aryl, alkoxy and halogen;
m is 0-4; and
Y is selected from,
phenyl, pyridinyl and pyrimidinyl, where the phenyl, pyridinyl and pyrimidinyl are optionally substituted with from one to three substituents selected from the group consisting of: alkyl, substituted alkyl, $C_1$-$C_{12}$aryl, substituted $C_1$-$C_{12}$aryl, alkoxy and halogen;
and pharmaceutically acceptable salts, hydrates, solvates and esters thereof.

Particularly preferred among the presently invented Formula VI compounds are those in which, R is a substituted $C_1$-$C_{12}$aryl;
and
$R^1$ is hydrogen;
$R^2$ and $R^3$ are each independently selected from hydrogen, $C_{1-6}$alkyl, $C_{1-6}$alkoxy, nitro, cyano, halogen, substituted alkyl and cycloalkyl;
$R^{15}$ is selected from the group consisting of alkyl, substituted alkyl, $C_1$-$C_{12}$aryl, alkoxy and halogen;
m is 0-2; and
Y is selected from,
phenyl, pyridinyl and pyrimidinyl, where the phenyl, pyridinyl and pyrimidinyl are optionally substituted with from one to three substituents selected from the group consisting of: alkyl, substituted alkyl, $C_1$-$C_{12}$aryl, substituted $C_1$-$C_{12}$aryl, alkoxy and halogen;
and pharmaceutically acceptable salts, hydrates, solvates and esters thereof.

The most preferred among the presently invented Formula VI compounds are those in which,
R is a substituted phenyl or pyridinyl ring; and
$R^1$ is hydrogen;
$R^2$ and $R^3$ are each independently selected from hydrogen, $C_{1-6}$alkyl, substituted alkyl and halogen;
$R^{15}$ is selected from the group consisting of $C_{1-4}$alkyl, $C_{1-4}$alkoxy, $C_1$-$C_{12}$aryl and halogen;
m is 0; and
Y is selected from,
phenyl, pyridinyl and pyrimidinyl, where the phenyl, pyridinyl and pyrimidinyl is optionally substituted with from one to three substituents selected from the group consisting of: alkyl, substituted alkyl, $C_1$-$C_{12}$aryl, substituted $C_1$-$C_{12}$aryl, alkoxy and halogen;
and pharmaceutically acceptable salts, hydrates, solvates and esters thereof.

Preferred among the presently invented compounds are:
4'-{N'-[1-(3,4-Dimethylphenyl)-3-methyl-5-oxo-1,5-dihydropyrazol-4-ylidene]hydrazino}-3'-hydroxybiphenyl-4-carboxylic acid;
4'-{N'-[1-(3,4-Dimethylphenyl)-3-methyl-5-oxo-1,5-dihydropyrazol-4-ylidene]hydrazino}-3'-hydroxybiphenyl-3-carboxylic acid;
3'-{N'-[1-(3,4-Dimethylphenyl)-3-methyl-5-oxo-1,5-dihydropyrazol-4-ylidene]hydrazino}-2'-hydroxybiphenyl-3-carboxylic acid;
3'-{N'-[1-(4-tert-Butylphenyl)-3-methyl-5-oxo-1,5-dihydropyrazol-4-ylidene]hydrazino}-2'-hydroxybiphenyl-3-carboxylic acid;
2-Aza-3'-{N'-[1-(4-tert-butylphenyl)-3-methyl-5-oxo-1,5-dihydropyrazol-4-ylidene]hydrazino}-5'-chloro-2'-hydroxybiphenyl-3-carboxylic acid;
2-Aza-3'-{N'-[1-(4-tert-butylphenyl)-3-methyl-5-oxo-1,5-dihydropyrazol-4-ylidene]hydrazino}-2'-hydroxybiphenyl-3-carboxylic acid;
3-Aza-3'-{N'-[1-(4-tert-butylphenyl)-3-methyl-5-oxo-1,5-dihydropyrazol-4-ylidene]hydrazino}-2'-hydroxybiphenyl-5-carboxylic acid;
2-Aza-5'-chloro-3'-{N'-[1-(3,4-dimethylphenyl)-3-methyl-5-oxo-1,5-dihydropyrazol-4-ylidene]hydrazino}-2'-hydroxybiphenyl-3-carboxylic acid;
2-Aza-3'-{N'-[1-(4-tert-butylphenyl)-3-methyl-5-oxo-1,5-dihydropyrazol-4-ylidene]hydrazino}-2'-hydroxy-5'-methylbiphenyl-3-carboxylic acid;
2-Aza-3'-{N'-[1-(3,4-dimethylphenyl)-3-methyl-5-oxo-1,5-dihydropyrazol-4-ylidene]hydrazino}-2'-hydroxy-5'-methylbiphenyl-3-carboxylic acid;

3'-{N'-[1-(4-tert-Butylphenyl)-3-methyl-5-oxo-1,5-dihydropyrazol-4-ylidene]hydrazino}-2'-hydroxy-5'-methylbiphenyl-3-carboxylic acid;

3-{N'-[1-(3,4-dimethylphenyl)-3-methyl-5-oxo-1,5-dihydropyrazol-4-ylidene]hydrazino}-2-hydroxy-3'-tetrazol-5-ylbiphenyl;

3'-{N'-[1-(3,4-dimethylphenyl)-3-methyl-5-oxo-1,5-dihydropyrazol-4-ylidene]hydrazino}-5'-fluoro-2'-hydroxybiphenyl-3-carboxylic acid;

7-({N'-[1-(3,4-dimethylphenyl)-3-methyl-5-oxo-1,5-dihydropyrazol-4-ylidene]hydrazino}-2-hydroxyphenyl)quinolin-4[1H]-one-3-carboxylic acid;

7-({N'-[1-(4-tert-butylphenyl)-3-methyl-5-oxo-1,5-dihydropyrazol-4-ylidene]hydrazino}-2-hydroxyphenyl)quinolin-4[1H]-one-3-carboxylic acid;

3-Aza-3'-{N'-[1-(3,4-dimethylphenyl)-3-methyl-5-oxo-1,5-dihydropyrazol-4-ylidene]hydrazino}-2'-hydroxybiphenyl-5-carboxylic acid;

3-Aza-3'-(N'-[1-{3-methyl-[4-(1-methylethyl)phenyl]-5-oxo-1,5-dihydropyrazol-4-ylidene}hydrazino)-2'-hydroxybiphenyl-5-carboxylic acid;

3-Aza-3'-{N'-[1-(4-tertbutylphenyl-3-methyl-5-oxo-1,5-dihydropyrazol-4-ylidene]hydrazino}-2'-hydroxybiphenyl-5-carboxylic acid;

5'-Chloro-3'-{N'-[1-(3,4-dimethylphenyl)-3-methyl-5-oxo-1,5-dihydropyrazol-4-ylidene]hydrazino}-2'-hydroxybiphenyl-3-carboxylic acid;

3'-{N'-[1-(3,4-Dimethylphenyl)-3,5-dioxo-1,5-dihydropyrazol-4-ylidene]hydrazino}-2'-hydroxybiphenyl-3-carboxylic acid;

3'-{N'-[1-(2-Ethoxy-2-oxoethyl)-3-methyl-5-oxo-1,5-dihydropyrazol-4-ylidene]hydrazino}-2'-hydroxybiphenyl-3-carboxylic acid;

3-{N'-[1-(3,4-dimethylphenyl)-3-methyl-5-oxo-1,5-dihydropyrazol-4-ylidene]hydrazino}-2-hydroxy-4'-(tetrazol-5-yl)biphenyl;

3'-(N'-{1-[2-(N-tert-butyl)amino-2-oxoethyl]-3-methyl-5-oxo-1,5-dihydropyrazol-4-ylidene}hydrazino)-2'-hydroxybiphenyl-3-carboxylic acid;

3'-{N'-[3-Chloro-1-(3,4-dimethylphenyl)-5-oxo-1,5-dihydropyrazol-4-ylidene]hydrazino}-2'-hydroxybiphenyl-3-carboxylic acid;

5-chloro-3-{N'-[1-(3,4-dimethylphenyl)-3-methyl-5-oxo-1,5-dihydropyrazol-4-ylidene]hydrazino}-2-hydroxy-4'-(tetrazol-5-yl)biphenyl;

3'-{N'-[1-(3,4-Dimethylphenyl)-3-methyl-5-oxo-1,5-dihydropyrazol-4-ylidene]hydrazino}-2'-hydroxybiphenyl-3,5-dicarboxylic acid;

3-Aza-3'-{N'-[1-(3,4-dimethylphenyl)-3-methyl-5-oxo-1,5-dihydropyrazol-4-ylidene]hydrazino}-2'-hydroxy-5'-methylbiphenyl-5-carboxylic acid;

3'-{N'-[1-(3,4-Dimethylphenyl)-3-methyl-5-oxo-1,5-dihydropyrazol-4-ylidene]hydrazino}-2'-hydroxybiphenyl-4-carboxylic acid;

3'-{N'-[1-(3,4-Dimethylphenyl)-3-methoxy-5-oxo-1,5-dihydropyrazol-4-ylidene]hydrazino}-2'-hydroxybiphenyl-3-carboxylic acid;

3'-{N'-[1-(4-methoxyphenyl)-3-methyl-5-oxo-1,5-dihydropyrazol-4-ylidene]hydrazino}-2'-hydroxybiphenyl-3-carboxylic acid;

(3-{N'-[1-(3,4-dimethylphenyl)-3-methyl-5-oxo-1,5-dihydropyrazol-4-ylidene]hydrazino}-2-hydroxy-3'-biphenyl)-1,1,1,-trifluoromethanesulfonamide;

3'-{N'-[1-(3,4-Dichlorophenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(3-trifluoromethylphenyl)-1,5-dihydropyrazol-4-ylidene]hydrazino}-2'-hydroxybiphenyl-3-carboxylic acid;

8-{N'-[1-(3,4-dimethylphenyl)-3-methyl-5-oxo-1,5-dihydropyrazol-4-ylidene]hydrazino}quinolin-4[1H]-one-3-carboxylic acid;

3'-{N'-[3-methyl-5-oxo-1-(4-trifluoromethylphenyl)-1,5-dihydropyrazol-4-ylidene]hydrazino}-2'-hydroxybiphenyl-3-carboxylic acid;

3'-{N'-[3-methyl-5-oxo-1-(4-N-methylcarboxamidophenyl)-1,5-dihydropyrazol-4-ylidene]hydrazino}-2'-hydroxybiphenyl-3-carboxylic acid;

N-[1-(3'-{N'-[1-(3,4-dimethylphenyl)-3-methyl-5-oxo-1,5-dihydropyrazol-4-ylidene]hydrazino}-2'-hydroxybiphenyl-3-yl)methanoyl]methanesulfonamide;

3'-{N'-[3-methyl-5-oxo-1-phenyl-1,5-dihydropyrazol-4-ylidene]hydrazino}-2'-hydroxybiphenyl-3-carboxylic acid;

3'-{N'-[3-methyl-1-(4-methylphenyl)-5-oxo-1,5-dihydropyrazol-4-ylidene]hydrazino}-2'-hydroxybiphenyl-3-carboxylic acid;

3'-{N'-[1-(4-chlorophenyl)-3-methyl-5-oxo-1,5-dihydropyrazol-4-ylidene]hydrazino}-2'-hydroxybiphenyl-3-carboxylic acid;

3'-{N'-[1-(4-fluorophenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(4-trifluoromethoxyphenyl)-1,5-dihydropyrazol-4-ylidene]hydrazino}-2'-hydroxybiphenyl-3-carboxylic acid;

3'-{N'-[1-(3,4-dimethylphenyl)-3-ethoxy-5-oxo-1,5-dihydropyrazol-4-ylidene]hydrazino}-2'-hydroxybiphenyl-3-carboxylic acid;

3'-{N'-[1-(3,4-dimethylphenyl)-3-(1-methylethoxy)-5-oxo-1,5-dihydropyrazol-4-ylidene]hydrazino}-2'-hydroxybiphenyl-3-carboxylic acid;

3'-{N'-[3-tert-butyl-1-(3,4-dimethylphenyl)-5-oxo-1,5-dihydropyrazol-4-ylidene]hydrazino}-2'-hydroxybiphenyl-3-carboxylic acid;

3'-{N'-[3-methyl-1-(4-methyl-2,3,5,6-tetrafluorophenyl)-5-oxo-1,5-dihydropyrazol-4-ylidene]hydrazino}-2'-hydroxybiphenyl-3-carboxylic acid;

3'-{N'-[1-(4-fluoro-3-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-phenyl-5-oxo-1,5-dihydropyrazol-4-ylidene]hydrazino}-2'-hydroxybiphenyl-3-carboxylic acid;

3-{N'-[1-(3,4-dimethylphenyl)-5-oxo-3-phenyl-1,5-dihydropyrazol-4-ylidene]hydrazino}-2-hydroxy-3'-tetrazol-5-ylbiphenyl;

3-{N'-[1-(3,4-dimethylphenyl)-3-methoxy-5-oxo-1,5-dihydropyrazol-4-ylidene]hydrazino}-2-hydroxy-3'-tetrazol-5-ylbiphenyl;

3-{N'-[1-(3,4-dimethylphenyl)-3-ethoxy-5-oxo-1,5-dihydropyrazol-4-ylidene]hydrazino}-2-hydroxy-3'-tetrazol-5-ylbiphenyl;

3-{N'-[1-(3,4-dimethylphenyl)-3-(1-methylethoxy)-5-oxo-1,5-dihydropyrazol-4-ylidene]hydrazino}-2-hydroxy-3'-tetrazol-5-ylbiphenyl;

3-{N'-[1-(4-fluorophenyl)-3-methyl-5-oxo-1,5-dihydropyrazol-4-ylidene]hydrazino}-2-hydroxy-3'-tetrazol-5-ylbiphenyl;

3-{N'-[1-(4-fluoro-3-methylphenyl)-3-methyl-5-oxo-1,5-dihydropyrazol-4-ylidene]hydrazino}-2-hydroxy-3'-tetrazol-5-ylbiphenyl;

3-{N'-[3-methyl-5-oxo-1-(4-trifluoromethylphenyl)-1,5-dihydropyrazol-4-ylidene]hydrazino}-2-hydroxy-3'-tetrazol-5-ylbiphenyl;

3'-{N'-[1-(3,4-dimethylphenyl)-3-(pyridin-4-yl-5-oxo-1,5-dihydropyrazol-4-ylidene]hydrazino}-2'-hydroxybiphenyl-3-carboxylic acid;

3-{N'-[1-(3,4-dimethylphenyl)-3-pyridin-4-yl-5-oxo-1,5-dihydropyrazol-4-ylidene]hydrazino}-2-hydroxy-3'-tetrazol-5-ylbiphenyl;

3-{N'-[1-(3,4-dimethylphenyl)-3-pyridin-2-yl-5-oxo-1,5-dihydropyrazol-4-ylidene]hydrazino}-2-hydroxy-3'-tetrazol-5-ylbiphenyl;

3'-{N'-[1-(3,4-dimethylphenyl)-3-(pyridin-2-yl-5-oxo-1,5-dihydropyrazol-4-ylidene]hydrazino}-2'-hydroxybiphenyl-3-carboxylic acid;

3-{N'-[1-(3-fluoro-4-methylphenyl)-3-methyl-5-oxo-1,5-dihydropyrazol-4-ylidene]hydrazino}-2-hydroxy-3'-tetrazol-5-ylbiphenyl;

3'-{N'-[1-(3-fluoro-4-methylphenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(4-trifluoromethylpyrimidin-2-yl)-1,5-dihydropyrazol-4-ylidene]hydrazino}-2'-hydroxybiphenyl-3-carboxylic acid;

3'-N-tert-butoxycarbonylamino-3-{N'-[1-(3,4-Dimethylphenyl)-3-methyl-5-oxo-1,5-dihydropyrazol-4-ylidene]hydrazino}-2-hydroxybiphenyl;

3'-amino-3-{N'-[1-(3,4-dimethylphenyl)-3-methyl-5-oxo-1,5-dihydropyrazol-4-ylidene]hydrazino}-2-hydroxybiphenyl;

3-{N'-[1-(3-fluorophenyl)-3-methyl-5-oxo-1,5-dihydropyrazol-4-ylidene]hydrazino}-2-hydroxy-3'-tetrazol-5-ylbiphenyl;

3'-{N'-[1-(3-fluorophenyl)-3-methyl-5-oxo-1,5-dihydropyrazol-4-ylidene]hydrazino}-2'-hydroxybiphenyl-3-carboxylic acid;

3-{N'-[3-methyl-5-oxo-1-(2,3,4,5,6-pentafluorophenyl)-1,5-dihydropyrazol-4-ylidene]hydrazino}-2-hydroxy-3'-tetrazol-5-ylbiphenyl;

3'-{N'-[3-methyl-5-oxo-1-(2,3,4,5,6-pentafluorophenyl)-1,5-dihydropyrazol-4-ylidene]hydrazino}-2'-hydroxybiphenyl-3-carboxylic acid;

3'-{N'-[1-(3,4-difluorophenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-methoxymethyl-5-oxo-1,5-dihydropyrazol-4-ylidene]hydrazino}-2'-hydroxybiphenyl-3-carboxylic acid;

3-{N'-[1-(3,4-dimethylphenyl)-3-methoxymethyl-5-oxo-1,5-dihydropyrazol-4-ylidene]hydrazino}-2-hydroxy-3'-tetrazol-5-ylbiphenyl;

3-{N'-[1-(3,4-difluorophenyl)-3-methyl-5-oxo-1,5-dihydropyrazol-4-ylidene]hydrazino}-2-hydroxy-3'-tetrazol-5-ylbiphenyl;

3'-{N'-[1-(3,4-dimethylphenyl)-5-oxo-3-trifluoromethyl-1,5-dihydropyrazol-4-ylidene]hydrazino}-2'-hydroxybiphenyl-3-carboxylic acid;

3'-{N'-[1-(3,4-dimethylphenyl)-3-methyl-5-oxo-1,5-dihydropyrazol-4-ylidene]hydrazino}-6-fluoro-2'-hydroxybiphenyl-3-carboxylic acid;

3'-{N'-[1-(3,4-dimethylphenyl)-5-oxo-3-propyl-1,5-dihydropyrazol-4-ylidene]hydrazino}-2'-hydroxybiphenyl-3-carboxylic acid;

3-{N'-[1-(3,4-dimethylphenyl)-5-oxo-3-propyl-1,5-dihydropyrazol-4-ylidene]hydrazino}-2-hydroxy-3'-tetrazol-5-ylbiphenyl;

3'-{N'-[1-(3,4-dimethylphenyl)-3-(1-methyl-1H-pyrrol-3-yl)-5-oxo-1,5-dihydropyrazol-4-ylidene]hydrazino}-2'-hydroxybiphenyl-3-carboxylic acid;

3-{N'-[1-(3,4-dimethylphenyl)-3-(1-methyl-1H-pyrrol-3-yl)-5-oxo-1,5-dihydropyrazol-4-ylidene]hydrazino}-2-hydroxy-3'-tetrazol-5-ylbiphenyl;

3'-{N'-[1-(3,4-dimethylphenyl)-3-furan-2-yl-5-oxo-1,5-dihydropyrazol-4-ylidene]hydrazino}-2'-hydroxybiphenyl-3-carboxylic acid;

3-{N'-[1-(3,4-dimethylphenyl)-3-furan-2-yl-5-oxo-1,5-dihydropyrazol-4-ylidene]hydrazino}-2-hydroxy-3'-tetrazol-5-ylbiphenyl;

N-(2'-hydroxy-3'-{N'-[3-methyl-5-oxo-1-(4-trifluoromethyl-phenyl)-1,5-dihydro-pyrazol-4-ylidene]hydrazino}biphenyl-3-yl)-1,1,1-trifluoromethanesulfonamide;

N-(2'-hydroxy-3'-{N'-[1-(3-fluoro-4-methylphenyl)-3-methyl-5-oxo-1,5-dihydro-pyrazol-4-ylidene]hydrazino}biphenyl-3-yl)-1,1,1-trifluoromethanesulfonamide;

N-(2'-hydroxy-3'-{N'-[1-(4-fluoro-3-methylphenyl)-3-methyl-5-oxo-1,5-dihydro-pyrazol-4-ylidene]hydrazino}biphenyl-3-yl)-1,1,1-trifluoromethanesulfonamide;

N-(2'-hydroxy-3'-{N'-[1-(3,4-difluorophenyl)-3-methyl-5-oxo-1,5-dihydro-pyrazol-4-ylidene]hydrazino}biphenyl-3-yl)-1,1,1-trifluoromethanesulfonamide;

N-(3'-{N'-[1-(3,4-dimethylphenyl)-3-methyl-5-oxo-1,5-dihydropyrazol-4-ylidene]hydrazino}-2'-hydroxybiphenyl-3-yl)guanidine;

3'-{N'-[1-(3,4-dimethylphenyl)-3-ethyl-5-oxo-1,5-dihydropyrazol-4-ylidene]hydrazino}-2'-hydroxybiphenyl-3-carboxylic acid;

3-{N'-[1-(3,4-dimethylphenyl)-3-ethyl-5-oxo-1,5-dihydropyrazol-4-ylidene]hydrazino}-2-hydroxy-3'-tetrazol-5-ylbiphenyl;

3'-{N'-[1-(3,4-dimethylphenyl)-5-oxo-3-thien-2-yl-1,5-dihydropyrazol-4-ylidene]hydrazino}-2'-hydroxybiphenyl-3-carboxylic acid;

3'-{N'-[3-cyclopropyl-1-(3,4-dimethylphenyl)-5-oxo-1,5-dihydropyrazol-4-ylidene]hydrazino}-2'-hydroxybiphenyl-3-carboxylic acid;

3'-{N'-[1-(3,4-dimethylphenyl)-5-oxo-3-thiazol-2-yl-1,5-dihydropyrazol-4-ylidene]hydrazino}-2'-hydroxybiphenyl-3-carboxylic acid;

3'-{N'-[1N-(3,4-dimethylphenyl)-5-oxo-1,5-dihydropyrazol-4-ylidene]hydrazino}-2'-hydroxybiphenyl-3-carboxylic acid;

3'-{N'-[1-(3,4-dimethylphenyl)-3-(1-methylethyl)-5-oxo-1,5-dihydropyrazol-4-ylidene]hydrazino}-2'-hydroxybiphenyl-3-carboxylic acid;

3'-{N'-[3-(benzyloxymethyl)-1-(3,4-dimethylphenyl)-5-oxo-1,5-dihydropyrazol-4-ylidene]hydrazino}-2'-hydroxybiphenyl-3-carboxylic acid;

3'-{N'-[3-ethyl-5-oxo-1-(4-trifluoromethylphenyl)-1,5-dihydropyrazol-4-ylidene]hydrazino}-2'-hydroxybiphenyl-3-carboxylic acid;

3'-{N'-[5-oxo-1-(4-trifluoromethylphenyl)-1,5-dihydropyrazol-4-ylidene]hydrazino}-2'-hydroxybiphenyl-3-carboxylic acid;

3'-{N'-[-1-(3,4-dimethylphenyl)-3-hydroxymethyl-5-oxo-1,5-dihydropyrazol-4-ylidene]hydrazino}-2'-hydroxybiphenyl-3-carboxylic acid;

3'-{N'-[3-benzyloxymethyl-5-oxo-1-(4-trifluoromethylphenyl)-1,5-dihydropyrazol-4-ylidene]hydrazino}-2'-hydroxybiphenyl-3-carboxylic acid;

3'-{N'-[-1-(3,4-dimethylphenyl)-3-methylsulfanylmethyl-5-oxo-1,5-dihydropyrazol-4-ylidene]hydrazino}-2'-hydroxybiphenyl-3-carboxylic acid;

3'-{N'-[-1-(3,4-dimethylphenyl)-5-oxo-3-thiophen-3-yl-1,5-dihydropyrazol-4-ylidene]hydrazino}-2'-hydroxybiphenyl-3-carboxylic acid;

3'-{N'-[5-oxo-1-(4-trifluoromethylphenyl)-3-thiophen-3-yl-1,5-dihydropyrazol-4-ylidene]hydrazino}-2'-hydroxybiphenyl-3-carboxylic acid;

3'-{N'-[5-oxo-1-(4-trifluoromethylphenyl)-3-methylsulfanylmethyl-1,5-dihydropyrazol-4-ylidene]hydrazino}-2'-hydroxybiphenyl-3-carboxylic acid;

N-(3'-{N'-[1-(3,4-dimethylphenyl)-3-methyl-5-oxo-1,5-dihydro-pyrazol-4-ylidene]hydrazino}-2'-hydroxybiphenyl-3-yl)methanesulfonamide;

3'-[N'-(1-benzo[1,3]dioxol-5-yl-3-methyl-5-oxo-1,5-dihydropyrazol-4-ylidene)hydrazino]-2'-hydroxybiphenyl-3-carboxylic acid;

3'-{N'-[1-(3,5-dimethylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-methyl-5-oxo-1,5-dihydropyrazol-4-ylidene]hydrazino}-4'-hydroxybiphenyl-4-carboxylic acid;

3'-{N'-[1-(3-chloro-4-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-methyl-5-oxo-1,5-dihydropyrazol-4-ylidene]hydrazino}-4'-hydroxybiphenyl-3-carboxylic acid;

3'-{N'-[1-(3,4-dimethylphenyl)-3-methyl-5-oxo-1,5-dihydropyrazol-4-ylidene]hydrazino}-2'-hydroxybiphenyl-3-phosphonic acid;

3'-{N'-[1-(3,4-dimethylphenyl)-3-methyl-5-oxo-1,5-dihydropyrazol-4-ylidene]hydrazino}-2'-hydroxybiphenyl-3,4-dicarboxylic acid;

2',6-dihydroxy-3-{N'-[1-(3,4-dimethylphenyl)-3-methyl-5-oxo-1,5-dihydropyrazol-4-ylidene]hydrazino}biphenyl-3-carboxylic acid;

4-aza-3'-{N'-[1-(3,4-dimethylphenyl)-3-methyl-5-oxo-1,5-dihydropyrazol-4-ylidene]hydrazino}-2'-hydroxybiphenyl-5-carboxylic acid;

3'-{N'-[1-(3,4-dimethylphenyl)-3-methyl-5-oxo-1,5-dihydropyrazol-4-ylidene]hydrazino}-2'-hydroxybiphenyl-3-sulfonic acid; and 5-(3'-{N'-[1-(3,4-Dimethylphenyl)-3-methyl-5-oxo-1,5-dihydropyrazol-4-ylidene]hydrazino}-2'-hydroxybiphenyl-3-ylmethylene)thiazolidine-2,4-dione;

and pharmaceutically acceptable salts, hydrates, solvates and esters thereof.

Compounds of Formula (I) are included in the pharmaceutical compositions of the invention and used in the methods of the invention.

By the term "protected hydroxy" or "protected —OH" as used herein, is meant the alcoholic or carboxylic-OH groups which can be protected by conventional blocking groups in the art such as described in "Protective Groups In Organic Synthesis" by Theodora W. Greene, Wiley-Interscience, 1981, New York. Compounds containing protected hydroxy groups may also be useful as intermediates in the preparation of the pharmaceutically active compounds of the invention.

By the term "aryl" as used herein, unless otherwise defined, is meant a cyclic or polycyclic aromatic ring containing from 1 to 14 carbon atoms and optionally containing from one to five heteroatoms, provided that when the number of carbon atoms is 1 the aromatic ring contains at least four heteroatoms, when the number of carbon atoms is 2 the aromatic ring contains at least three heteroatoms, when the number of carbons is 3 the aromatic ring contains at least two heteroatoms and when the number of carbon atoms is 4 the aromatic ring contains at least one heteroatom.

By the term "$C_1$-$C_{12}$aryl" as used herein, unless otherwise defined, is meant phenyl, naphthalene, 3,4-methylenedioxyphenyl, pyridine, biphenyl, quinoline, pyrimidine, quinazoline, thiophene, furan, pyrrole, pyrazole, imidazole and tetrazole.

When referring to compounds of Formula (I) and (II), the term "substituted" as used herein, unless otherwise defined, is meant that the subject chemical moiety has one or more substituents selected from the group consisting of: —$CO_2R^{20}$, aryl, —$C(O)NHS(O)_2R^{20}$, —$NHS(O)_2R^{20}$, hydroxyalkyl, alkoxy, —$C(O)NR^{21}R^{22}$, acyloxy, alkyl, amino, N-acylamino, hydroxy, —$(CH_2)_gC(O)OR^8$, —$S(O)_n R^8$, nitro, tetrazole, cyano, oxo, halogen, trifluoromethyl, protected —OH and a heterocyclic methylene substituent as represented by Formula (III),

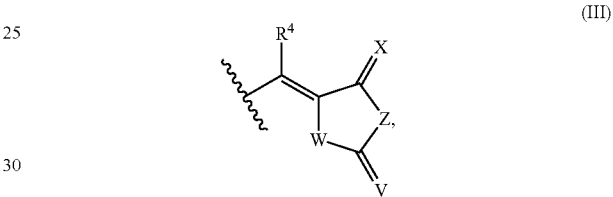

(III)

where g is 0-6; $R^8$ is hydrogen or alkyl; $R^{20}$ is selected form hydrogen, $C_1$-$C_4$alkyl, aryl and trifluoromethyl; $R^{21}$ and $R^{22}$ are independently selected from hydrogen, $C_1$-$C_4$alkyl, aryl and trifluoromethyl; V, W, X and Z are each independently selected from O, S, and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl; and n is 0-2.

When referring to compounds of Formula (V) and (VI), the term "substituted" as used herein, unless otherwise defined, is meant that the subject chemical moiety has one or more substituents selected from the group consisting of: —$CO_2R^{20}$, aryl, —$C(O)NHS(O)_2R^{20}$, —$NHS(O)_2R^{20}$, hydroxyalkyl, alkoxy, —$C(O)NR^{21}R^{22}$, acyloxy, alkyl, amino, N-acylamino, hydroxy, —$(CH_2)_gC(O)OR^8$, —$S(O)_n R^8$, nitro, tetrazole, cyano, oxo, halogen, trifluoromethyl and protected —OH, where g is 0-6, $R^8$ is hydrogen or alkyl, $R^{20}$ is selected form hydrogen, $C_1$-$C_4$alkyl, aryl and trifluoromethyl, and $R^{21}$ and $R^{22}$ are independently selected form hydrogen, $C_1$-$C_4$alkyl, aryl and trifluoromethyl, and n is 0-2.

By the term "alkoxy" as used herein is meant —Oalkyl where alkyl is as described herein including —$OCH_3$ and —$OC(CH_3)_2CH_3$.

The term "cycloalkyl" as used herein unless otherwise defined, is meant a nonaromatic, unsaturated or saturated, cyclic or polycyclic $C_3$-$C_{12}$.

Examples of cycloalkyl and substituted cycloalkyl substituents as used herein include: cyclohexyl, 4-hydroxycyclohexyl, 2-ethylcyclohexyl, propyl 4-methoxycyclohexyl, 4-methoxycyclohexyl, 4-carboxycyclohexyl, cyclopropyl and cyclopentyl.

By the term "acyloxy" as used herein is meant —OC(O)alkyl where alkyl is as described herein. Examples of acyloxy substituents as used herein include: —OC(O)CH₃, —OC(O)CH(CH₃)₂ and —OC(O)(CH₂)₃CH₃.

By the term "N-acylamino" as used herein is meant —N(H)C(O)alkyl, where alkyl is as described herein. Examples of N-acylamino substituents as used herein include: —N(H)C(O)CH₃, —N(H)C(O)CH(CH₃)₂ and —N(H)C(O)(CH₂)₃CH₃.

By the term "aryloxy" as used herein is meant —Oaryl where aryl is phenyl, naphthyl, 3,4-methylenedioxyphenyl, pyridyl or biphenyl optionally substituted with one or more substituents selected from the group consisting of: alkyl, hydroxyalkyl, alkoxy, trifluoromethyl, acyloxy, amino, N-acylamino, hydroxy, —(CH₂)$_g$C(O)OR⁸, —S(O)$_n$R⁸, nitro, cyano, halogen and protected —OH, where g is 0-6, R⁸ is hydrogen or alkyl, and n is 0-2. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain, and unless otherwise defined, the carbon chain will contain from 1 to 12 carbon atoms. Examples of alkyl substituents as used herein include: —CH₃, —CH₂—CH₃, —CH₂—CH₂—CH₃, —CH(CH₃)₂, —C(CH₃)₃, —(CH₂)₃—CH₃, —CH₂—CH(CH₃)₂, —CH(CH₃)—CH₂—CH₃, —CH═CH₂, and —C—C—CH₃.

By the term "treating" and derivatives thereof as used herein, is meant prophylatic and therapeutic therapy.

All publications, including but not limited to patents and patent applications, cited in this specification are herein incorporated by reference as though fully set forth.

Compounds of Formula (I) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or prodrug formulations.

The novel compounds of Formulas I and II are prepared as shown in Schemes I to IV below, or by analogous methods, wherein the 'R' substituents, AR, Y and m are as defined in Formulas I and II respectively and provided that the 'R' and m substituents, AR and Y do not include any such substituents that render inoperative the processes of Schemes I to IV. All of the starting materials are commercially available or are readily made from commercially available starting materials by those of skill in the art.

Scheme I

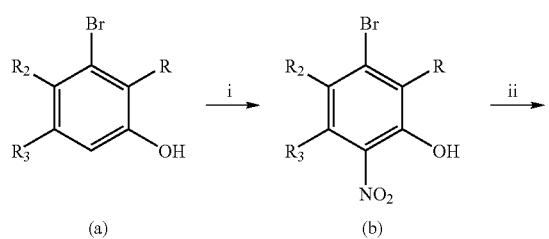

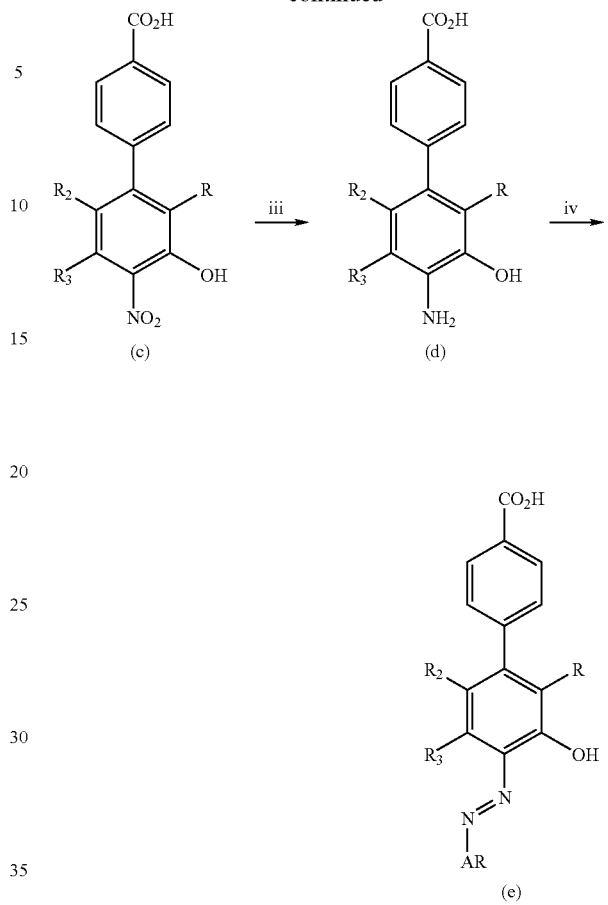

i), nitric acid;, sulfuric acid;; ii) 4-carboxyphenylboronic acid;, Pd(PPh₃)₄, Na₂CO₃, dioxane, water; iii) H₂, Pd—C; iv) NaNO₂, AR, NaHCO₃, water, EtOH Scheme I outlines the formation of Formula I compounds. As used in scheme I, a 3-bromophenol (a) is nitrated with nitric acid or sodium nitrate and sulfuric acid to give nitro phenol (b). Coupling of (b) with a substituted arylboronic acid, such as 3-carboxyphenylboronic acid or 4-carboxyphenylboronic acid in the presence of a catalyst, preferably tetrakistriphenylphosphino palladium and a base such as sodium carbonate ot triethylamine in a suitable solvent such as aqueous 1,4-dioxane or dimethylformamide afforded substituted aryl compound (c). Reduction of the nitro group by catalytic hydrogenation or mediated by a reducing metal such as iron of tin dichloride in a suitable solvent such as ethanol, acetic acid or water gives the aniline (d). Compound (d) is diazotized by reaction with sodium nitrite and an appropriate acid, such as nitric acid, sulfuric acid or, preferably, hydrochloric acid, in an appropriate aqueous solvent, such as water or, preferably an ethanol-water mixture to produce a diazonium species which is directly converted to compound (e) in a coupling reaction with an appropriate aryl species in the presence of a base, preferably sodium hydrogen carbonate, or an acid, preferably hydrochloric acid.

Scheme II

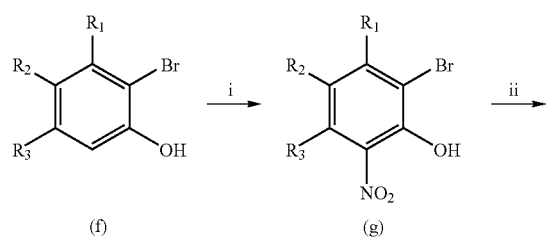

(f) → (g)

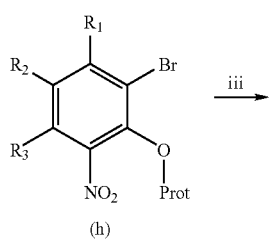

(h)

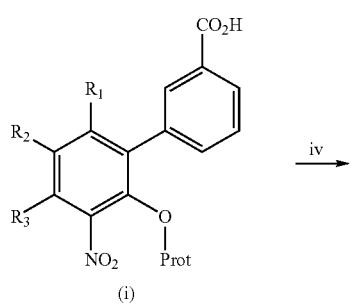

(i)

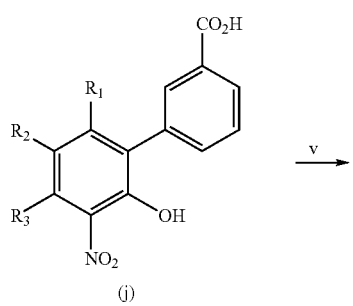

(j)

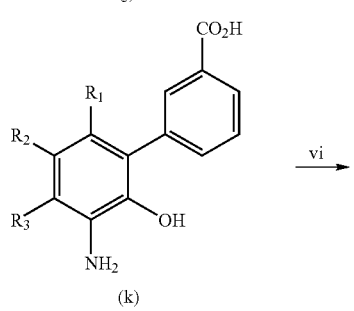

(k)

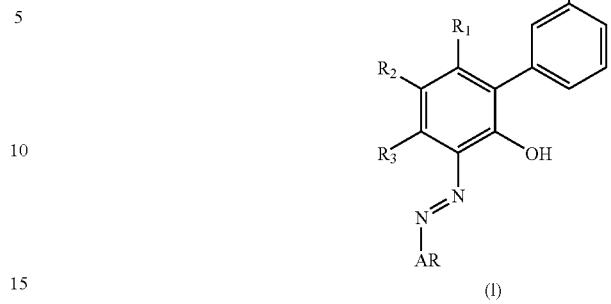

(l)

i), NaNO$_2$, sulfuric acid;; ii), MeI, K$_2$CO$_3$, acetone; iii) 3-carboxyphenylboronic acid;, Pd(PPh$_3$)$_4$, Na$_2$CO$_3$, dioxane, water; iv) 48% aqu. HBr, AcOH; v) H$_2$, Pd—C; yl) NaNO$_2$, AR, NaHCO$_3$, water, EtOH Scheme II outlines an alternative synthesis of Formula I compounds. A 2-bromophenol (f) (such as 2-bromophenol or 2-bromo-5-methylphenol is nitrated with nitric acid or sodium nitrate and sulfuric acid, to give nitro compound (g). The phenol (g) is then protected by reaction with an alkylating agent such as benzyl bromide or preferably methyl iodide in the presence of a base such as sodium hydride or potassium carbonate in a suitable solvent such as dimethylformamide, tetrahydrofuran or acetone to give protected nitrophenol (h) (Prot=alkyl or substituted alkyl, e.g. methyl, benzyl). Coupling of (h) with a substituted arylboronic acid, such as 3-carboxyphenylboronic acid or 4-carboxyphenylboronic acid, in the presence of a catalyst, preferably tetrakistriphenylphosphino palladium and a base such as sodium carbonate to triethylamine in a suitable solvent such as aqueous 1,4-dioxane or dimethylformamide afforded substituted aryl compound (i). Removal of the protecting group (Prot) is accomplished using a protic or Lewis acid; such as concentrated hydrobromic acid, boron tribromide or trimethylsilyl iodide to afford the phenol (j). Reduction of the nitro group by catalytic hydrogenation or mediated by a reducing metal such as iron of tin dichloride in a suitable solvent such as ethanol, acetic acid; or water gives the aniline (k). Compound (k) is diazotized by reaction with sodium nitrite and an appropriate acid, such as nitric acid, sulfuric acid or, preferably, hydrochloric acid, in an appropriate aqueous solvent, such as water or, preferably, an ethanol-water mixture to produce a diazonium species which is directly converted to compound (1) in a coupling reaction with an appropriate aryl species in the presence of a base, preferably sodium hydrogen carbonate, or an acid, preferably hydrochloric acid.

Scheme III

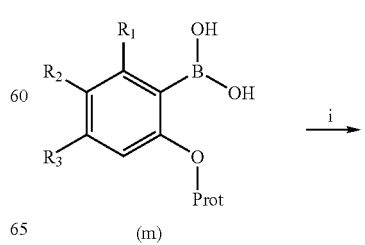

(m)

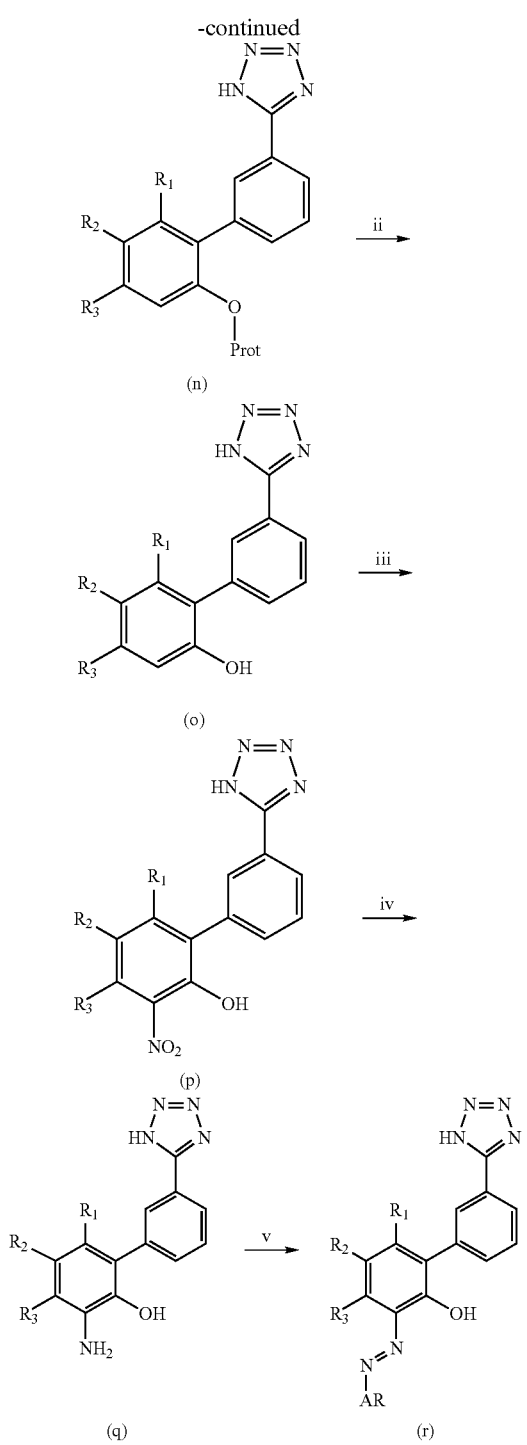

(n)

(o)

(p)

(q) → (r)

i) 5-(3-bromophenyl)tetrazole, Pd(PPh$_3$)$_4$, Na$_2$CO$_3$, dioxane, water; ii) 48% aqu. HBr, AcOH; iii) HNO$_2$, AcOH; iv) H$_2$, Pd—C; v) NaNO$_2$, AR, NaHCO$_3$, water, EtOH Scheme III outlines a further procedure for the synthesis of Formula I compounds. A protected hydroxyphenylboronic acid; (m) (Prot=alkyl or substituted alkyl, e.g. methyl, benzyl) such as 5-chloro-2-methoxyphenylboronic acid, 5-fluoro-2-methoxyphenyl, boronic acid or 2-methoxy-5-formylphenylboronic acid, is coupled with a substituted halogenoaryl species, such as 5-(3-bromophenyl)tetrazole or 5-bromonicotinic acid, in the presence of a catalyst, preferably tetrakistriphenylphosphino palladium, and a base, such as sodium carbonate or triethylamine in a suitable solvent such as aqueous 1,4-dioxane or dimethylformamide afforded substituted aryl compound (n). Removal of the protecting group Prot is accomplished using an protic or Lewis acid, such as concentrated hydrobromic acid, boron tribromide or trimethylsilyl iodide to afford the phenol (o). Nitration of (o) with nitric acid, or sodium nitrate in the presence of an acid, such as acetic or hydrochloric acid, affords the nitro compound (p). Reduction of the nitro group by catalytic hydrogenation or mediated by a reducing metal such as iron of tin dichloride in a suitable solvent such as ethanol, acetic acid or water gives the aniline (q). Compound (q) is diazotized by reaction with sodium nitrite and an appropriate acid, such as nitric acid, sulfuric acid or, preferably, hydrochloric acid, in an appropriate aqueous solvent, such as water or, preferably, an ethanol-water mixture to produce a diazonium species which is directly converted to compound (r) in a coupling reaction with an appropriate aryl species in the presence of a base, preferably sodium hydrogen carbonate, or an acid, preferably hydrochloric acid.

Scheme IV

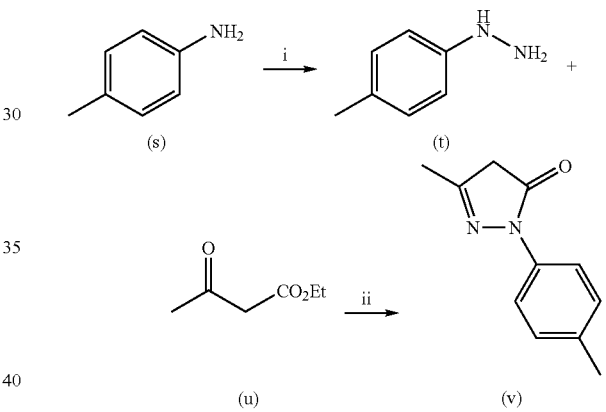

(s) → (t) + (u) → (v)

i) NaNO$_2$, HCl, water then SnCl$_2$, water; ii) AcOH, heat

Scheme IV outlines the formation of pyrazoles for use in scheme I-III. An amine such as 4-methylaniline, compound (s), is diazotized by the action of sodium nitrite and an appropriate acid, such as hydrochloric acid, nitric acid or sulfuric acid, in an appropriate aqueous solvent system, such as water or ethanol-water mixtures, then reduced in situ by tin chloride to afford hydrazine, compound (t). The hydrazine is then condensed with a electrophilic carbonyl species such as ethyl acetoacetate (u), ethyl cyanoacetate or diethyl malonate, in an appropriate solvent such as acetic acid or ethanol at an appropriate temperature typically 0-100° to give the corresponding pyrazole, compound (v) as described herein.

In preparing the presently invented compounds of Formula (I), the following novel intermediates are prepared:
4'-Amino-3'-hydroxybiphenyl-4-carboxylic acid;
4'-Amino-3'-hydroxybiphenyl-3-carboxylic acid;
3'-Amino-2'-hydroxybiphenyl-3-carboxylic acid;
3'-Amino-2'-hydroxybiphenyl-4-carboxylic acid;
3-Amino-2-hydroxy-3'-(1H-tetrazol-5-yl)biphenyl;
3-Amino-2-hydroxy-4'-(1H-tetrazol-5-yl)biphenyl;
3-Amino-5-chloro-2-hydroxy-4'-(H-tetrazol-5-yl)-biphenyl;
6-(3-Amino-2-hydroxyphenyl)pyridine-2-carboxylic acid;

6-(3-Amino-5-chloro-2-hydroxyphenyl)pyridine-2-carboxylic acid;
6-(3-Amino-2-hydroxy-5-methylphenyl)pyridine-2-carboxylic acid;
5-(3-Amino-2-hydroxyphenyl)nicotinic acid;
5-(3-Amino-2-hydroxy-5-methylphenyl)nicotinic acid;
2-(3-Amino-2-hydroxyphenyl)isonicotinic acid;
3'-Amino-2'-hydroxy-5'-methylbiphenyl-3-carboxylic acid;
3'-Amino-5'-fluoro-2'-hydroxybiphenyl-3-carboxylic acid;
3'-Amino-5'-chloro-2'-hydroxybiphenyl-3-carboxylic acid;
3'-Amino-2'-hydroxybiphenyl-3,5-dicarboxylic acid;
N-[1-(3'-Amino-2'-hydroxybiphenyl-3-yl)methanoyl]methanesulfonamide;
N-(3'-Amino-2'-hydroxybiphenyl-3-yl)-1,1,1-trifluoromethanesulfonamide;
(3'-Amino-2'-hydroxybiphenyl-3-yl)phosphonic acid;
3'-Amino-2'-hydroxybiphenyl-3,4-dicarboxylic acid;
3'-Amino-4,2'-dihydroxybiphenyl-3-carboxylic acid;
3'-Amino-2'-hydroxybiphenyl-3-sulfonic acid;
3'-Hydroxy-4'-nitrobiphenyl-4-carboxylic acid;
3'-Hydroxy-4'-nitrobiphenyl-3-carboxylic acid;
2'-Hydroxy-3'-nitrobiphenyl-3-carboxylic acid;
2'-Hydroxy-3'-nitrobiphenyl-4-carboxylic acid;
5-Chloro-2-hydroxy-3-nitro-3'-(1H-tetrazol-5-yl)biphenyl;
5-Chloro-2-hydroxy-3-nitro-4'-(1H-tetrazol-5-yl)biphenyl;
6-(5-Chloro-2-hydroxy-3-nitrophenyl)pyridine-2-carboxylic acid;
6-(2-Hydroxy-5-methyl-3-nitrophenyl)pyridine-2-carboxylic acid;
5-(5-Chloro-2-hydroxy-3-nitrophenyl)nicotinic acid;
5-(5-Chloro-2-hydroxy-5-methyl-3-nitrophenyl)nicotinic acid;
2-(5-Chloro-2-hydroxy-3-nitrophenyl)isonicotinic acid;
5'-Chloro-2'-hydroxy-3'-nitrobiphenyl-3-carboxylic acid;
5'-Chloro-2'-hydroxy-3'-nitrobiphenyl-3,5-dicarboxylic acid;
N-[1-(5'-Chloro-2'-hydroxy-3'-nitrobiphenyl-3-yl)methanoyl]methanesulfonamide;
1,1,1-Trifluoro-N-(2'-hydroxy-3'-nitrobiphenyl-3-yl)methanesulfonamide;
(5'-Chloro-2'-hydroxy-3'-nitrobiphenyl-3-yl)phosphonic acid;
5'-Chloro-2'-hydroxy-3'-nitrobiphenyl-3,4-dicarboxylic acid;
5'-Chloro-4,2'-dihydroxy-3'-nitrobiphenyl-3-carboxylic acid;
5'-Chloro-2'-hydroxy-3'-nitrobiphenyl-3-sulfonic acid;
2'-Methoxy-3'-nitrobiphenyl-3-carboxylic acid;
2'-Methoxy-3'-nitrobiphenyl-4-carboxylic acid;
5-Chloro-2-hydroxy-3'-(1H-tetrazol-5-yl)biphenyl;
5-Chloro-2-hydroxy-4'-(1H-tetrazol-5-yl)biphenyl;
6-(5-Chloro-2-hydroxyphenyl)pyridine-2-carboxylic acid;
6-(2-Hydroxy-5-methylphenyl)pyridine-2-carboxylic acid;
6-(2-Hydroxy-5-methylphenyl)pyridine-2-carboxylic acid;
5-(5-Chloro-2-hydroxy-5-methylphenyl)nicotinic acid;
2-(5-Chloro-2-hydroxyphenyl)isonicotinic acid;
5'-Chloro-2'-hydroxybiphenyl-3-carboxylic acid;
5'-Chloro-2'-hydroxybiphenyl-3,5-dicarboxylic acid;
N-[1-(5'-Chloro-2'-hydroxybiphenyl-3-yl)methanoyl]methanesulfonamide;
3'-Amino-3-nitrobiphenyl-2-ol;
(5'-Chloro-2'-hydroxybiphenyl-3-yl)phosphonic acid;
5'-Chloro-2'-hydroxybiphenyl-3,4-dicarboxylic acid;
5'-Chloro-4,2'-dihydroxybiphenyl-3-carboxylic acid;
5'-Chloro-2'-hydroxybiphenyl-3-sulfonic acid;
5-Chloro-2-methoxy-3'-(1H-tetrazol-5-yl)biphenyl;
5-Chloro-2-methoxy-4'-(1H-tetrazol-5-yl)biphenyl;
6-(5-Chloro-2-methoxyphenyl)pyridine-2-carboxylic acid;
6-(2-Methoxy-5-methylphenyl)pyridine-2-carboxylic acid;
6-(2-Methoxy-5-methylphenyl)pyridine-2-carboxylic acid;
5-(5-Chloro-2-methoxy-5-methylphenyl)nicotinic acid;
2-(5-Chloro-2-methoxyphenyl)isonicotinic acid;
5'-Chloro-2'-methoxybiphenyl-3-carboxylic acid;
5'-Chloro-2'-methoxybiphenyl-3,5-dicarboxylic acid;
N-[1-(5'-Chloro-2'-methoxybiphenyl-3-yl)methanoyl]methanesulfonamide;
N-(2'-Methoxy-3'-nitrobiphenyl-3-yl)-acetamide;
(5'-Chloro-2'-methoxybiphenyl-3-yl)phosphonic acid;
5'-Chloro-2'-methoxybiphenyl-3,4-dicarboxylic acid;
5'-Chloro-4-hydroxy-2'-methoxybiphenyl-3-carboxylic acid; and
5'-Chloro-2'-methoxybiphenyl-3-sulfonic acid.

The treatment of thrombocytopenia, as described herein, is accomplished by increasing the production of platelets.

By the term "co-administering" and derivatives thereof as used herein is meant either simultaneous administration or any manner of separate sequential administration of a TPO mimetic compound, as described herein, and a further active ingredient or ingredients, known to treat thrombocytopenia, including chemotherapy-induced thrombocytopenia and bone marrow transplantation and other conditions with depressed platelet production. The term further active ingredient or ingredients, as used herein, includes any compound or therapeutic agent known to or that demonstrates advantageous properties when administered with TPO or a TPO mimetic. Preferably, if the administration is not simultaneous, the compounds are administered in a close time proximity to each other. Furthermore, it does not matter if the compounds are administered in the same dosage form, e.g. one compound may be administered topically and another compound may be administered orally.

Examples of a further active ingredient or ingredients for use in combination with the presently invented TPO mimetic compounds include but are not limited to: chemoprotective or myeloprotective agents such as G-CSF, BB10010 (Clemons et al., *Breast Cancer Res. Treatment*, 1999, 57, 127), amifostine (Ethyol) (Fetscher et al., *Current Opinion in Hemat.*, 2000, 7, 255-60), SCF, IL-11, MCP-4, IL-1-beta, AcSDKP (Gaudron et al., *Stem Cells*, 1999, 17, 100-6), TNF-a, TGF-b, MIP-1a (Egger et al., *Bone Marrow Transpl.*, 1998, 22 (Suppl. 2), 34-35), and other molecules identified as having anti-apoptotic, survival or proliferative properties.

Tpo has been demonstrated to act as a mobilizer of stem cells into the peripheral blood (Neumann T. A. et al., *Cytokines, Cell, & Mol. Ther.*, 2000, 6, 47-56). This activity can synergize with stem cell mobilizers such as G-CSF (Somolo et al., *Blood*, 1999, 93, 2798-2806). The TPO mimetic compounds of the present invention are thus useful in increasing the numbers of stem cells in circulation in donors prior to leukapheresis for hematopoietic stem-cell transplantation in patients receiving myelo-ablative chemotherapy.

Likewise, TPO stimulates growth of myeloid cells, particularly those of granulocyte/macrophage lineage (Holly et al., U.S. Pat. No. 5,989,537). Granulocyte/macrophage progenitors are cells of the myeloid lineage that mature as neutrophils, monocytes, basophils and eosinophils. The compounds described in the present invention have thus therapeutic utility in stimulating the proliferation of neutrophils in patients with neutropenic conditions.

Additional examples of a further active ingredient or ingredients for use in combination with the presently invented TPO mimetic compounds include but are not limited to: stem cell, megakaryocyte, neutrophil mobilizers such as chemotherapeutic agents (i.e., cytoxan, etoposide, cisplatin, Ballestrero A. et al., *Oncology*, 2000, 59, 7-13), chemokines, IL-8, Gro-beta (King, A. G. et al. *J. Immun.*, 2000, 164, 3774-82), receptor agonist or antagonist antibodies, small molecule cytokine or receptor agonists or antagonists, SCF, Flt3 ligand, adhesion molecule inhibitors or antibodies such as: anti-VLA-4 (Kikuta T. et al., *Exp. Hemat.*, 2000, 28, 311-7) or anti-CD44 (Vermeulen M. et al., *Blood*, 1998, 92, 894-900), cytokine/chemokine/interleukin or receptor agonist or antagonist antibodies, MCP-4 (Berkhout T A., et al., *J. Biol. Chem.*, 1997, 272, 16404-16413; Uguccioni M. et al., *J. Exp. Med.*, 1996, 183, 2379-2384).

Because the pharmaceutically active compounds of the present invention are active as TPO mimetics they exhibit therapeutic utility in treating thrombocytopenia and other conditions with depressed platelet production.

By the term "thrombocytopenia" and derivatives thereof as used herein is to be broadly interpreted as any decrease in the number of blood platelets below what is considered normal or desired for a healthy individual. Thrombocytopenia is known to have many causative factors, including but not limited to, radiation therapy, chemotherapy, immune therapy, immune thrombocytopenic purpura (ITP, Bussel J. B., *Seminars in Hematology*, 2000, 37, Suppl 1, 1-49), myelodysplastic syndrom (MDS), aplastic anemia, AML, CML, viral infections (including, but not limited to; HIV, hepatitis C, parvovirus) liver disease, myeloablation, bone marrow transplant, stem cell transplant, peripheral blood stem cell transplant, progenitor cell defect, polymorphisms in stem cells and progenitor cells, defects in Tpo, neutropenia (Sawai, N. J. *Leukocyte Biol.*, 2000, 68, 137-43), dendritic cell mobilization (Kuter D. J. *Seminars in Hematology*, 2000, 37, Suppl 4, 41-49), proliferation, activation or differentiation. The pharmaceutically active compounds of this invention are useful in treating thrombocytopenia regardless of the factor or factors causing the condition. The pharmaceutically active compounds of this invention are also useful in treating thrombocytopenia when the causative factor or factors of the condition are unknown or have yet to be identified.

Prophylactic use of the compounds of this invention is contemplated whenever a decrease in blood or blood platelets is anticipated. Prophylactic use of the compounds of this invention results in a build up of platelets or a commencement of platelet production prior to an anticipated loss of blood or blood platelets. Prophylactic uses of the compounds of this invention includes but is not limited to transplant surgery, surgery, anesthesia prior to child birth and gut protection.

Human dendritic cells have been shown to express the TPO receptor (Kumamoto et al., *Br. J. Haem*, 1999, 105, 1025-1033) and TPO is a potent mobilizer of dendritic cells. The TPO mimetic compounds of the current invention are also useful as a vaccine adjuvant in that they increase the activity and mobility of dendritic cells. The pharmaceutically active compounds of this invention are useful as an immunological adjuvant, given in combination with an orally, transdermally or subcutaneously delivered vaccine and/or immunomodulator, by increasing the activity and mobility of dendritic cells.

Tpo is known to have various effects including anti-apoptotic/survival effects on megakaryocytes, platelets and stem cells, and proliferative effects on stem cells and megakaryocytic cells (Kuter D. J. Seminars in Hematology, 2000, 37, 41-9). These Tpo activities effectively increase the number of stem and progenitor cells so that there is synergistic effects when Tpo is used in conjunction with other cytokines that induce differentiation.

The TPO mimetic compounds of the current invention are also useful in acting on cells for survival or proliferation in conjunction with other agents known to act on cells for survival or proliferation. Such other agents include but are not limited to: G-CSF, GM-CSF, TPO, M-CSF, EPO, Gro-beta, IL-11, SCF, FLT3 ligand, LIF, IL-3, IL-6, IL-1, Progenipoietin, NESP, SD-01, or IL-5 or a biologically active derivative of any of the aforementioned agents, KT6352 (Shiotsu Y. et al., *Exp. Hemat.* 1998, 26, 1195-1201), uteroferrin (Laurenz J C., et al. *Comp. Biochem. & Phys., Part A. Physiology.*, 1997, 116, 369-77), FK23 (Hasegawa T., et al. *Int. J. Immunopharm.*, 1996, 18 103-112) and other molecules identified as having anti-apoptotic, survival or proliferative properties for stem cells, progenitor cells, or other cells expressing Tpo Receptors.

In determining potency as TPO mimetics, the following assays were employed:

Luciferase Assay

Compounds of the present invention were tested for potency as mimetics of the TPO receptor in a Luciferase assay such as described in Lamb, et al., *Nucleic Acids Research* 23: 3283-3289 (1995) and Seidel, et al., *Proc. Natl. Acad. Sci., USA* 92: 3041-3045 (1995) by substituting a TPO-responsive BaF3 cell line (Vigon et al. *Proc. Natl. Acad. Sci. USA* 1992, 89, 5640-5644) for the HepG2 cells utilized therein. The murine BaF3 cells express TPO receptors and closely match the pattern of STAT (signal transducers and activators of transcription) activation observed in primary murine and human bone marrow cells.

Proliferation Assay

Some of the more preferred compounds of this invention were active in an in vitro proliferation assay using the human UT7TPO cell line. UT7TPO cells are a human megakaryoblastic cell line that express Tpo-R, whose survival and growth is dependent on the presence of TPO (Komatsu et al. *Blood* 1996, 87,4552).

Differentiation Assay

Likewise, some of the most preferred compounds of this invention were also positive in stimulating the maturation of megakaryocytes from human bone marrow cells. In this assay, purified human CD34+ progenitor cells were incubated in liquid culture with test compounds for 10 days and the number of cells expressing the transmembrane glycoprotein CD41 (gpIIb), a megakaryocytic marker, was then measured by flow cytometry (see Cwirla, S. E. et al Science, 1997, 276, 1696).

The pharmaceutically active compounds within the scope of this invention are useful as TPO mimetics in mammals, particularly humans, in need thereof.

Some of the preferred compounds within the scope of the invention showed activation from about 4% to 100% control at a concentration of 0.001-10 uM in the luciferase assay. The preferred compounds of the invention also promoted the proliferation of UT7TPO and 32D-mpl cells at a concentration of 0.003 to 30 uM. The preferred compounds of the invention also showed activity in the CD41 megakaryocytic assay at a concentration of 0.003 to 30 uM.

The present invention therefore provides a method of treating thrombocytopenia and other conditions with depressed platelet production, which comprises administering a compound of Formula (I) or a pharmaceutically acceptable salt, hydrate, solvate or ester thereof in a quantity effective to enhance platelet production. The compounds of Formula (I) also provide for a method of treating the above indicated disease states because of their demonstrated ability to act as TPO mimetics. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of a TPO mimetic, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular TPO mimetic in use, the strength of the preparation, the mode of administration, and the advancement of the disease condition. Additional factors depending on the particular patient being treated will result in a need to adjust dosages, including patient age, weight, diet, and time of administration.

The method of this invention of inducing TPO mimetic activity in mammals, including humans, comprises administering to a subject in need of such activity an effective TPO mimetic amount of a pharmaceutically active compound of the present invention.

The invention also provides for the use of a compound of Formula (I) in the manufacture of a medicament for use as a TPO mimetic.

The invention also provides for the use of a compound of Formula (I) in the manufacture of a medicament for use in therapy.

The invention also provides for the use of a compound of Formula (I) in the manufacture of a medicament for use in enhancing platelet production.

The invention also provides for the use of a compound of Formula (I) in the manufacture of a medicament for use in treating thrombocytopenia.

The invention also provides for a pharmaceutical composition for use as a TPO mimetic which comprises a compound of Formula (I) and a pharmaceutically acceptable carrier.

The invention also provides for a pharmaceutical composition for use in the treatment of thrombocytopenia which comprises a compound of Formula (I) and a pharmaceutically acceptable carrier.

The invention also provides for a pharmaceutical composition for use in enhancing platelet production which comprises a compound of Formula (I) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat thrombocytopenia, including chemotherapy-induced thrombocytopenia and bone marrow transplantation and other conditions with depressed platelet production, or compounds known to have utility when used in combination with a TPO mimetic.

Contemplated Equivalents—It will be appreciated by the person of ordinary skill in the art that the compounds of Formulas I and II may also exist in tautomeric forms. For example, in Formula I, the double bond that is drawn between the two nitrogen atoms exists between the lower nitrogen atom and the AR substituent. Tautomeric forms of the compounds of Formulas I and II are exemplified by the following Formula (IV):

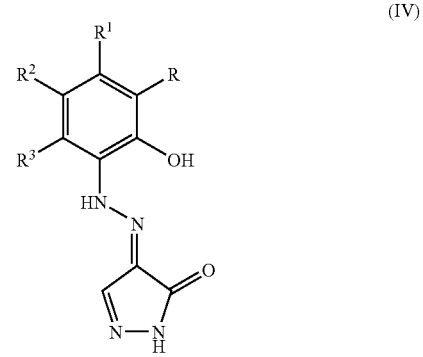

where the 'R' groups are as defined above. All such compounds are included in the scope of the invention and inherently included in the definition of the compounds of Formulas I and II.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

Example 1

4'-{N'-[1-(3,4-dimethylphenyl)-3-methyl-5-oxo-1,5-dihydropyrazol-4-ylidene]hydrazino}-3'-hydroxybiphenyl-4-carboxylic acid mp=280° C. (dec.). $^1$H NMR (300 MHz, d$_6$-DMSO) δ 13.62 (s, 1H), 13.2-12.2 (br s, 1H), 10.92 (s, 1H), 8.02 (d, J=8.2 Hz, 2H), 7.73-7.69 (m, 5H), 7.63 (d, 8.2 Hz, 1H), 7.31 (d, J=8.4 Hz, 1H), 7.29 (s, 1H), 7.19 (d, J=8.4 Hz, 1H), 2.30 (s, 3H), 2.26 (s, 3H), 2.2 (s, 3H); Anal. (C$_{25}$H$_{22}$N$_4$O$_4$.0.5H$_2$O) calcd: C, 66.51; H, 5.13; N, 12.41. found: C, 66.74; H, 5.08; N, 12.36.

Example 2

4'-{N'-[1-(3,4-dimethylphenyl)-3-methyl-5-oxo-1,5-dihydropyrazol-4-ylidene]hydrazino}-3'-hydroxybiphenyl-3-carboxylic acid mp 282° C. (dec.). $^1$H NMR (300 MHz, d$_6$-DMSO) δ 13.66 (s, 1H), 13.15 (s, 1H), 10.89 (s, 1H), 8.16 (s, 1H), 7.94 (d, J=7.7 Hz, 1H), 7.88 (d, J=7.9 Hz, 1H), 7.73-7.71 (m, 2H), 7.65-7.57 (m, 2H), 7.32-7.30 (m, 2H), 7.20 (d, J=8.3 Hz, 1H), 2.31 (s, 3H), 2.27 (s, 3H), 2.22 (s, 3H); Anal. (C$_{25}$H$_{22}$N$_4$O$_4$.0.25H$_2$O) calcd: C, 67.18; H, 4.97; N, 12.53. found: C, 67.26; H, 4.96; N, 12.46.

Example 3

3-{N'-[1-(3,4-dimethylphenyl)-3-methyl-5-oxo-1,5-dihydropyrazol-4-ylidene]hydrazino}-2'-hydroxybiphenyl-3-carboxylic acid;

mp 228° C. (dec.). $^1$H NMR (300 MHz, d$_6$-DMSO) δ 13.76 (s, 1H), 13.12 (s, 1H), 9.70 (s, 1H), 8.14 (s, 1H), 7.97 (dd, J=7.7 Hz, 1H), 7.81 (dd, J=7.7 Hz, 1H), 7.74-7.60 (m, 5H), 7.22-7.13 (m, 3H), 2.34 (s, 3H), 2.27 (s, 3H), 2.23 (s, 3H); Anal. (C$_{25}$H$_{22}$N$_4$O$_4$.1.0H$_2$O) calcd: C, 65.21; H, 5.25; N, 12.17. found: C, 65.60; H, 4.96; N, 12.04.

Example 4

3'-{N'-[1-(4-tert-butylphenyl)-3-methyl-5-oxo-1,5-dihydropyrazol-4-ylidene]hydrazino}-2'-hydroxybiphenyl-3-carboxylic acid;, hemihydrate mp 145° C. (dec.). $^1$H NMR (300 MHz, d$_6$-DMSO) δ 13.76 (s, 1H), 13.07 (s, 1H), 9.72 (s, 1H), 8.14 (s, 1H), 7.98 (dd, J=7.8, 1.2 Hz, 1H), 7.83 (t, J=8.7 Hz, 1H), 7.73 (dd, J=6.4, 3.1 Hz, 1H), 7.63 (t, J=7.7 Hz, 1H), 7.49 (d, J=7.8 Hz, 2H), 7.20-7.16 (m, 2H), 2.35 (s, 3H), 1.31 (s, 9H). Anal. (C$_{27}$H$_{26}$N$_4$O$_4$.0.5H$_2$O) calcd: C, 67.63; H, 5.67; N, 11.68. found: C, 67.53; H, 5.46; N, 11.66.

Example 5

2-Aza-3'-{N'-[1-(4-tert-butylphenyl)-3-methyl-5-oxo-1,5-dihydropyrazol-4-ylidene]hydrazino}-5'-chloro-2'-hydroxybiphenyl-3-carboxylic acid MS (ES) m/z 506 [M+H].

Example 6

2-Aza-3'-{N'-[1-(4-tert-butylphenyl)-3-methyl-5-oxo-1,5-dihydropyrazol-4-ylidene]hydrazino}-2'-hydroxybiphenyl-3-carboxylic acid MS (ES) m/z 472 (M+H)$^+$.

Example 7

3-Aza-3'-{N'-[1-(4-tert-butylphenyl)-3-methyl-5-oxo-1,5-dihydropyrazol-4-ylidene]hydrazino}-2'-hydroxybiphenyl-5-carboxylic acid $^1$H NMR (300 MHz, d$_6$-DMSO) δ 13.8 (br, 2H), 9.9 (s, 1H), 9.08 (s, 1H), 8.9 (s, 1H), 8.4 (s, 1H), 7.82 (d, J=7.7 Hz, 2H), 7.75 (d, J=7.9 Hz, 1H), 7.50 (d, J=7.0 Hz, 2H), 7.20 (m, 2H), 2.34 (s, 3H), 1.32 (s, 9H) MS (ES) m/z 472 (M+H)$^+$.

Example 8

2-Aza-5'-chloro-3'-{N'-[1-(3l4-dimethylphenyl)-3-methyl-5-oxo-1,5-dihydropyrazol-4-ylidene]hydrazino}-2'-hydroxybiphenyl-3-carboxylic acid $^1$H NMR (300 MHz, d$_6$-DMSO) δ 8.42 (d, J=9.2 Hz, 1H), 8.2 (t, J=8.0 Hz, 1H), 8.0 (m, 1H), 7.8 (s, 1H), 7.62 (m, 2H), 7.2 (d, J=9.2 Hz, 1H), 2.34 (s, 3H), 2.28 (s, 3H), 2.22 (s, 3H).

Example 9

2-Aza-3'-{N'-[1-(4-tert-butylphenyl)-3-methyl-5-oxo-1,5-dihydropyrazol-4-ylidene]hydrazino}-2'-hydroxy-5'-methylbiphenyl-3-carboxylic acid $^1$H NMR (300 MHz, d$_6$-DMSO) δ 8.25 (d, J=7.7 Hz, 1H), 8.15 (t, J=7.7 Hz, 1H), 7.9 (m, 3H), 7.78 (s, 1H), 7.58 (s, 1H), 7.5 (d, J=7.7 Hz, 2H), 2.36 (s, 3H), 2.35 (s, 3H), 1.23 (s, 9H).

Example 10

2-Aza-3'-{N'-[1-(3,4-dimethylphenyl)-3-methyl-5-oxo-1,5-dihydropyrazol-4-ylidene]hydrazino}-2'-hydroxy-5'-methylbiphenyl-3-carboxylic acid $^1$H NMR (300 MHz, d$_6$-DMSO) δ 8.45 (d, J=8.0 Hz, 1H), 8.25 (t, J=8.0 Hz, 1H), 8.05 (d, J=8.0 Hz, 1H), 7.85 (s, 1H), 7.78 (s, 1H), 7.68 (d, J=7.7 Hz, 1H), 7.62 (s, 1H), 7.22 (d, J=8.0 Hz, 1H), 2.36 (s, 3H), 2.35 (s, 3H), 2.28 (s, 3H), 2.25 (s, 3H).

Example 11

3'-{N'-[1-(4-tert-Butylphenyl)-3-methyl-5-oxo-1,5-dihydropyrazol-4-ylidene]hydrazino}-2'-hydroxy-5'-methylbiphenyl-3-carboxylic acid $^1$H NMR (300 MHz, d$_6$-DMSO) δ 8.13 (s, 1H), 7.95 (d, J=8.0 Hz, 1H), 7.82 (t, J=7.7 Hz, 2H), 7.72 (m, 2H), 7.61 (t, J=7.7 Hz, 2H), 7.53 (s, 1H), 7.5 (d, 8.0 Hz, 2H), 2.33 (s, 6H), 1.22 (s, 9H). MS (ES) m/z 485 (M+H)$^+$.

Example 12

3-{N'-[1-(3,4-dimethylphenyl)-3-methyl-5-oxo-1,5-dihydropyrazol-4-ylidene]hydrazino}-2-hydroxy-3'-(tetrazol-5-yl)biphenyl $^1$H NMR (300 MHz, d$_6$-DMSO) δ 13.7 (s, 1H), 9.8 (s, 1H), 8.26 (s, 1H), 8.1 (d, J=1.5 Hz, 1H), 7.75 (m, 3H), 7.6 (d, J=2.2 Hz, 1H), 7.2 (m, 3H), 2.35 (s, 3H), 2.25 (d, J=2.2 Hz, 6H).

Example 13

3'-{N'-[1-(3,4-dimethylphenyl)-3-methyl-5-oxo-1,5-dihydropyrazol-4-ylidene]hydrazino}-5'-fluoro-2'-hydroxybiphenyl-3-carboxylic acid $^1$H NMR (300 MHz, d$_6$-DMSO) δ 8.28 (s, 1H), 7.91 (m, 4H), 7.59 (t, J=8.0, 1H), 7.19 (m, 2H), 6.9 (dd, J=9.2, 3.4 Hz, 1H), 2.35 (s, 1H), 2.2 (s, 3H), 2.18 (s, 3H). MS (ES) m/z 461 [M+H].

Example 14

7-({N'-[1-(3,4-dimethylphenyl)-3-methyl-5-oxo-1,5-dihydropyrazol-4-ylidene]hydrazino}-2-hydroxyphenyl)quinolin-4[1H]-one-3-carboxylic acid $^1$H NMR (300 MHz, d$_6$-DMSO) δ 15.3 (s, 1H), 13.8 (s, 1H), 13.4 (s, 1H), 9.98 (s, 1H), 8.92 (d, J=6.6 Hz, 1H), 8.38 (d, J=8.5 Hz, 1H), 7.99 (s, 1H), 7.77 (m, 4H), 7.15 (m, 3H), 2.35 (s, 3H), 2.23 (s, 3H), 2.09 (s, 3H). MS (ES) m/z 510 [M+H].

Example 15

7-({N'-[1-(4-tert-butyl-phenyl)-3-methyl-5-oxo-1,5-dihydropyrazol-4-ylidene]hydrazino}-2-hydroxyphenyl)quinolin-4[1H]-one-3-carboxylic acid $^1$H NMR (300 MHz, d$_6$-DMSO) δ 8.68 (s, 1H), 8.43 (d, J=8.4 Hz, 1H), 7.68 (m, 5H), 7.48 (d, J=8.7 Hz, 1H), 7.10 (m, 2H), 2.4 (s, 3H), 1.34 (s, 9H).

Example 16

3-Aza-3'-{N'-[1-(3,4-dimethylphenyl)-3-methyl-5-oxo-1,5-dihydropyrazol-4-ylidene]hydrazino}-2'-hydroxybiphenyl-5-carboxylic acid $^1$H NMR (300 MHz, CDCl3) δ 9.16 (s, 1H), 8.9 (s, 1H), 8.5 (s, 1H), 7.7 (t, J=4.8 Hz, 1H), 7.6 (s, 1H), 7.58 (d, J=8.6 Hz, 1H), 7.18 (d, J=8.1 Hz, 1H), 7.13 (d, J=4.8 Hz, 1H), 2.4 (s, 3H), 2.31 (s, 3H), 2.27 (s, 3H), MS (ES) m/z 444 [M+H].

Example 17

3-Aza-3'-(N'-[1-{3-methyl-F4-(1-methylethyl)phenyl]-5-oxo-1,5-dihydropyrazol-4-ylidene}hydrazino)-2'-hydroxybiphenyl-5-carboxylic acid $^1$H NMR (300 MHz, CDCl$_3$) δ 13.7 (br s, 1H), 9.9 (s, 1H), 9.0 (s, 1H), 8.9 (s, 1H), 8.4 (s, 1H), 7.83 (d, J=7.6 Hz, 2H), 7.78 (d, J=7.8 Hz, 1H), 7.33 (d, J=8.6 Hz, 2H), 7.2 (m. 2H), 2.35 (s, 3H), 1.2 (d, J=6.7 Hz, 6H), MS (ES) m/z 458 [M+H].

Example 18

3-Aza-3'-{N'-[1-(3-tertbutylphenyl-3-methyl-5-oxo-1,5-dihydropyrazol-4-ylidene]hydrazino}-2'-hydroxybiphenyl-5-carboxylic acid $^1$H NMR (300 MHz, CDCl3) δ 13.7 (br s, 1H), 9.9 (s, 1H), 9.0 (s, 1H), 8.9 (s, 1H), 8.4 (s, 1H), 8.0 (s, 1H), 7.79 (dd, J=8.5 Hz, 1.9 Hz, 2H), 7.4 (t, J=7.9 Hz, 1H), 7.28 (m, 3H), 2.35 (s, 3H), 1.3 (s, 9H), MS (ES) m/z 472 [M+H].

Example 19

5'-Chloro-3'-{N'-[1-(3,4-dimethylphenyl)-3-methyl-5-oxo-1,5-dihydropyrazol-4-ylidene]hydrazino}-2'-hydroxybiphenyl-3-carboxylic acid;

$^1$H NMR (300 MHz, d$_6$-DMSO) δ 10.0 (s, 1H), 8.14 (s, 1H), 8.0 (d, J=8.0 Hz, 1H), 7.84 (d, J=8.0 Hz, 1H), 7.64 (m, 4H), 7.22 (d, J=8.1 Hz, 1H), 7.2 (s, 1H), 2.33 (s, 1H), 2.28 (s, 1H), 2.25 (s, 1H), MS (ES) m/z 477 [M+H].

Example 20

3'-{N'-[1-(3,4-Dimethylphenyl)-3,5-dioxo-1,5-dihydropyrazol-4-ylidene]hydrazino}-2'-hydroxybiphenyl-3-carboxylic acid MS m/e 445 [M+H]$^+$.

Example 21

3'-{N'-[1-(2-Ethoxy-2-oxoethyl)-3-methyl-5-oxo-1,5-dihydropyrazol-4-ylidene]hydrazino}-2'-hydroxybiphenyl-3-carboxylic acid;

MS (ES) m/z 425 (M+H).

Example 22

3-{N'-[1-(3,4-dimethylphenyl)-3-methyl-5-oxo-1,5-dihydropyrazol-4-ylidene]hydrazino}-2-hydroxy-4'-(tetrazol-5-yl)biphenyl $^1$H NMR (300 MHz, d$_6$-DMSO) δ 13.7 (br s, 1H), 9.7 (s, 1H), 8.15 (d, J=8.3 Hz, 2H), 7.84 (d, J=8.3 Hz, 2H), 7.73 (m, 2H), 7.64 (dd, J=2.3 Hz, 8.2 Hz, 1H), 7.24 (m, 3H), 2.35 (s, 3H), 2.27 (s, 3H), 2.23 (s, 3H). MS (ES) m/z 467 [M+H].

Example 23

3'-(N'-{1-[2-(N-tert-butyl)amino-2-oxoethyl]-3-methyl-5-oxo-1,5-dihydropyrazol-4-ylidene}hydrazino)-2'-hydroxybiphenyl-3-carboxylic acid MS (ES) m/z 452 (M+H)$^+$.

Example 24

3'-{N'-[3-Chloro-1-(3,4-dimethylphenyl)-5-oxo-1,5-dihydropyrazol-4-ylidene]hydrazino}-2'-hydroxybiphenyl-3-carboxylic acid;

mp=210° C. (dec.). MS m/e 463 [M+H]$^+$.

Example 25

5-chloro-3-{N'-[1-(3,4-dimethylphenyl)-3-methyl-5-oxo-1,5-dihydropyrazol-4-ylidene]hydrazino}-2-hydroxy-4'-(tetrazol-5-yl)biphenyl $^1$H NMR (300 MHz, d$_6$-DMSO) δ 13.6 (s, 1H), 8.15 (d, J=8.2 Hz, 2H), 7.84 (d, J=8.2 Hz, 2H), 7.69 (s, 1H), 7.64 (d, J=8.2 Hz, 1H), 7.24 (d, J=2.4 Hz, 1H), 7.23 (d, J=8.3 Hz, 1H), 2.35 (s, 3H), 2.27 (s, 3H), 2.23 (s, 3H). MS (ES) m/z 501 [M+H].

Example 26

3'-{N'-[1-(3,4-Dimethylphenyl)-3-methyl-5-oxo-1,5-dihydropyrazol-4-ylidene]hydrazino}-2'-hydroxybiphenyl-3,5-dicarboxylic acid $^1$H NMR (300 MHz, d$_6$-DMSO) δ 8.5 (s, 1H), 8.33 (s, 2H), 7.76 (m, 2H), 7.63 (d, J=8.0 Hz, 1H), 7.24 (m, 3H), 2.35 (s, 3H), 2.27 (s, 3H), 2.23 (s, 3H). MS (ES) m/z 487 [M+H].

Example 27

3-Aza-3'-{N'-[1-(3,4-dimethylphenyl)-3-methyl-5-oxo-1,5-dihydropyrazol-4-ylidene]hydrazino}-2'-hydroxy-5'-methylbiphenyl-5-carboxylic acid $^1$H NMR (300 MHz, CDCl3) δ 9.14 (s, 1H), 8.9 (s, 1H), 8.6 (s, 1H), 7.61 (d, J=9.2 Hz, 1H), 7.58 (d, J=7.3 Hz, 1H), 7.17 (d, J=8.1 Hz, 1H), 6.9 (s, 1H), 2.31 (s, 3H), 2.28 (s, 3H), 2.20 (s, 3H).

Example 28

3-{N'-[1-(3,4-Dimethylphenyl)-3-methyl-5-oxo-1,5-dihydropyrazol-4-ylidene]hydrazino}-2'-hydroxybiphenyl-4-carboxylic acid $^1$H NMR (300 MHz, d$_6$-DMSO) δ 13.7 (s, 1H), 12.9 (s, 1H), 9.7 (s, 1H), 8.06 (d, J=8.4 Hz, 1H), 7.75 (d, J=3.0 Hz, 1H), 7.69 (m, 3H), 7.65 (d, J=8.1 Hz, 1H), 7.18 (m, 3H), 2.33 (s, 3H), 2.27 (s, 3H), 2.23 (s, 3H). MS (ES) m/z 442 [M+H].

Example 29

3'-{N'-[1-(3,4-Dimethylphenyl)-3-methoxy-5-oxo-1,5-dihydropyrazol-4-ylidene]hydrazino}-2'-hydroxybiphenyl-3-carboxylic acid $^1$H NMR (300 MHz, d$_6$-DMSO) δ 13.7 (s, 1H), 13.1 (br s, 1H), 9.71 (s, 1H), 8.14 (s, 1H), 7.97 (dd, J=7.8, 1.4 Hz, 1H), 7.81 (d, J=8.1 Hz, 1H), 7.72 (s, 1H), 7.65-7.60 (m, 3H), 7.22-7.11 (m, 3H), 4.06 (s, 3H), 2.27 (s, 3H), 2.23 (s, 3H); Anal. (C$_{25}$H$_{22}$N$_4$O$_5$.0.66H$_2$O) calcd: C, 63.82; H, 5.00; N, 11.91. found: C, 63.53; H, 4.95; N, 11.49.

Example 30

3-{N'-[1-(4-methoxyphenyl)-3-methyl-5-oxo-1,5-dihydropyrazol-4-ylidene]hydrazino}-2'-hydroxybiphenyl-3-carboxylic acid $^1$H NMR (300 MHz, d$_6$-DMSO) δ 13.7 (s, 1H), 13.1 (br s, 1H), 9.70 (s, 1H), 8.14 (t, J=1.4 Hz, 1H), 7.97 (dt, J=7.9, 1.4 Hz, 1H), 7.84-7.60 (m, 5H), 7.19-7.15 (m, 2H), 7.04 (d, J=9.1 Hz, 2H), 3.79 (s, 3H), 2.34 (s, 3H); Anal. (C$_{24}$H$_{20}$N$_4$O$_5$.0.5H$_2$O; 0.5 CHCl$_3$) calcd: C, 57.35; H, 4.22; N, 10.91. found: C, 57.69; H, 4.35; N, 10.80.

Example 31

3-{N'-[1-(3,4-Dimethylphenyl)-3-methyl-5-oxo-1,5-dihydropyrazol-4-ylidene]hydrazino}-2-hydroxy-3'-trifluoromethanesulfonamidobiphenyl MS (ES) m/z 546 [M+H].

Example 32

3-{N'-[1-(3,4-Dichlorophenyl)-3-methyl-5-oxo-1,5-dihydropyrazol-4-ylidene]hydrazino}-2'-hydroxybiphenyl-3-carboxylic acid, $^1$H NMR (300 MHz, d$_6$-DMSO) δ 13.6 (s, 1H), 13.1 (s, 1H), 9.76 (s, 1H), 8.13 (m, 2H), 7.97 (d, J=7.5 Hz, 1H), 7.90 (d, J=8.9 Hz, 1H), 7.80 (d, J=7.5 Hz, 1H), 7.68-7.60 (m, 3H), 7.17-7.09 (m, 2H), 2.31 (s, 3H); Anal. (C$_{23}$H$_{16}$Cl$_2$N$_4$O$_4$.0.5H$_2$O) calcd: C, 56.11; H, 3.48; N, 11.38. found: C, 56.14; H, 3.47; N, 11.24.

Example 33

3'-{N'-[3-methyl-5-oxo-1-(3-trifluoromethylphenyl)-1,5-dihydropyrazol-4-ylidene]hydrazino}-2'-hydroxybiphenyl-3-carboxylic acid MS (ES) m/z 483 (M+H)$^+$.

Example 34

8-{N'-[1-(3,4-dimethylphenyl)-3-methyl-5-oxo-1,5-dihydropyrazol-4-ylidene]hydrazino}quinolin-4[1H]-one-3-carboxylic acid $^1$H NMR (300 MHz, d$_6$-DMSO) δ 8.31 (d, J=8.2 Hz, 1H), 8.2 (d, J=7.4 Hz, 1H), 8.09 (d, J=14.9 Hz, 1H), 7.82 (d, J=14.9 Hz, 1H), 7.6 (d, J=8.0 Hz, 1H), 7.56 (s, 1H), 7.42 (d, J=8.2 Hz, 1H), 7.25 (d, J=8.3 Hz), 2.46 (s, 3H), 2.28 (s, 3H), 2.25 (s, 2.25).

Example 35

3-{N'-[3-methyl-5-oxo-1-(4-trifluoromethylphenyl)-1,5-dihydropyrazol-4-ylidene]hydrazino}-2'-hydroxybiphenyl-3-carboxylic acid $^1$H NMR (300 MHz, d$_6$-DMSO) δ 13.7 (s, 1H), 13.1 (s, 1H), 9.78 (s, 1H), 8.18 (d, J=8.5 Hz, 2H), 8.14 (s, 1H), 7.98 (d, J=1.3 Hz, 1H), 7.85 (d, J=8.7 Hz, 2H), 7.8 (s, 1H), 7.75 (dd, J=7.3, 2.4, 1H), 7.64 (t, J=5.5, 1H), 7.2 (m, 2H), 2.37 (s, 3H).

Example 36

3-{N'-[3-methyl-5-oxo-1-(4-N-methylcarboxamidolphenyl)-1,5-dihydropyrazol-4-ylidene]hydrazino}-2'-hydroxybiphenyl-3-carboxylic acid $^1$H NMR (300 MHz, d$_6$-DMSO) δ 13.7 (brs, 1H), 9.77 (s, 1H), 8.46 (d, J=4.6 Hz, 1H), 8.14 (d, J=8.8 Hz, 1H), 7.95 (t, J=7.8 Hz, 2H), 7.85 (d, J=6.7 Hz, 1H), 7.75 (dd, J=7.9, 2.6 Hz, 1H), 7.64 (t, J=7.8 Hz, 1H), 7.2 (m, 2H), 2.78 (s, 3H), 2.28 (s, 3H). MS (ES) m/z 487 (M+H)⁺.

Example 37

N-[1-(3'-{N'-[1-(3,4-dimethylphenyl)-3-methyl-5-oxo-1,5-dihydropyrazol-4-ylidene]hydrazino}-2'-hydroxybiphenyl-3-yl)methanoyl]methanesulfonamide MS (ES) m/z 520 (M+H)⁺.

Example 38

3'-{N'-[3-methyl-5-oxo-1-phenyl-1,5-dihydropyrazol-4-ylidene]hydrazino}-2'-hydroxybiphenyl-3-carboxylic acid $^1$H NMR (300 MHz, d$_6$-DMSO) δ 14.9 (s, 1H), 8.21 (s, 1H), 8.04 (d, J=8.0 Hz, 2H), 7.9 (d, J=8.0 Hz, 1H), 7.78 (d, J=8.0, 1H), 7.54 (t, J=8.0 Hz, 1H), 7.34 (m, 3H), 7.0 (m, 3H), 2.34 (s, 3H).

Example 39

3'-{N'-[3-methyl-1-(4-methylphenyl)-5-oxo-1,5-dihydropyrazol-4-ylidene]hydrazino}-2'-hydroxybiphenyl-3-carboxylic acid $^1$H NMR (300 MHz, d$_6$-DMSO) δ 8.19 (s, 1H), 7.98 (d, J=8.0 Hz, 2H), 7.85 (d, J=8.0 Hz, 1H), 7.72 (d, J=8.0, 1H), 7.42 (t, J=8.0 Hz, 1H), 7.34 (d, J=8.0 Hz, 2H), 7.05 (d, J=8.0 Hz, 1H), 6.9 (t, J=8.0 Hz, 1H), 2.34 (s, 3H), 2.23 (s, 3H). MS (ES) m/z 429(M+H)⁺.

Example 40

3'-{N'-[1-(4-chlorophenyl)-3-methyl-5-oxo-1,5-dihydropyrazol-4-ylidene]hydrazino}-2'-hydroxybiphenyl-3-carboxylic acid $^1$H NMR (300 MHz, d$_6$-DMSO) δ 8.21 (s, 1H), 8.12 (d, J=8.0 Hz, 2H), 7.9 (d, J=8.0 Hz, 1H), 7.85 (d, J=8.0, 1H), 7.54 (t, J=8.0 Hz, 1H), 7.39 (m, 3H), 7.09 (m, 1H), 6.92 (t, J=8.0 Hz, 1H), 2.34 (s, 3H).

Example 41

3'-{N'-[1-(4-fluorophenyl)-3-methyl-5-oxo-1,5-dihydropyrazol-4-ylidene]hydrazino}-2'-hydroxybiphenyl-3-carboxylic acid $^1$H NMR (300 MHz, d$_6$-DMSO) δ 8.25 (s, 1H), 8.05 (d, J=7.5 Hz, 1H), 7.75 (dd, J=2.1 Hz, 8.2 Hz, 2H), 7.75 (m, 3H), 7.25 (m, 4H), 2.34 (s, 3H). MS (ES) m/z 457(M+H)⁺.

Example 42

3'-{N'-[3-methyl-5-oxo-1-(4-trifluoromethoxyphenyl)-1,5-dihydropyrazol-4-ylidene]hydrazino}-2'-hydroxybiphenyl-3-carboxylic acid $^1$H NMR (300 MHz, d$_6$-DMSO) δ 13.7 (br s, 1H), 13.1 (br s, 1H), 9.76 (br s, 1H), 8.1 (s, 1H), 8.05 (d, J=9.1 Hz, 2H), 7.97 (d, J=7.7 Hz, 1H), 7.8 (d, J=7.8 Hz, 1H), 7.75 (d, J=7.2 Hz, 1H), 7.65 (t, J=8.7 Hz, 1H), 7.47 (d, J=9 Hz, 2H), 7.18 (m, 2H), 2.35 (s, 3H). MS (ES) m/z 499(M+H)⁺.

Example 43

3'-{N'-[1-(3,4-dimethylphenyl)-3-ethoxy-5-oxo-1,5-dihydropyrazol-4-ylidene]hydrazino}-2'-hydroxybiphenyl-3-carboxylic acid $^1$H NMR (300 MHz, d$_6$-DMSO) δ 9.69 (s, 1H), 8.13 (s, 1H), 7.98 (d, J=7.6 Hz, 1H), 7.8 (d, J=8.4 Hz, 1H), 7.71 (s, 1H), 7.65 (m, 3H), 7.2 (m, 2H), 4.4 (m, 2H), 2.28 (s, 3H), 2.23 (s, 3H), 1.35 (t, J=8.6 Hz, 3H). MS (ES) m/z 473(M+H)⁺.

Example 44

3'-{N'-[1-(3,4-dimethylphenyl)-3-(1-methylethoxy)-5-oxo-1,5-dihydropyrazol-4-ylidene]hydrazino}-2'-hydroxybiphenyl-3-carboxylic acid $^1$H NMR (300 MHz, d$_6$-DMSO) δ 9.65 (s, 1H), 8.10 (s, 1H), 7.95 (d, J=7.7 Hz, 1H), 7.8 (d, J=8.1 Hz, 1H), 7.6 (s, 1H), 7.6 (m, 3H), 7.15 (m, 2H), 5.18 (m, 1H), 2.23 (s, 3H), 2.08 (s, 3H), 1.46 (s, 3H). 1.44 (s, 3H) MS (ES) m/z 487(M+H)⁺.

Example 45

3-{N'-[3-tert-butyl-1-(3,4-dimethylphenyl)-5-oxo-1,5-dihydropyrazol-4-ylidene]hydrazino}-2'-hydroxybiphenyl-3-carboxylic acid $^1$H NMR (300 MHz, CDCl$_3$) δ 8.22 (s, 1H), 8.08 (d, J=6.5 Hz, 1H), 7.78 (d, J=6.0 Hz, 1H), 7.7 (s, 1H), 7.63 (dd, J=2.6 Hz, 7.1 Hz, 2H), 7.56 (t, J=7.8 Hz, 1H), 7.1 (m, 3H), 2.31 (s, 3H), 2.27 (s, 3H), 1.5 (s, 9H). MS (ES) m/z 485(M+H)⁺.

Example 46

3'-{N'-[3-methyl-1-(4-methyl-2,3,5,6-tetrafluorophenyl)-5-oxo-1,5-dihydropyrazol-4-ylidene]hydrazino}-2'-hydroxybiphenyl-3-carboxylic acid $^1$H NMR (300 MHz, d$_6$-DMSO) δ 13.4 (br s, 1H), 9.78 (s, 1H), 7.98 (d, J=6.4 Hz, 1H), 7.8 (d, J=6.4 Hz, 1H), 7.75 (dd, J=2.2 Hz, 7.4 Hz, 1H), 7.61 (t, J=7.7 Hz, 1H), 7.19 (m, 2H), 2.33 (s, 6H).

Example 47

3'-{N'-[1-(4-fluoro-3-methylphenyl)-3-methyl-5-oxo-1,5-dihydropyrazol-4-ylidene]hydrazino}-2'-hydroxybiphenyl-3-carboxylic acid $^1$H NMR (300 MHz, d$_6$-DMSO) δ 13.7 (br s, 1H), 13.0 (s, 1H), 9.8 (s, 1H), 8.15 (s, 1H), 7.97 (d, J=7.7 Hz, 1H), 7.75 (m, 4H), 7.63 (t, J=7.7 Hz, 1H), 7.2 (m, 3H), 2.34 (s, 3H), 2.30 (s, 3H). MS (ES) m/z 445 (M+H)⁺.

Example 48

3'-{N'-[1-(3,4-dimethylphenyl)-3-phenyl-5-oxo-1,5-dihydropyrazol-4-ylidene]hydrazino}-2'-hydroxybiphenyl-3-carboxylic acid $^1$H NMR (300 MHz, d$_6$-DMSO) δ 9.80 (br s, 1H), 8.08 (d, J=8.4 Hz, 2H), 8.16 (s, 1H), 7.98 (d, J=7.5 Hz, 1H), 7.8 (m, 3H), 7.6 (m, 4H), 7.25 (m, 3H), 2.31 (s, 3H), 2.26 (s, 3H), MS (ES) m/z 505 (M+H)⁺.

Example 49

3-{N'-[1-(3,4-dimethylphenyl)-5-oxo-3-phenyl-1,5-dihydropyrazol-4-ylidene]hydrazino}-2-hydroxy-3'-tetrazol-5-ylbiphenyl MS (ES) m/z 529(M+H)$^+$.

Example 50

3-{N'-[1-(3,4-dimethylphenyl)-3-methoxy-5-oxo-1,5-dihydropyrazol-4-ylidene]hydrazino}-2-hydroxy-3'-tetrazol-5-ylbiphenyl MS (ES) m/z 483(M+H)$^+$.

Example 51

3-{N'-[1-(3,4-dimethylphenyl)-3-ethoxy-5-oxo-1,5-dihydropyrazol-4-ylidene]hydrazino}-2-hydroxy-3'-tetrazol-5-ylbiphenyl $^1$H NMR (300 MHz, d$_6$-DMSO) δ 9.79 (br s, 1H), 8.08 (d, J=7.4 Hz, 1H), 7.7 (m, J=7.7 Hz, 5H), 7.2 (m, 3H), 4.4 (m, 2H), 2.27 (s, 3H), 2.23 (s, 3H), 1.47 (t, J=7.0 Hz. 3H), MS (ES) m/z 497(M+H)$^+$

Example 52

3-{N'-[1-(3,4-dimethylphenyl)-3-(1-methylethoxy)-5-oxo-1,5-dihydropyrazol-4-ylidene]hydrazino}-2-hydroxy-3'-tetrazol-5-ylbiphenyl MS (ES) m/z 511(M+H)$^+$.

Example 53

3-{N'-[1-(4-fluorophenyl)-3-methyl-5-oxo-1,5-dihydropyrazol-4-ylidene]hydrazino}-2-hydroxy-3'-tetrazol-5-ylbiphenyl $^1$H NMR (300 MHz, d$_6$-DMSO) δ 8.2 (s, 1H), 8.08 (d, J=7.4 Hz, 1H), 7.95 (dd, J=2.1 Hz, 9.2 Hz, 2H), 7.75 (m, 3H), 7.2 (m, 4H), 2.34 (s, 3H). MS (ES) m/z 457(M+H)$^+$.

Example 54

3-{N'-[1-(4-fluoro-3-methylphenyl)-3-methyl-5-oxo-1,5-dihydropyrazol-4-ylidene]hydrazino}-2-hydroxy-3'-tetrazol-5-ylbiphenyl $^1$H NMR (300 MHz, d$_6$-DMSO) δ 13.7 (br s, 1H), 9.9 (br s, 1H), 8.2 (s, 1H), 8.09 (d, J=7.5 Hz, 1H), 7.8 (m, 5H), 7.25 (m, 3H), 2.35 (s, 3H), 2.30 (s, 3H). MS (ES) m/z 471(M+H)$^+$.

Example 55

3-{N'-[3-methyl-5-oxo-1-(4-trifluoromethylphenyl)-1,5-dihydropyrazol-4-ylidene]hydrazino}-2-hydroxy-3'-tetrazol-5-ylbiphenyl $^1$H NMR (300 MHz, d$_6$-DMSO) δ 13.7 (br s, 1H), 9.9 (br s, 1H), 8.25 (s, 1H), 8.17 (d, J=8.6 Hz, 2H), 8.08 (s, J=6.4 Hz, 1H), 7.85 (d, J=8.8 Hz, 2H), 7.76 (m, 3H), 7.25 (m, 2H), 2.38 (s, 3H). MS (ES) m/z 505 (M+H)$^+$.

Example 56

3'-{N'-[1-(3,4-dimethylphenyl)-3-(pyridin-4-yl-5-oxo-1,5-dihydropyrazol-4-ylidene]hydrazino}-2'-hydroxybiphenyl-3-carboxylic acid $^1$H NMR (300 MHz, d$_6$-DMSO) δ 14.4 (br s, 1H), 8.9 (s, 2H), 8.5 (s, 2H), 8.19 (s, 1H), 7.98 (d, J=8.7 Hz, 1H), 7.90 (d, J=7.3 Hz, 1H), 7.8 (m, 2H), 7.75 (d, J=7.3 Hz, 1H), 7.65 (t, J=8.7 Hz, 1H), 7.25 (m, 3H), 2.29 (s, 3H), 2.26 (s, 3H). MS (ES) m/z 506(M+H)$^+$.

Example 57

3-{N'-[1-(3,4-dimethylphenyl)-3-pyridin-4-yl-5-oxo-1,5-dihydropyrazol-4-ylidene]hydrazino}-2-hydroxy-3'-tetrazol-5-ylbiphenyl $^1$H NMR (300 MHz, d$_6$-DMSO) δ 14.4 (br s, 1H), 10.1 (br s, 1H), 8.9 (s, 2H), 8.65 (s, 2H), 8.3 (s, 1H), 8.13 (d, J=7.4 Hz, 1H), 7.8 (m, 6H), 7.32 (m, 3H), 2.28 (s, 3H), 2.23 (s, 3H). MS (ES) m/z 530(M+H)$^+$.

Example 58

3-{N'-[1-(3,4-dimethylphenyl)-3-pyridin-2-yl-5-oxo-1,5-dihydropyrazol-4-ylidene]hydrazino}-2-hydroxy-3'-tetrazol-5-ylbiphenyl $^1$H NMR (300 MHz, d$_6$-DMSO) δ 8.9 (br s, 1H), 8.43 (br s, 1H), 8.29 (s, 1H), 8.15 (d, J=8.1 Hz, 2H), 7.80 (m, 5H), 7.65 (m, 1H), 7.23 (m, 3H), 2.29 (s, 3H), 2.26 (s, 3H). MS (ES) m/z 530(M+H)$^+$.

Example 59

3'-{N'-[1-(3,4-dimethylphenyl)-3-(pyridin-2-yl-5-oxo-1,5-dihydropyrazol-4-ylidene]hydrazino}-2'-hydroxybiphenyl-3-carboxylic acid $^1$H NMR (300 MHz, d$_6$-DMSO) δ 9.8 (br s, 1H), 8.9 (s, 1H), 8.49 (d, J=8.1 Hz, 1H), 8.19 (s, 2H), 7.98 (d, J=8.1 Hz, 1H), 7.80 (m, 4H), 7.75 (t, J=7.0 Hz, 2H), 7.1 (m, 3H), 2.29 (s, 3H), 2.26 (s, 3H). MS (ES) m/z 506(M+H)$^+$.

Example 60

3-{N'-[1-(3-Fluoro-4-methylphenyl)-3-methyl-5-oxo-1,5-dihydropyrazol-4-ylidene]hydrazino}-2-hydroxy-3'-tetrazol-5-ylbiphenyl $^1$H NMR (300 MHz, d$_6$-DMSO) δ 13.7 (br s, 1H), 9.9 (br s, 1H), 8.26 (s, 1H), 8.09 (d, J=7.4 Hz, 1H), 7.7 (m, 5H), 7.38 (t, J=8.3 Hz, 1H), 7.23 (m, 2H), 2.35 (s, 3H), 2.24 (s, 3H). MS (ES) m/z 471(M+H)$^+$.

Example 61

3'-{N'-[1-(3-fluoro-4-methylphenyl)-3-methyl-5-oxo-1,5-dihydropyrazol-4-ylidene]hydrazino}-2'-hydroxybiphenyl-3-carboxylic acid;

$^1$H NMR (300 MHz, d$_6$-DMSO) δ 13.7 (br s, 1H), 13.1 (br s, 1H), 9.9 (br s, 1H), 8.13 (s, 1H), 7.97 (d, J=7.8 Hz, 1H), 7.8 (d, J=7.8 Hz, 1H), 7.72 (m, 3H), 7.38 (t, J=8.3 Hz, 1H), 7.18 (m, 2H), 2.35 (s, 3H), 2.24 (s, 3H). MS (ES) m/z 447(M+H)$^+$.

Example 62

3'-{N'-[3-methyl-5-oxo-1-(4-trifluoromethylpyrimidin-2-yl)-1,5-dihydropyrazol-4-ylidene]hydrazino}-2'-hydroxybiphenyl-3-carboxylic acid MS (ES) m/z 485 (M+H)$^+$.

Example 63

3'-N-tert-butoxycarbonylamino-3-{N'-[1-(3,4-Dimethylphenyl)-3-methyl-5-oxo-1,5-dihydropyrazol-4-ylidene]hydrazino}-2-hydroxybiphenyl MS (ES) m/z 514 (M+H)$^+$.

Example 64

3'-amino-3-{N'-[1-(3,4-dimethylphenyl)-3-methyl-5-oxo-1,5-dihydropyrazol-4-ylidene]hydrazino}-2-hydroxybiphenyl MS (ES) m/z 414 (M+H)$^+$.

Example 65

3-{N'-[1-(3-fluorophenyl)-3-methyl-5-oxo-1,5-dihydropyrazol-4-ylidene]hydrazino}-2-hydroxy-3'-tetrazol-5-ylbiphenyl $^1$H NMR (300 MHz, d$_6$-DMSO) δ 13.7 (br s, 1H), 8.2 (s, 1H), 8.08 (d, J=8.5 Hz, 1H), 7.8 (m, 5H), 7.53 (m, 1H), 7.21 (m, 2H), 7.08 (t, J=7.8 Hz, 1H), 2.37 (s, 3H). MS (ES) m/z 457(M+H)$^+$.

Example 66

3'-{N'-[1-(3-fluorophenyl)-3-methyl-5-oxo-1,5-dihydropyrazol-4-ylidene]hydrazino}-2'-hydroxybiphenyl-3-carboxylic acid $^1$H NMR (300 MHz, d$_6$-DMSO) δ 13.7 (br s, 1H), 9.7 (s, 1H), 8.14 (s, 1H), 7.97 (d, J=7.7 Hz, 1H), 7.8 (m, 4H), 7.64 (t, J=7.7 Hz, 1H), 7.52 (m, 1H), 7.2 (m, 2H), 7.07 (t, J=7.2, 1H), 2.35 (s, 3H). MS (ES) m/z 433(M+H)$^+$.

Example 67

3-{N'-[3-methyl-5-oxo-1-(2,3,4,5,6-pentafluorophenyl)-1,5-dihydropyrazol-4-ylidene]hydrazino}-2-hydroxy-3'-tetrazol-5-ylbiphenyl $^1$H NMR (300 MHz, d$_6$-DMSO) δ 9.9 (s, 1H), 8.2 (s, 1H), 8.07 (d, J=7.3 Hz, 1H), 7.76 (m, 3H), 7.23 (m, 2H), 2.34 (s, 3H). MS (ES) m/z 529(M+H)$^+$.

Example 68

3'-{N'-[3-methyl-5-oxo-1-(2,3,4,5,6-pentafluorophenyl)-1,5-dihydropyrazol-4-ylidene]hydrazino}-2'-hydroxybiphenyl-3-carboxylic acid $^1$H NMR (300 MHz, d$_6$-DMSO) δ 9.8 (s, 1H), 8.12 (s, 1H), 7.98 (d, J=7.9 Hz, 1H), 7.79 (d, J=7.7 Hz, 1H), 7.76 (d, J=7.5 Hz, 1H), 7.61 (t, J=7.8 Hz, 1H), 7.2 (m, 2H), 2.34 (s, 3H). MS (ES) m/z 505(M+H)$^+$.

Example 69

3'-{N'-[1-(3,4-difluorophenyl)-3-methyl-5-oxo-1,5-dihydropyrazol-4-ylidene]hydrazino}-2'-hydroxybiphenyl-3-carboxylic acid $^1$H NMR (300 MHz, d$_6$-DMSO) δ 13.6 (br s, 1H), 13.1 (br s, 1H), 9.9 (br s, 1H), 8.1 (s, 1H), 7.96 (d, J=7.8 Hz, 1H), 7.94 (dd, J=7.5 Hz, 2.4 Hz, 1H), 7.76 (m, 3H), 7.62 (t, J=7.8 Hz, 1H), 7.55 (m, 1H), 7.19 (m, 2H), 2.34 (s, 3H). MS (ES) m/z 451(M+H)$^+$.

Example 70

3'-{N'-[1-(3,4-dimethylphenyl)-3-methoxymethyl-5-oxo-1,5-dihydropyrazol-4-ylidene]hydrazino}-2'-hydroxybiphenyl-3-carboxylic acid $^1$H NMR (300 MHz, d$_6$-DMSO) δ 13.9 (br s, 1H), 13.1 (br s, 1H), 9.9 (br s, 1H), 8.1 (s, 1H), 7.96 (d, J=7.7 Hz, 1H), 7.81 (d, J=6.5 Hz, 1H), 7.71 (s, 1H), 7.65 (m, 3H), 7.2 (m, 3H), 4.5 (s, 2H), 3.4 (s, 3H), 2.28 (s, 3H), 2.24 (s, 3H). MS (ES) m/z 473(M+H)$^+$.

Example 71

3-{N'-[1-(3,4-dimethylphenyl)-3-methoxymethyl-5-oxo-1,5-dihydropyrazol-4-ylidene]hydrazino}-2-hydroxy-3'-tetrazol-5-ylbiphenyl $^1$H NMR (300 MHz, d$_6$-DMSO) δ 13.9 (br s, 1H), 9.9 (s, 1H), 8.25 (s, 1H), 8.09 (d, J=7.4 Hz, 1H), 7.78 (m, 3H), 7.71 (s, 1H), 7.65 (dd, J=2.1 Hz and 7.2 Hz, 1H), 7.25 (m, 3H), 4.5 (s, 2H), 3.4 (s, 3H), 2.28 (s, 3H), 2.24 (s, 3H). MS (ES) m/z 497(M+H)$^+$.

Example 72

3-{N'-[1-(3,4-difluorophenyl)-3-methyl-5-oxo-1,5-dihydropyrazol-4-ylidene]hydrazino}-2-hydroxy-3'-tetrazol-5-ylbiphenyl $^1$H NMR (300 MHz, d$_6$-DMSO) δ 8.25 (s, 1H), 8.1 (d, J=7.3 Hz, 1H), 7.95 (m, 1H), 7.78 (m, 4H), 7.58 (m, 1H), 7.22 (m, 2H), 2.37 (s, 3H). MS (ES) m/z 475(M+H)$^+$.

Example 73

3'-{N'-[1-(3,4-dimethylphenyl)-5-oxo-3-trifluoromethyl-1,5-dihydropyrazol-4-ylidene]hydrazino}-2'-hydroxybiphenyl-3-carboxylic acid $^1$H NMR (300 MHz, d$_6$-DMSO) δ 13.1 (br s, 1H), 10.1 (br s, 1H), 8.1 (s, 1H), 7.98 (d, J=7.6 Hz, 1H), 7.82 (d, J=7.7 Hz, 1H), 7.6 (m, 3H), 7.27 (m, 2H), 7.55 (m, 1H), 7.2 (t, J=7.8 Hz, 1H), 2.30 (s, 3H), 2.26 (s, 3H). MS (ES) m/z 497(M+H)$^+$.

Example 74

3-{N'-[1-(3,4-dimethylphenyl)-3-methyl-5-oxo-1,5-dihydropyrazol-4-ylidene]hydrazino}-6-fluoro-2'-hydroxybiphenyl-3-carboxylic acid;

$^1$H NMR (300 MHz, d$_6$-DMSO) δ 13.7 (br s, 1H), 13.1 (br s, 1H), 9.8 (s, 1H), 8.08 (m, 2H), 7.78 (dd, J=7.0 Hz, 2.8 Hz, 1H), 7.71 (s, 1H), 7.65 (dd, J=2.1 Hz, 8.1 Hz, 1H), 7.46 (t,

J=8.8 Hz, 1H), 7.21 (d, J=8.3 Hz, 1H), 7.14 (m, 2H), 2.34 (s, 3H), 2.27 (s, 3H), 2.23 (s, 3H). MS (ES) m/z 461(M+H)$^+$.

Example 75

3'-{N'-[1-(3,4-dimethylphenyl)-5-oxo-3-propyl-1,5-dihydropyrazol-4-ylidene]hydrazino}-2'-hydroxybiphenyl-3-carboxylic acid $^1$H NMR (300 MHz, d$_6$-DMSO) δ 13.7 (br s, 1H), 9.7 (s, 1H), 8.14 (s, 1H), 7.97 (d, J=7.8 Hz, 1H), 7.8 (d, J=7.8 Hz, 1H), 7.62 (m, 4H), 7.62 (m, 3H), 2.7 (t, J=7.5 Hz, 2H), 2.28 (s, 3H), 2.24 (s, 3H), 1.8 (m, 2H), 1.1 (t, J=7.4 Hz, 3H).

Example 76

3-{N'-[1-(3,4-dimethylphenyl)-5-oxo-3-propyl-1,5-dihydropyrazol-4-ylidene]hydrazino}-2-hydroxy-3'-tetrazol-5-ylbiphenyl $^1$H NMR (300 MHz, d$_6$-DMSO) δ 8.27 (s, 1H), 8.08 (d, J=7.4 Hz, 1H), 7.78 (m, 3H), 7.65 (d, J=8.2 Hz, 1H), 7.18 (m, 4H), 2.7 (t, J=7.5 Hz, 2H), 2.27 (s, 3H), 2.23 (s, 3H), 1.8 (m, 2H), 1.03 (t, J=7.4 Hz, 3H). MS (ES) m/z 495(M+H)$^+$.

Example 77

3'-{N'-[1-(3,4-dimethylphenyl)-3-(1-methyl-1H-pyrrol-3-yl)-5-oxo-1,5-dihydropyrazol-4-ylidene]hydrazino}-2'-hydroxybiphenyl-3-carboxylic acid $^1$H NMR (300 MHz, d$_6$-DMSO) δ 14.0 (br s, 1H), 9.6 (s, 1H), 8.15 (s, 1H), 7.95 (d, J=8.4 Hz, 1H), 7.82 (m, 3H), 7.72 (dd, J=2.1 Hz and 8.1 Hz, 1H), 7.63 (m, 2H), 7.23 (m, 3H), 6.89 (t, J=2.5 Hz, 1H), 6.68 (d, J=2.8 Hz, 1H), 3.89 (s, 3H), 2.29 (s, 3H), 2.24 (s, 3H). MS (ES) m/z 508(M+H)$^+$.

Example 78

3-{N'-[1-(3,4-dimethylphenyl)-3-(1-methyl-1H-pyrrol-3-yl)-5-oxo-1,5-dihydropyrazol-4-ylidene]hydrazino}-2-hydroxy-3'-tetrazol-5-ylbiphenyl $^1$H NMR (300 MHz, d$_6$-DMSO) δ 14.0 (br s, 1H), 9.7 (s, 1H), 8.26 (s, 1H), 8.1 (d, J=7.5 Hz, 1H), 7.85 (t, J=5.0 Hz, 1H), 7.82 (s, 1H), 7.75 (m, 3H), 7.62 (s, 1H), 7.24 (s, 3H), 6.9 (s, 1H), 6.7 (s, 1H), 3.89 (s, 3H), 2.29 (s, 3H), 2.24 (s, 3H). MS (ES) m/z 532(M+H)$^+$.

Example 79

3'-{N'-[1-(3,4-dimethylphenyl)-3-furan-2-yl-5-oxo-1,5-dihydropyrazol-4-ylidene]hydrazino}-2'-hydroxybiphenyl-3-carboxylic acid;

$^1$H NMR (300 MHz, d$_6$-DMSO) δ 14.0 (s, 1H), 9.8 (s, 1H), 8.55 (s, 1H), 8.15 (s, 1H), 7.95 (m, 2H), 7.82 (m, 2H), 7.71 (dd, J=2.0 Hz and 8.0 Hz, 1H), 7.63 (t, J=7.7 Hz, 1H), 7.23 (m, 3H), 7.1 (s, 1H), 2.3 (s, 3H), 2.2 (s, 3H). MS (ES) m/z 495(M+H)$^+$.

Example 80

3-{N'-[1-(3,4-dimethylphenyl)-3-furan-2-yl-5-oxo-1,5-dihydropyrazol-4-ylidene]hydrazino}-2-hydroxy-3'-tetrazol-5-ylbiphenyl $^1$H NMR (300 MHz, d$_6$-DMSO) δ 14.0 (s, 1H), 9.8 (s, 1H), 8.56 (s, 1H), 8.26 (s, 1H), 8.1 (d, J=7.5 Hz, 1H), 7.96 (dd, J=2.0 Hz and 7.7 Hz, 1H), 7.9 (s, 1H), 7.75 (m, 4H), 7.25 (m, 3H), 7.1 (s, 1H), 2.3 (s, 3H), 2.2 (s, 3H). MS (ES) m/z 495(M+H)$^+$.

Example 81

N-(2'-hydroxy-3'-{N'-[3-methyl-5-oxo-1-(4-trifluoromethyl-phenyl)-1,5-dihydro-pyrazol-4-ylidene]hydrazino}biphenyl-3-yl)-1,1,1-trifluoromethanesulfonamide $^1$H NMR (300 MHz, d$_6$-DMSO) δ 13.7 (s, 1H), 9.8 (s, 1H), 8.19 (d, J=8.6 Hz, 2H), 7.8 (d, J=9.0 Hz, 2H), 7.7 (d, J=2.8 Hz and 6.9 Hz, 1H), 7.5 (m, 3H), 7.3 (d, J=6.0 Hz, 1H), 7.15 (m, 2H), 2.35 (s, 3H). MS (ES) m/z 586(M+H)$^+$.

Example 82

N-(2'-hydroxy-3'-{N'-[1-(3-fluoro-4-methylphenyl)-3-methyl-5-oxo-1,5-dihydro-pyrazol-4-ylidene]hydrazino}biphenyl-3-yl)-1,1,1-trifluoromethanesulfonamide $^1$H NMR (300 MHz, d$_6$-DMSO) δ 13.7 (s, 1H), 9.8 (s, 1H), 7.7 (m, 3H), 7.54 (t, d=7.8 Hz, 1H), 7.5 (d, J=7.8 Hz, 1H), 7.37 (t, J=8.3 Hz, 1H), 7.3 (d, J=6.0 Hz, 1H), 7.15 (m, 2H), 2.35 (s, 3H), 2.3 (s, 3H). MS (ES) m/z 550(M+H)$^+$.

Example 83

N-(2'-hydroxy-3'-{N'-[1-(4-fluoro-3-methylphenyl)-3-methyl-5-oxo-1,5-dihydro-pyrazol-4-ylidene]hydrazino}biphenyl-3-yl)-1,1,1-trifluoromethanesulfonamide $^1$H NMR (300 MHz, d$_6$-DMSO) δ 13.7 (s, 1H), 9.8 (s, 1H), 7.83 (dd, J=1.8 Hz and 7.5 Hz, 1H), 7.75 (m, 1H), 7.73 (dd, J=2.0 and 7.8 Hz, 1H), 7.53 (t, d=7.8 Hz, 1H), 7.45 (m, 2H), 7.2 (m, 5H), 2.35 (s, 3H), 2.3 (s, 3H). MS (ES) m/z 550(M+H)$^+$.

Example 84

N-(2'-hydroxy-3'-{N'-[1-(3,4-difluorophenyl)-3-methyl-5-oxo-1,5-dihydro-pyrazol-4-ylidene]hydrazino}biphenyl-3-yl)-1,1,1-trifluoromethanesulfonamide $^1$H NMR (300 MHz, d$_6$-DMSO) δ 13.7 (s, 1H), 9.8 (s, 1H), 7.98 (m, 1H), 7.78 (m, 1H), 7.73 (dd, J=2.7 and 7.0 Hz, 1H), 7.53 (m, 4H), 7.3 (d, J=5.6 Hz, 1H), 7.18 (m, 2H), 2.35 (s, 3H). MS (ES) m/z 554(M+H)$^+$.

Example 85

N-(3'-{N'-[1-(3,4-dimethylphenyl)-3-methyl-5-oxo-1,5-dihydropyrazol-4-ylidene]hydrazino}-2'-hydroxybiphenyl-3-yl)guanidine MS (ES) m/z 456(M+H)$^+$.

Example 86

3'-{N'-[1-(3,4-dimethylphenyl)-3-ethyl-5-oxo-1,5-dihydropyrazol-4-ylidene]hydrazino}-2'-hydroxybiphenyl-3-carboxylic acid $^1$H NMR (300 MHz, d$_6$-DMSO) δ 13.8 (s, 1H), 9.7 (s, 1H), 8.14 (s, 1H), 7.98 (d, J=7.7 Hz, 1H), 7.83 (d, J=7.7 Hz, 1H), 7.65 (m, 5H), 7.1 (m, 3H), 2.5 (m, 2H), 2.27 (s, 3H), 2.23 (s, 3H), 1.3 (t, J=7.5 Hz, 3H). MS (ES) m/z 457(M+H)$^+$.

Example 87

3-{N'-[1-(3,4-dimethylphenyl)-3-ethyl-5-oxo-1,5-dihydropyrazol-4-ylidene]hydrazino}-2-hydroxy-3'-tetrazol-5-ylbiphenyl $^1$H NMR (300 MHz, d$_6$-DMSO) δ 13.8 (s, 1H), 9.8 (s, 1H), 8.25 (s, 1H), 8.09 (d, J=7.5 Hz, 1H), 7.76 (m, 4H), 7.65 (d, J=7.2 Hz, 1H), 7.22 (m, 3H), 2.5 (m, 2H), 2.28 (s, 3H), 2.24 (s, 3H), 1.3 (t, J=7.5 Hz, 3H).

Example 88

3'-{N'-[1-(3,4-dimethylphenyl)-5-oxo-3-thien-2-yl-1,5-dihydropyrazol-4-ylidene]hydrazino}-2'-hydroxybiphenyl-3-carboxylic acid $^1$H NMR (300 MHz, d$_6$-DMSO) δ 14.0 (s, 1H), 9.8 (s, 1H), 8.14 (s, 1H), 8.01 (d, J=3.7 Hz, 1H), 7.97 (d, J=7.8 Hz, 1H), 7.82 (m, 4H), 7.65 (m, 2H), 7.25 (m, 4H), 2.29 (s, 3H), 2.24 (s, 3H). MS (ES) m/z 511 (M+H)$^+$.

Example 89

3-{N'-[3-cyclopropyl-1-(3,4-dimethylphenyl)-5-oxo-1,5-dihydropyrazol-4-ylidene]hydrazino}-2'-hydroxybiphenyl-3-carboxylic acid $^1$H NMR (300 MHz, d$_6$-DMSO) δ 13.8 (s, 1H), 9.7 (s, 1H), 8.14 (s, 1H), 7.99 (d, J=7.9 Hz, 1H), 7.8 (d, J=7.9 Hz, 1H), 7.7 (m, 4H), 7.01 (m, 3H), 2.27 (s, 3H), 2.23 (s, 3H), 2.16 (m, 1H), 1.19 (m, 2H), 1.18 (m, 2H). MS (ES) m/z 469(M+H)$^+$.

Example 90

3'-{N'-[1-(3,4-dimethylphenyl)-5-oxo-3-thiazol-2-yl-1,5-dihydropyrazol-4-ylidene]hydrazino}-2'-hydroxybiphenyl-3-carboxylic acid $^1$H NMR (300 MHz, d$_6$-DMSO) δ 13.0 (br s, 1H), 9.7 (s, 1H), 8.16 (s, 1H), 7.99 (m, 2H), 7.7 (m, 5H), 7.2 (m, 3H), 2.27 (s, 3H), 2.23 (s, 3H). MS (ES) m/z 512(M+H)$^+$.

Example 91

3-{N'-[1-(3,4-dimethylphenyl)-5-oxo-1,5-dihydropyrazol-4-ylidene]hydrazino}-2'-hydroxybiphenyl-3-carboxylic acid $^1$H NMR (300 MHz, d$_6$-DMSO) δ 8.19 (s, 1H), 8.1 (s, 1H), 7.9 (d, J=7.5 Hz, 1H), 7.8 (d, J=7.5 Hz, 1H), 7.65 (m, 3H), 7.2 (m, 3H), 2.27 (s, 3H), 2.23 (s, 3H). MS (ES) m/z 429(M+H)$^+$.

Example 92

3-{N'-[1-(3,4-dimethylphenyl)-3-(1-methylethyl)-5-oxo-1,5-dihydropyrazol-4-ylidene]hydrazino}-2'-hydroxybiphenyl-3-carboxylic acid $^1$H NMR (300 MHz, d$_6$-DMSO) δ 13.8 (s, 1H), 9.6 (s, 1H), 8.14 (s, 1H), 8.1 (s, 1H), 7.97 (d, J=7.7 Hz, 1H), 7.82 (d, J=7.8 Hz, 1H), 7.73 (s, 1H), 7.65 (m, 2H), 7.10 (m, 3H), 3.17 (m, 1H). 2.28 (s, 3H), 2.24 (s, 3H), 1.41 (s, 3H), 1.38 (s, 3H). MS (ES) m/z 471(M+H)$^+$.

Example 93

3-{N'-[3-(benzyloxymethyl)-1-(3,4-dimethylphenyl)-5-oxo-1,5-dihydropyrazol-4-ylidene]hydrazino}-2'-hydroxybiphenyl-3-carboxylic acid $^1$H NMR (300 MHz, d$_6$-DMSO) δ 13.1 (br s, 1H), 9.8 (br s, 1H), 8.15 (s, 1H), 7.97 (d, J=7.8 Hz, 1H), 7.82 (d, J=7.7 Hz, 1H), 7.56 (m, 4H), 7.40 (m, 5H), 7.18 (m, 3H), 4.69 (s, 2H), 4.64 (s, 2H), 2.28 (s, 3H), 2.26 (s, 3H). MS (ES) m/z 549(M+H)$^+$.

Example 94

3'-{N'-[3-ethyl-5-oxo-1-(4-trifluoromethylphenyl)-1,5-dihydropyrazol-4-ylidene]hydrazino}-2'-hydroxybiphenyl-3-carboxylic acid $^1$H NMR (300 MHz, d$_6$-DMSO) δ 13.6 (br s, 1H), 13.1 (br s, 1H), 9.8 (s, 1H), 8.19 (d, J=8.6 Hz, 1H), 8.14 (s, 1H), 7.98 (d, J=7.8 Hz, 1H), 7.80 (m, 3H), 7.72 (d, J=7.1 Hz, 1H), 7.63 (t, J=7.8 Hz, 1H), 7.19 (m, 2H), 2.55 (m, 2H), 1.27 (t, J=7.6 Hz, 3H).

Example 95

3'-{N'-[5-oxo-1-(4-trifluoromethylphenyl)-1,5-dihydropyrazol-4-ylidene]hydrazino}-2'-hydroxybiphenyl-3-carboxylic acid MS (ES) m/z 469 (M+H)$^+$.

Example 96

3'-{N'-[-1-(3,4-dimethylphenyl)-3-hydroxymethyl-5-oxo-1,5-dihydropyrazol-4-ylidene]hydrazino}-2'-hydroxybiphenyl-3-carboxylic acid $^1$H NMR (300 MHz, d$_6$-DMSO) δ 9.7 (s, 1H), 8.14 (s, 1H), 7.97 (d, J=7.6 Hz, 1H), 7.7 (m, 5H), 7.19 (m, 3H), 2.28 (s, 3H), 2.26 (s, 3H). MS (ES) m/z 459(M+H)$^+$.

Example 97

3-{N'-[3-benzyloxymethyl-5-oxo-1-(4-trifluoromethylphenyl)-1,5-dihydropyrazol-4-ylidene]hydrazino}-2'-hydroxybiphenyl-3-carboxylic acid $^1$H NMR (300 MHz, d$_6$-DMSO) δ 9.8 (s, 1H), 8.20 (d, J=7.6 Hz, 2H), 8.14 (s, 1H), 7.99 (d, J=7.7 Hz, 1H), 7.84 (d, J=7.2 Hz, 2H), 7.72 (d, J=7.1 Hz, 1H), 7.63 (m, 2H), 7.38 (m, 5H), 7.21 (m, 2H), 4.71 (s, 2H), 4.68 (s, 2H). MS (ES) m/z 589(M+H)$^+$.

Example 98

3'-{N'-1-(3,4-dimethylphenyl)-3-methylsulfanylmethyl-5-oxo-1,5-dihydropyrazol-4-ylidene]hydrazino}-2'-hydroxybiphenyl-3-carboxylic acid $^1$H NMR (300 MHz, d$_6$-DMSO) δ 13.7 (br s, 1H), 9.8 (s, 1H), 8.15 (s, 1H), 7.98 (d, J=7.8 Hz, 1H), 7.82 (d, J=7.8 Hz, 1H), 7.74 (m, 2H), 7.65 (m, 2H), 7.19 (m, 3H), 3.79 (s, 2H), 2.28 (s, 3H), 2.24 (s, 3H), 2.22 (s, 3H). MS (ES) m/z 489(M+H)$^+$.

Example 99

3'-{N'-1-(3,4-dimethylphenyl)-5-oxo-3-thiophen-3-yl-1,5-dihydropyrazol-4-ylidene]hydrazino}-2'-hydroxybiphenyl-3-carboxylic acid $^1$H NMR (300 MHz, d$_6$-DMSO) δ 13.9 (br s, 1H), 13.1 (br s, 1H), 9.8 (s, 1H), 8.45 (d, J=2.7 Hz, 1H), 8.16 (s, 1H), 7.97 (d, J=7.7 Hz, 1H), 7.84 (d, J=7.7 Hz, 1H), 7.67 (m, 5H), 7.19 (m, 3H), 2.27 (s, 3H), 2.24 (s, 3H).

Example 100

3'-{N'-[5-oxo-1-(4-trifluoromethylphenyl)-3-thiophen-3-yl-1,5-dihydropyrazol-4-ylidene]hydrazino}-2'-hydroxybiphenyl-3-carboxylic acid $^1$H NMR (300 MHz, d$_6$-DMSO) δ 13.9 (br s, 1H), 9.8 (s, 1H), 8.53 (d, J=2.8 Hz, 1H), 8.29 (d, J=8.5 Hz, 2H), 8.15 (s, 1H), 7.8 (m, 7H), 7.6 (t, J=7.8 Hz, 1H), 7.12 (m, 2H). MS (ES) m/z 551 (M+H)$^+$.

Example 101

3'-{N'-[5-oxo-1-(4-trifluoromethylphenyl)-3-methylsulfanylmethyl-1,5-dihydropyrazol-4-ylidene]hydrazino}-2'-hydroxybiphenyl-3-carboxylic acid $^1$H NMR (300 MHz, d$_6$-DMSO) δ 13.7 (br s, 1H), 9.8 (s, 1H), 8.19 (s, 1H), 8.15 (d, J=8.2 Hz, 2H), 7.99 (d, J=7.5 Hz, 1H), 7.84 (m, 3H), 7.8 (d, J=7.5 Hz, 1H), 7.75 (t, J=7.4 Hz, 1H), 7.22 (m, 2H), 3.9 (s, 2H), 2.23 (s, 3H). MS (ES) m/z 529 (M+H)$^+$.

Example 102

N-(3'-{N'-[1-(3,4-dimethylphenyl)-3-methyl-5-oxo-1,5-dihydro-pyrazol-4-ylidene]hydrazino}-2'-hydroxybiphenyl-3-yl)methanesulfonamide MS (ES) m/z 492 (M+H)$^+$.

Example 103

3'-[N'-(1-benzo[1,3]dioxol-5-yl-3-methyl-5-oxo-1,5-dihydropyrazol-4-ylidene)hydrazino]-2'-hydroxybiphenyl-3-carboxylic acid;

$^1$H NMR (300 MHz, d$_6$-DMSO) δ 13.9 (br s, 1H), 13.1 (br s, 1H), 9.8 (s, 1H), 8.14 (s, 1H), 7.98 (d, J=7.7 Hz, 1H), 7.80 (d, J=7.7 Hz, 1H), 7.73 (m, 1H), 7.62 (t, J=7.7 Hz, 1H), 7.47 (s, 1H), 7.39 (d, J=8.5 Hz, 1H), 7.17 (m, 2H), 7.0 (d, J=8.5 Hz, 1H), 6.07 (s, 2H), 2.33 (s, 3H). MS (ES) m/z 458 (M+H)$^+$.

Example 104

3-{N'-[1-(3,5-dimethylphenyl)-3-methyl-5-oxo-1,5-dihydropyrazol-4-ylidene]hydrazino}-2'-hydroxybiphenyl-3-carboxylic acid $^1$H NMR (300 MHz, d$_6$-DMSO) δ 13.7 (br s, 1H), 13.1 (br s, 1H), 9.7 (s, 1H), 8.14 (s, 1H), 7.97 (d, J=7.7 Hz, 1H), 7.80 (d, J=7.7 Hz, 1H), 7.72 (dd, J=1.9 Hz and 6.8 Hz, 1H), 7.62 (t, J=7.7 Hz, 1H), 7.58 (s, 2H), 7.17 (m, 2H), 7.0 (d, J=8.5 Hz, 1H), 6.87 (s, 1H), 2.33 (s, 9H).

MS (ES) m/z 443 (M+H)$^+$.

Example 105

3-{N'-[1-(3,4-dimethylphenyl)-3-methyl-5-oxo-1,5-dihydropyrazol-4-ylidene]hydrazino}-4'-hydroxybiphenyl-4-carboxylic acid MS (ES) m/z 443 (M+H)$^+$.

Example 106

3-{N'-[1-(3-chloro-4-methylphenyl)-3-methyl-5-oxo-1,5-dihydropyrazol-4-ylidene]hydrazino}-2'-hydroxybiphenyl-3-carboxylic acid $^1$H NMR (300 MHz, d$_6$-DMSO) δ 13.7 (br s, 1H), 13.1 (br s, 1H), 9.7 (s, 1H), 8.14 (s, 1H), 7.98 (s, 1H), 7.97 (d, J=7.1 Hz, 1H), 7.79 (m, 2H), 7.7 (d, J=7.1 Hz, 1H), 7.62 (t, J=7.6 Hz, 1H), 7.42 (d, J=8.5 Hz, 1H), 7.19 (m, 2H), 2.23 (s, 6H). MS (ES) m/z 463 (M+H)$^+$.

Example 107

3-{N'-[1-(3,4-dimethylphenyl)-3-methyl-5-oxo-1,5-dihydropyrazol-4-ylidene]hydrazino}-4'-hydroxybiphenyl-3-carboxylic acid MS (ES) m/z 443 (M+H).

Example 108

3-{N'-[1-(3,4-dimethylphenyl)-3-methyl-5-oxo-1,5-dihydropyrazol-4-ylidene]hydrazino}-2'-hydroxybiphenyl-3-phosphonic acid $^1$H NMR (300 MHz, DMSO-d$_6$) δ 13.8 (br s, 1H), 10.5-9.5 (br s, 1H), 7.89-7.53 (m, 7H), 7.23-7.10 (m, 3H), 2.34 (s, 3H), 2.27 (s, 3H), 2.22 (s, 3H).

Example 109

3'-{N'-[1-(3,4-dimethylphenyl)-3-methyl-5-oxo-1,5-dihydropyrazol-4-ylidene]hydrazino}-2'-hydroxybiphenyl-3,4-dicarboxylic acid Anal. (C$_{26}$H$_{22}$N$_4$O$_6$.0.75H$_2$O) calcd: C, 62.46; H, 4.74; N, 11.21. found: C, 62.63; H, 4.86; N, 10.84.

Example 110

2',6-dihydroxy-3'-{N'-[1-(3,4-dimethylphenyl)-3-methyl-5-oxo-1,5-dihydropyrazol-4-ylidene]hydrazino}biphenyl-3-carboxylic acid Anal. ($C_{25}H_{22}N_4O_5 \cdot 0.5H_2O$) calcd: C, 64.23; H, 4.96; N, 11.98. found: C, 64.37; H, 4.97; N, 11.85.

Example 111

4-aza-3'-{N'-[1-(3,4-dimethylphenyl)-3-methyl-5-oxo-1,5-dihydropyrazol-4-ylidene]hydrazino}-2'-hydroxybiphenyl-5-carboxylic acid

Example 112

3-{N'-[1-(3,4-dimethylphenyl)-3-methyl-5-oxo-1,5-dihydropyrazol-4-ylidene]hydrazino}-2'-hydroxybiphenyl-3-sulfonic acid MS (ES) m/z 479 (M+H).

Example 113

5-(3'-{N'-[1-(3,4-Dimethylphenyl)-3-methyl-5-oxo-1,5-dihydropyrazol-4-ylidene]hydrazino}-2'-hydroxybiphenyl-3-ylmethylene)thiazolidine-2,4-dione MS (ES+) m/e 526 [M+H]$^+$.

Example 114

Capsule Composition

An oral dosage form for administering a presently invented agonist of the TPO receptor is produced by filling a standard two piece hard gelatin capsule with the ingredients in the proportions shown in Table I, below.

TABLE I

| INGREDIENTS | AMOUNTS |
|---|---|
| 4'-{N'-[1-(3,4-Dimethylphenyl)-3-methyl-5-oxo-1,5-dihydropyrazol-4-ylidene]hydrazino}-3'-hydroxybiphenyl-4-carboxylic acid; (Compound of Example 1) | 25 mg |
| Lactose | 55 mg |
| Talc | 16 mg |
| Magnesium Stearate | 4 mg |

Example 115

Injectable Parenteral Composition

An injectable form for administering a presently invented agonist of the TPO receptor is produced by stirring 1.5% by weight of 4'-{N'-[1-(3,4-dimethylphenyl)-3-methyl-5-oxo-1,5-dihydropyrazol-4-ylidene]hydrazino}-3'-hydroxybiphenyl-3-carboxylic acid; (Compound of Example 2) in 10% by volume propylene glycol in water.

Example 116

Tablet Composition

The sucrose, calcium sulfate dihydrate and a presently invented agonist of the TPO receptor, as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
|---|---|
| 3'-{N'-[1-(3,4-dimethylphenyl)-3-methyl-5-oxo-1,5-dihydropyrazol-4-ylidene]hydrazino}-2'-hydroxybiphenyl-3-carboxylic acid; (Compound of Example 3) | 20 mg |
| calcium sulfate dihydrate | 30 mg |
| sucrose | 4 mg |
| starch | 2 mg |
| talc | 1 mg |
| stearic acid | 0.5 mg |

Preferred among the compounds of the present invention are the following;

3'-{N'-[3-cyclopropyl-1-(3,4-dimethylphenyl)-5-oxo-1,5-dihydropyrazol-4-ylidene]hydrazino}-2'-hydroxybiphenyl-3-carboxylic acid;

[1-(4-fluoro-3-methylphenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(4-trifluoromethylphenyl)-1,5-dihydropyrazol-4-ylidene]hydrazino}-2'-hydroxybiphenyl-3-carboxylic acid;

3'-{N'-[1-(3,4-Dimethylphenyl)-3-methyl-5-oxo-1,5-dihydropyrazol-4-ylidene]hydrazino}-2'-hydroxybiphenyl-3-carboxylic acid;

3-{N'-[1-(3,4-dimethylphenyl)-3-methyl-5-oxo-1,5-dihydropyrazol-4-ylidene]hydrazino}-2-hydroxy-3'-tetrazol-5-ylbiphenyl;

3'-{N'-[1-(3-fluoro-4-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-ethyl-5-oxo-1,5-dihydropyrazol-4-ylidene]hydrazino}-2'-hydroxybiphenyl-3-carboxylic acid;

3-{N'-[1-(3,4-dimethylphenyl)-3-ethyl-5-oxo-1,5-dihydropyrazol-4-ylidene]hydrazino}-2-hydroxy-3'-tetrazol-5-ylbiphenyl;

3'-{N'-[1-(3-chloro-4-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-methyl-5-oxo-1,5-dihydropyrazol-4-ylidene]hydrazino}-5'-fluoro-2'-hydroxybiphenyl-3-carboxylic acid;

3'-{N'-[1-(3,4-Dimethylphenyl)-3-methoxy-5-oxo-1,5-dihydropyrazol-4-ylidene]hydrazino}-2'-hydroxybiphenyl-3-carboxylic acid;

3-Aza-3'-{N'-[1-(4-tert-butylphenyl)-3-methyl-5-oxo-1,5-dihydropyrazol-4-ylidene]hydrazino}-2'-hydroxybiphenyl-5-carboxylic acid;

3'-{N'-[3-methyl-1-(4-methylphenyl)-5-oxo-1,5-dihydropyrazol-4-ylidene]hydrazino}-2'-hydroxybiphenyl-3-carboxylic acid;

[1-(4-fluoro-3-methylphenyl)-3-methyl-5-oxo-1,5-dihydropyrazol-4-ylidene]hydrazino}-2'-hydroxybiphenyl-3-carboxylic acid;

3'-{N'-[1-(3,5-dimethylphenyl)-3-methyl-5-oxo-1,5-dihydropyrazol-4-ylidene]hydrazino}-2'-hydroxybiphenyl-3-carboxylic acid;

(3-{N'-[1-(3,4-dimethylphenyl)-3-methyl-5-oxo-1,5-dihydropyrazol-4-ylidene]hydrazino}-2-hydroxy-3'-biphenyl)-1,1,1,-trifluoromethanesulfonamide; and 3'-{N'-[1-(3,4-dimethylphenyl)-5-oxo-1,5-dihydropyrazol-4-ylidene]hydrazino}-2'-hydroxybiphenyl-3-carboxylic acid.

Particularly preferred among the compounds of the invention are following;

3'-{N'-[3-cyclopropyl-1-(3,4-dimethylphenyl)-5-oxo-1,5-dihydropyrazol-4-ylidene]hydrazino}-2'-hydroxybiphenyl-3-carboxylic acid;

[1-(4-fluoro-3-methylphenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(4-trifluoromethylphenyl)-1,5-dihydropyrazol-4-ylidene]hydrazino}-2'-hydroxybiphenyl-3-carboxylic acid;

3'-{N'-[1-(3,4-Dimethylphenyl)-3-methyl-5-oxo-1,5-dihydropyrazol-4-ylidene]hydrazino}-2'-hydroxybiphenyl-3-carboxylic acid;

3-{N'-[1-(3,4-dimethylphenyl)-3-methyl-5-oxo-1,5-dihydropyrazol-4-ylidene]hydrazino}-2-hydroxy-3'-tetrazol-5-ylbiphenyl;

3'-{N'-[1-(3-fluoro-4-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-ethyl-5-oxo-1,5-dihydropyrazol-4-ylidene]hydrazino}-2'-hydroxybiphenyl-3-carboxylic acid;

{N'-[1-(3,4-dimethylphenyl)-3-ethyl-5-oxo-1,5-dihydropyrazol-4-ylidene]hydrazino}-2-hydroxy-3'-tetrazol-5-ylbiphenyl;

3'-{N'-[1-(3-chloro-4-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-methyl-5-oxo-1,5-dihydropyrazol-4-ylidene]hydrazino}-5'-fluoro-2'-hydroxybiphenyl-3-carboxylic acid;

3'-{N'-[1-(3,4-Dimethylphenyl)-3-methoxy-5-oxo-1,5-dihydropyrazol-4-ylidene]hydrazino}-2'-hydroxybiphenyl-3-carboxylic acid;

3-Aza-3'-{N'-[1-(4-tert-butylphenyl)-3-methyl-5-oxo-1,5-dihydropyrazol-4-ylidene]hydrazino}-2'-hydroxybiphenyl-5-carboxylic acid; and 3'-{N'-[3-methyl-1-(4-methylphenyl)-5-oxo-1,5-dihydropyrazol-4-ylidene]hydrazino}-2'-hydroxybiphenyl-3-carboxylic acid.

Particularly preferred among the compounds of the invention are following;

3'-{N'-[3-cyclopropyl-1-(3,4-dimethylphenyl)-5-oxo-1,5-dihydropyrazol-4-ylidene]hydrazino}-2'-hydroxybiphenyl-3-carboxylic acid;

[1-(4-fluoro-3-methylphenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(4-trifluoromethylphenyl)-1,5-dihydropyrazol-4-ylidene]hydrazino}-2'-hydroxybiphenyl-3-carboxylic acid;

3-{N'-[1-(3,4-dimethylphenyl)-3-methyl-5-oxo-1,5-dihydropyrazol-4-ylidene]hydrazino}-2-hydroxy-3'-tetrazol-5-ylbiphenyl;

3'-{N'-[1-(3,4-Dimethylphenyl)-3-methyl-5-oxo-1,5-dihydropyrazol-4-ylidene]hydrazino}-2'-hydroxybiphenyl-3-carboxylic acid;

3'-{N'-[1-(3-fluoro-4-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-ethyl-5-oxo-1,5-dihydropyrazol-4-ylidene]hydrazino}-2'-hydroxybiphenyl-3-carboxylic acid; and 3-{N'-[1-(3,4-dimethylphenyl)-3-ethyl-5-oxo-1,5-dihydropyrazol-4-ylidene]hydrazino}-2-hydroxy-3'-tetrazol-5-ylbiphenyl.

The most preferred among the compounds of the invention is, 3'-{N'-[1-(3,4-Dimethylphenyl)-3-methyl-5-oxo-1,5-dihydropyrazol-4-ylidene]hydrazino}-2'-hydroxybiphenyl-3-carboxylic acid.

The compound 3'-{N'-[1-(3,4-Dimethylphenyl)-3-methyl-5-oxo-1,5-dihydropyrazol-4-ylidene]hydrazino}-2'-hydroxybiphenyl-3-carboxylic acid demonstrated an activity of, EC50=0.03 uM, 100% TPO in the above proliferation assay.

While the preferred embodiments of the invention are illustrated by the above, it is to be understood that the invention is not limited to the precise instructions herein disclosed and that the right to all modifications coming within the scope of the following claims is reserved.

What is claimed is:

1. A method of treating thrombocytopenia in a human in need thereof which comprises administering to such human a therapeutically effective amount of a compound of Formula (I):

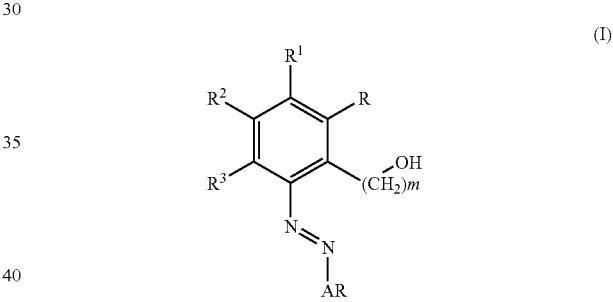

wherein:

R, $R^1$, $R^2$ and $R^3$ are each independently selected from hydrogen, $C_{1-6}$alkyl, —$(CH_2)_pOR^4$, —$C(O)OR^4$, formyl, nitro, cyano, halogen, aryl, substituted aryl, substituted alkyl, —$S(O)_nR^4$, cycloalkyl, —$NR^5R^6$, protected —OH, —$CONR^5R^6$, phosphonic acid, sulfonic acid, phosphinic acid, —$SO_2NR^5R^6$, and a heterocyclic methylene substituent as represented by Formula (III),

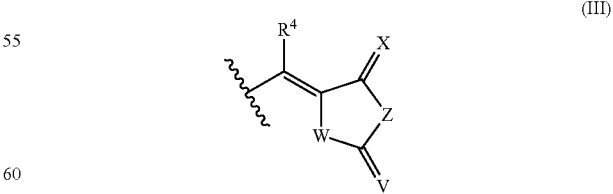

where, p is 0-6, n is 0-2,

V, W, X and Z are each independently selected from O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, $R^4$ is selected from: hydrogen, alkyl, cycloalkyl, $C_1$-$C_{12}$aryl, substituted alkyl, substituted cycloalkyl and substituted $C_1$-$C_{12}$aryl, and $R^5$ and $R^6$ are each independently selected from hydrogen, alkyl, substituted alkyl, $C_{3-6}$cycloalkyl, and aryl, or $R^5$ and $R^6$ taken together with the nitrogen to which they are attached represent a 5 to 6 member saturated ring containing up to one other heteroatom selected from oxygen and nitrogen;

m is 0-6; and

AR is a cyclic or polycyclic aromatic ring containing from 3 to 16 carbon atoms and containing from one to three heteroatoms, provided that when the number of carbon atoms is 3 the aromatic ring contains at least two heteroatoms, and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, —C(O)OR$^4$, —C(O)NR$^{10}$R$^{11}$, —S(O)$_2$NR$^{10}$R$^{11}$, —S(O)$_n$R$^4$ and protected —OH, where n is 0-2, $R^4$ is hydrogen, alkyl, cycloalkyl, $C_1$-$C_{12}$aryl, substituted alkyl, substituted cycloalkyl and substituted $C_1$-$C_{12}$aryl, and $R^{10}$ and $R^{11}$ are independently hydrogen, cycloalkyl, $C_1$-$C_{12}$aryl, substituted cycloalkyl, substituted $C_1$-$C_{12}$aryl, alkyl or alkyl substituted with one or more substituents selected from the group consisting of: alkoxy, acyloxy, aryloxy, amino, N-acylamino, oxo, hydroxy, —C(O)OR$^4$, —S(O)$_n$R$^4$, —C(O)NR$^4$R$^4$, —S(O)$_2$NR$^4$R$^4$, nitro, cyano, cycloalkyl, substituted cycloalkyl, halogen, aryl, substituted aryl and protected —OH, or $R^{10}$ and $R^{11}$ taken together with the nitrogen to which they are attached represent a 5 to 6 member saturated ring containing up to one other heteroatom selected from oxygen and nitrogen, where $R^4$ is as described above and n is 0-2;

or a pharmaceutically acceptable salt, hydrate, solvate or ester thereof;

provided that at least one of R, $R^1$, $R^2$ and $R^3$ is a substituted aryl group or a heterocyclic methylene substituent as represented in Formula (III).

2. The method to claim 1 wherein, when a single substituent is present on a substituted aryl group defined by any of R, $R^1$, $R^2$ and $R^3$, said substituent is selected from the group consisting of: —CO$_2$R$^{20}$ aryl —C(O)NHS(O)$_2$R$^{20}$— NHS(O)$_2$R, hydroxyalkyl, alkoxy, —C(O)NR$^{21}$R$^{22}$, acyloxy, amino, N-acylamino, hydroxy —(CH$_2$)$_g$C(O)OR$^8$—S(O)$_n$R$^8$, nitro, tetrazole, cyano, oxo, halogen, trifluoromethyl, protected —OH and a heterocyclic methylene substituent as represented by Formula (III),

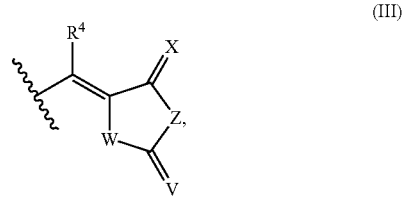

where g is 0-6; $R^8$ is hydrogen or alkyl; $R^{20}$ is selected form hydrogen, $C_1$-$C_4$alkyl, aryl and trifluoromethyl; $R^{21}$ and $R^{22}$ are independently selected from hydrogen, $C_1$-$C_4$alkyl, aryl and trifluoromethyl; V, W, X and Z are each independently selected from O, S, and NR$^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl; and n is 0-2.

3. The method of claim 1 wherein the administered compound is a compound of the Formula (II):

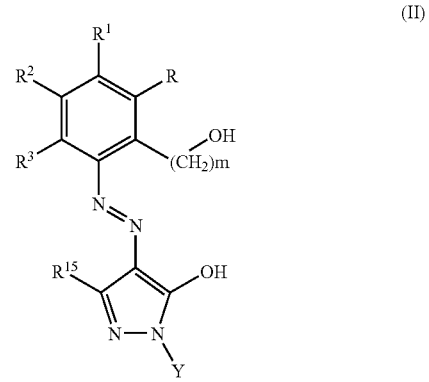

wherein:

R, $R^1$, $R^2$ and $R^3$ are each independently selected from hydrogen, $C_{1-6}$alkyl, —(CH$_2$)$_p$OR$^4$, —C(O)OR$^4$, formyl, nitro, cyano, halogen, aryl, substituted aryl, substituted alkyl, —S(O)$_n$R$^4$, cycloalkyl, —NR$^5$R$^6$, protected —OH, —CONR$^5$R$^6$, phosphonic acid, sulfonic acid, phosphinic acid, —SO$_2$NR$^5$R$^6$, and a heterocyclic methylene substituent as represented by Formula (III),

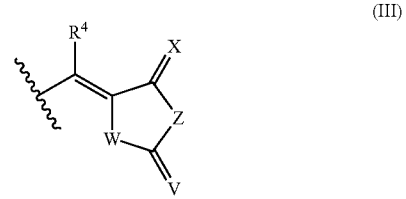

where
p is 0-6,
n is 0-2,
V, W, X and Z are each independently selected from O, S, and NR$^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, $R^4$ is hydrogen, alkyl, cycloalkyl, $C_1$-$C_{12}$aryl, substituted alkyl, substituted cycloalkyl and substituted $C_1$-$C_{12}$aryl, and $R^5$ and $R^6$ are each independently selected from hydrogen, alkyl, substituted alkyl, $C_{3-6}$cycloalkyl, and aryl, or $R^5$ and $R^6$ taken together with the nitrogen to which they are attached represent a 5 to 6 member saturated ring containing up to one other heteroatom selected from oxygen and nitrogen;

$R^{15}$ is selected from the group consisting of alkyl, $C_1$-$C_{12}$aryl, hydroxy, alkoxy, substituted alkyl, substituted $C_1$-$C_{12}$aryl and halogen;

m is 0-6; and

Y is selected from alkyl, substituted alkyl and a cyclic or polycyclic aromatic ring containing from 3 to 14 carbon atoms and optionally containing from one to three heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, $C_1$-$C_{12}$aryl, substituted cycloalkyl, substituted $C_1$-$C_{12}$aryl, hydroxy, aryloxy, alkoxy, cycloalkyl, nitro, cyano, halogen and protected —OH;

or a pharmaceutically acceptable salt, hydrate, solvate or ester thereof;

provided that at least one of R, $R^1$, $R^2$ and $R^3$ is a substituted aryl group or a heterocyclic methylene substituent as represented in Formula (III).

4. The method of claim 3 wherein, when a single substituent is present on a substituted aryl group defined by any of R, $R^1$, $R^2$ and $R^3$, said substituent is selected from the group consisting of: —$CO_2R^{20}$, aryl, —C(O)NHS(O)$_2R^{20}$, —NHS(O)$_2R^{20}$, hydroxyalkyl, alkoxy, —C(O)NR$^{21}$R$^{22}$, acyloxy, amino, N-acylamino, hydroxy, —(CH$_2$)$_g$C(O)OR$^8$, —S(O)$_n$R$^8$, nitro, tetrazole, cyano, oxo, halogen, trifluoromethyl, protected —OH and a heterocyclic methylene substituent as represented by Formula (III),

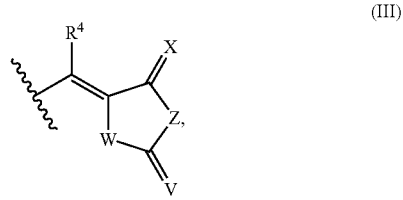

(III)

where g is 0-6; $R^8$ is hydrogen or alkyl; $R^{20}$ is selected form hydrogen, $C_1$-$C_4$alkyl, aryl and trifluoromethyl; $R^{21}$ and $R^{22}$ are independently selected from hydrogen, $C_1$-$C_4$alkyl, aryl and trifluoromethyl; V, W, X and Z are each independently selected from O, S, and NR$^{16}$, where R$^{16}$ is selected from: hydrogen, alkyl, cycloakyl, $C_1$-$C_{12}$aryl, substituted alkyl substituted cycloalkyl and substituted $C_1$-$C_{12}$aryl; and n is 0-2.

5. The method of claim 3 wherein the compound administered is a compound represented by Formula (II) wherein: either:

R is a substituted aryl; and $R^1$ is hydrogen;

or:

R is hydrogen; and $R^1$ is a substituted aryl;

and in either case:

$R^2$ and $R^3$ are each independently selected from hydrogen, $C_{1-6}$alkyl, $C_{1-6}$alkoxy, nitro, cyano, halogen, aryl, substituted aryl, substituted alkyl, cycloalkyl, phosphonic acid, phosphinic acid and sulfonic acid;

$R^{15}$ is selected from the group consisting of alkyl, substituted alkyl, $C_1$-$C_{12}$aryl, alkoxy and halogen;

m is 0-4; and

Y is selected from, phenyl, pyridinyl and pyrimidinyl, where the phenyl, pyridinyl and pyrimidinyl are optionally substituted with from one to three substituents selected from the group consisting of: alkyl, substituted alkyl, $C_1$-$C_{12}$aryl, substituted $C_1$-$C_{12}$aryl, alkoxy and halogen;

or a pharmaceutically acceptable salt, hydrate, solvate or ester thereof.

6. The method of claim 5 wherein, when a single substituent is present on a substituted aryl group defined by any of R, $R^1$, $R^2$ and $R^3$, said substituent is selected from the group consisting of: —$CO_2R^{20}$, aryl, —C(O)NHS(O)$_2R^{20}$, —NHS(O)$_2R^2$, hydroxyalkyl, alkoxy, —C(O)NR$^{21}$R$^{22}$, acyloxy, amino, N-acylamino, hydroxy —(CH$_2$)$_g$C(O)OR$^8$, —S(O)$_n$R$^8$, nitro, tetrazole, cyano, oxo, halogen, trifluoromethyl protected —OH and a heterocyclic methylene substituent as represented by Formula (III),

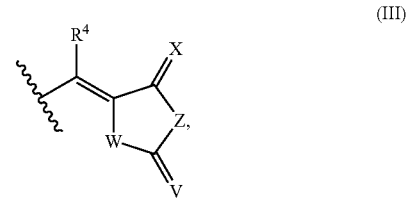

(III)

where g is 0-6; $R^8$ is hydrogen or alkyl: $R^{20}$ is selected form hydrogen, $C_1$-$C_4$alkyl, aryl and trifluoromethyl; $R^{21}$ and $R^{22}$ are independently selected from hydrogen, $C_1$-$C_4$alkyl, aryl and trifluoromethyl; V, W, X and Z are each independently selected from O, S, and NR$^{16}$, where R$^{16}$ is selected from: hydrogen, alkyl, cycloalkyl, $C_1$-$C_{12}$aryl, substituted alkyl substituted cycloalkyl and substituted $C_1$-$C_{12}$ary; and n is 0-2.

7. The method of claim 1 wherein the compound is selected from the group consisting of:

4'-{N'-[1-(3,4-Dimethylphenyl)-3-methyl-5-oxo-1,5-dihydropyrazol-4-ylidene]hydrazino}-3'-hydroxybiphenyl-3-carboxylic acid;

2-Aza-3'-{N'-[1-(4-tert-butylphenyl)-3-methyl-5-oxo-1,5-dihydropyrazol-4-ylidene]hydrazino}-5'-chloro-2'-hydroxybiphenyl-3-carboxylic acid;

2-Aza-3'-{N'-[1-(4-tert-butylphenyl)-3-methyl-5-oxo-1,5-dihydropyrazol-4-ylidene]hydrazino}-2'-hydroxybiphenyl-3-carboxylic acid;

2-Aza-5'-chloro-3'-{N'-[1-(3,4-dimethylphenyl)-3-methyl-5-oxo-1,5-dihydropyrazol-4-ylidene]hydrazino}-2'-hydroxybiphenyl-3-carboxylic acid;

2-Aza-3'-{N'-[1-(4-tert-butylphenyl)-3-methyl-5-oxo-1,5-dihydropyrazol-4-ylidene]hydrazino}-2'-hydroxy-5'-methylbiphenyl-3-carboxylic acid;

2-Aza-3'-{N'-[1-(3,4-dimethylphenyl)-3-methyl-5-oxo-1, 5-dihydropyrazol-4-ylidene]hydrazino}-2'-hydroxy-5'-methylbiphenyl-3-carboxylic acid;

3'-{N'-[1-(4-tert-Butylphenyl)-3-methyl-5-oxo-1,5-dihydropyrazol-4-ylidene]hydrazino}-2'-hydroxy-5'-methylbiphenyl-3-carboxylic acid;

3'-{N'-[1-(3,4-dimethylphenyl)-3-methyl-5-oxo-1,5-dihydropyrazol-4-ylidene]hydrazino}-5'-fluoro-2'-hydroxybiphenyl-3-carboxylic acid;

7-({N'-[1-(3,4-dimethylphenyl)-3-methyl-5-oxo-1,5-dihydropyrazol-4-ylidene]hydrazino}-2-hydroxyphenyl) quinolin-4[1H]-one-3-carboxylic acid;

7-({N'-[1-(4-tert-butylphenyl)-3-methyl-5-oxo-1,5-dihydropyrazol-4-ylidene]hydrazino}-2-hydroxyphenyl) quinolin-4[1H]-one-3-carboxylic acid;

3-Aza-3'-{N'-[1-(3,4-dimethylphenyl)-3-methyl-5-oxo-1, 5-dihydropyrazol-4-ylidene]hydrazino}-2'-hydroxybiphenyl-5-carboxylic acid;

3-Aza-3'-(N'-[1-{3-methyl-[4-(1-methylethyl)phenyl]-5-oxo-1,5-dihydropyrazol-4-ylidene}hydrazino)-2'-hydroxybiphenyl-5-carboxylic acid;

3-Aza-3'-{N'-[1-(4-tertbutylphenyl-3-methyl-5-oxo-1,5-dihydropyrazol-4-ylidene]hydrazino}-2'-hydroxybiphenyl-5-carboxylic acid;

5'-Chloro-3'-{N'-[1-(3,4-dimethylphenyl)-3-methyl-5-oxo-1,5-dihydropyrazol-4-ylidene]hydrazino}-2'-hydroxybiphenyl-3-carboxylic acid;

3'-{N'-[1-(3,4-Dimethylphenyl)-3,5-dioxo-1,5-dihydropyrazol-4-ylidene]hydrazino}-2'-hydroxybiphenyl-3-carboxylic acid;

3'-{N'-[1-(2-Ethoxy-2-oxoethyl)-3-methyl-5-oxo-1,5-dihydropyrazol-4-ylidene]hydrazino}-2'-hydroxybiphenyl-3-carboxylic acid;

3-{N'-[1-(3,4-dimethylphenyl)-3-methyl-5-oxo-1,5-dihydropyrazol-4-ylidene]hydrazino}-2-hydroxy-4'-(tetrazol-5-yl)biphenyl;

3'-(N'-{1-[2-(N-tert-butyl)amino-2-oxoethyl]-3-methyl-5-oxo-1,5-dihydropyrazol-4-ylidene} hydrazino)-2'-hydroxybiphenyl-3-carboxylic acid;

3'-{N'-[3-Chloro-1-(3,4-dimethylphenyl)-5-oxo-1,5-dihydropyrazol-4-ylidene]hydrazino}-2'-hydroxybiphenyl-3-carboxylic acid;

5-chloro-3-{N'-[1-(3,4-dimethylphenyl)-3-methyl-5-oxo-1,5-dihydropyrazol-4-ylidene]hydrazino}-2-hydroxy-4'-(tetrazol-5-yl)biphenyl;

3'-{N'-[1-(3,4-Dimethylphenyl)-3-methyl-5-oxo-1,5-dihydropyrazol-4-ylidene]hydrazino}-2'-hydroxybiphenyl-3,5-dicarboxylic acid;

3-Aza-3'-{N'-[1-(3,4-dimethylphenyl)-3-methyl-5-oxo-1, 5-dihydropyrazol-4-ylidene]hydrazino}-2'-hydroxy-5'-methylbiphenyl-5-carboxylic acid;

3'-{N'-[1-(3,4-Dimethylphenyl)-3-methyl-5-oxo-1,5-dihydropyrazol-4-ylidene]hydrazino}-2'-hydroxybiphenyl-4-carboxylic acid;

3'-{N'-[1-(3,4-Dimethylphenyl)-3-methoxy-5-oxo-1,5-dihydropyrazol-4-ylidene]hydrazino}-2'-hydroxybiphenyl-3-carboxylic acid;

3'-{N'-[1-(4-methoxyphenyl)-3-methyl-5-oxo-1,5-dihydropyrazol-4-ylidene]hydrazino}-2'-hydroxybiphenyl-3-carboxylic acid;

(3-{N'-[1-(3,4-dimethylphenyl)-3-methyl-5-oxo-1,5-dihydropyrazol-4-ylidene]hydrazino}-2-hydroxy-3'-biphenyl)-1,1,1,-trifluoromethanesulfonamide;

3'-{N'-[1-(3,4-Dichlorophenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(3-trifluoromethylphenyl)-1,5-dihydropyrazol-4-ylidene]hydrazino}-2'-hydroxybiphenyl-3-carboxylic acid;

8-{N'-[1-(3,4-dimethylphenyl)-3-methyl-5-oxo-1,5-dihydropyrazol-4-ylidene]hydrazino} quinolin-4[1H]-one-3-carboxylic acid;

3'-{N'-[3-methyl-5-oxo-1-(4-trifluoromethylphenyl)-1,5-dihydropyrazol-4-ylidene]hydrazino}-2'-hydroxybiphenyl-3-carboxylic acid;

3'-{N'-[3-methyl-5-oxo-1-(4-N-methylcarboxamidophenyl)-1,5-dihydropyrazol-4-ylidene]hydrazino}-2'-hydroxybiphenyl-3-carboxylic acid;

N-[1-(3'-{N'-[1-(3,4-dimethylphenyl)-3-methyl-5-oxo-1, 5-dihydropyrazol-4-ylidene]hydrazino}-2'-hydroxybiphenyl-3-yl)methanoyl]methanesulfonamide;

3'-{N'-[3-methyl-5-oxo-1-phenyl-1,5-dihydropyrazol-4-ylidene]hydrazino}-2'-hydroxybiphenyl-3-carboxylic acid;

3'-{N'-[3-methyl-1-(4-methylphenyl)-5-oxo-1,5-dihydropyrazol-4-ylidene]hydrazino}-2'-hydroxybiphenyl-3-carboxylic acid;

3'-{N'-[1-(4-chlorophenyl)-3-methyl-5-oxo-1,5-dihydropyrazol-4-ylidene]hydrazino}-2'-hydroxybiphenyl-3-carboxylic acid;

3'-{N'-[1-(4-fluorophenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(4-trifluoromethoxyphenyl)-1, 5-dihydropyrazol-4-ylidene]hydrazino}-2'-hydroxybiphenyl-3-carboxylic acid;

3'-{N'-[1-(3,4-dimethylphenyl)-3-ethoxy-5-oxo-1,5-dihydropyrazol-4-ylidene]hydrazino}-2'-hydroxybiphenyl-3-carboxylic acid;

3'-{N'-{1-(3,4-dimethylphenyl)-3-(1-methylethoxy)-5-oxo-1,5-dihydropyrazol-4-ylidene]hydrazino}-2'-hydroxybiphenyl-3-carboxylic acid;

3'-{N'-[3-tert-butyl-1-(3,4-dimethylphenyl)-5-oxo-1,5-dihydropyrazol-4-ylidene]hydrazino}-2'-hydroxybiphenyl-3-carboxylic acid;

3'-{N'-[3-methyl-1-(4-methyl-2,3,5,6-tetrafluorophenyl)-5-oxo-1,5-dihydropyrazol-4-ylidene]hydrazino}-2'-hydroxybiphenyl-3-carboxylic acid;

3'-{N'-[1-(4-fluoro-3-methylphenyl)-3-methyl-5-oxo-1, 5-dihydropyrazol-4-ylidene]hydrazino}-2'-hydroxybiphenyl-3-carboxylic acid;

3'-{N'-[1-(3,4-dimethylphenyl)-3-phenyl-5-oxo-1,5-dihydropyrazol-4-ylidene]hydrazino}-2'-hydroxybiphenyl-3-carboxylic acid;

3-{N'-[1-(3,4-dimethylphenyl)-5-oxo-3-phenyl-1,5-dihydropyrazol-4-ylidene]hydrazino}-2-hydroxy-3'-tetrazol-5-ylbiphenyl;

3-{N'-[1-(3,4-dimethylphenyl)-3-methoxy-5-oxo-1,5-dihydropyrazol-4-ylidene]hydrazino}-2-hydroxy-3'-tetrazol-5-ylbiphenyl;

3-{N'-[1-(3,4-dimethylphenyl)-3-ethoxy-5-oxo-1,5-dihydropyrazol-4-ylidene]hydrazino}-2-hydroxy-3'-tetrazol-5-ylbiphenyl;

3-{N'-[1-(3,4-dimethylphenyl)-3-(1-methylethoxy)-5-oxo-1,5-dihydropyrazol-4-ylidene]hydrazino}-2-hydroxy-3'-tetrazol-5-ylbiphenyl;

3-{N'-[1-(4-fluorophenyl)-3-methyl-5-oxo-1,5-dihydropyrazol-4-ylidene]hydrazino}-2-hydroxy-3'-tetrazol-5-ylbiphenyl;

3-{N'-[1-(4-fluoro-3-methylphenyl)-3-methyl-5-oxo-1,5-dihydropyrazol-4-ylidene]hydrazino}-2-hydroxy-3'-tetrazol-5-ylbiphenyl;

3-{N'-[3-methyl-5-oxo-1-(4-trifluoromethylphenyl)-1,5-dihydropyrazol-4-ylidene]hydrazino}-2-hydroxy-3'-tetrazol-5-ylbiphenyl;

3'-{N'-[1-(3,4-dimethylphenyl)-3-(pyridin-4-yl-5-oxo-1,5-dihydropyrazol-4-ylidene]hydrazino}-2'-hydroxybiphenyl-3-carboxylic acid;

3-{N'-[1-(3,4-dimethylphenyl)-3-pyridin-4-yl-5-oxo-1,5-dihydropyrazol-4-ylidene]hydrazino}-2-hydroxy-3'-tetrazol-5-ylbiphenyl;

3-{N'-[1-(3,4-dimethylphenyl)-3-pyridin-2-yl-5-oxo-1,5-dihydropyrazol-4-ylidene]hydrazino}-2-hydroxy-3'-tetrazol-5-ylbiphenyl;

3'-{N'-[1-(3,4-dimethylphenyl)-3-(pyridin-2-yl-5-oxo-1,5-dihydropyrazol-4-ylidene]hydrazino}-2'-hydroxybiphenyl-3-carboxylic acid;

3-{N'-[1-(3-fluoro-4-methylphenyl)-3-methyl-5-oxo-1,5-dihydropyrazol-4-ylidene]hydrazino}-2-hydroxy-3'-tetrazol-5-ylbiphenyl;

3'-{N'-[1-(3-fluoro-4-methylphenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(4-trifluoromethylpyrimidin-2-yl)-1,5-dihydropyrazol-4-ylidene]hydrazino}-2'-hydroxybiphenyl-3-carboxylic acid;

3'-N-tert-butoxycarbonylamino-3-{N'-[1-(3,4-Dimethylphenyl)-3-methyl-5-oxo-1,5-dihydropyrazol-4-ylidene]hydrazino}-2-hydroxybiphenyl;

3'-amino-3-{N'-[1-(3,4-dimethylphenyl)-3-methyl-5-oxo-1,5-dihydropyrazol-4-ylidene]hydrazino}-2-hydroxybiphenyl;

3-{N'-[1-(3-fluorophenyl)-3-methyl-5-oxo-1,5-dihydropyrazol-4-ylidene]hydrazino}-2-hydroxy-3'-tetrazol-5-ylbiphenyl;

3'-{N'-[1-(3-fluorophenyl)-3-methyl-5-oxo-1,5-dihydropyrazol-4-ylidene]hydrazino}-2'-hydroxybiphenyl-3-carboxylic acid;

3-{N'-[3-methyl-5-oxo-1-(2,3,4,5,6-pentafluorophenyl)-1,5-dihydropyrazol-4-ylidene]hydrazino}-2-hydroxy-3'-tetrazol-5-ylbiphenyl;

3'-{N'-[3-methyl-5-oxo-1-(2,3,4,5,6-pentafluorophenyl)-1,5-dihydropyrazol-4-ylidene]hydrazino}-2'-hydroxybiphenyl-3-carboxylic acid;

3'-{N'-[1-(3,4-difluorophenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-methoxymethyl-5-oxo-1,5-dihydropyrazol-4-ylidene]hydrazino}-2'-hydroxybiphenyl-3-carboxylic acid;

3-{N'-[1-(3,4-dimethylphenyl)-3-methoxymethyl-5-oxo-1,5-dihydropyrazol-4-ylidene]hydrazino}-2-hydroxy-3'-tetrazol-5-ylbiphenyl;

3-{N'-[1-(3,4-difluorophenyl)-3-methyl-5-oxo-1,5-dihydropyrazol-4-ylidene]hydrazino}-2-hydroxy-3'-tetrazol-5-ylbiphenyl;

3'-{N'-[1-(3,4-dimethylphenyl)-5-oxo-3-trifluoromethyl-1,5-dihydropyrazol-4-ylidene]hydrazino}-2'-hydroxybiphenyl-3-carboxylic acid;

3'-{N'-[1-(3,4-dimethylphenyl)-3-methyl-5-oxo-1,5-dihydropyrazol-4-ylidene]hydrazino}-6-fluoro-2'-hydroxybiphenyl-3-carboxylic acid;

3'-{N'-[1-(3,4-dimethylphenyl)-5-oxo-3-propyl-1,5-dihydropyrazol-4-ylidene]hydrazino}-2'-hydroxybiphenyl-3-carboxylic acid;

3-{N'-[1-(3,4-dimethylphenyl)-5-oxo-3-propyl-1,5-dihydropyrazol-4-ylidene]hydrazino}-2-hydroxy-3'-tetrazol-5-ylbiphenyl;

3'-{N'-[1-(3,4-dimethylphenyl)-3-(1-methyl 1 H-pyrrol-3-yl)-5-oxo-1,5-dihydropyrazol-4-ylidene]hydrazino}-2'-hydroxybiphenyl-3-carboxylic acid;

3-{N'-[1-(3,4-dimethylphenyl)-3-(1-methyl-1H-pyrrol-3-yl)-5-oxo-1,5-dihydropyrazol-4-ylidene]hydrazino}-2-hydroxy-3'-tetrazol-5-ylbiphenyl;

3'-{N'-[1-(3,4-dimethylphenyl)-3-furan-2-yl-5-oxo-1,5-dihydropyrazol-4-ylidene]hydrazino}-2'-hydroxybiphenyl-3-carboxylic acid;

3-{N'-[1-(3,4-dimethylphenyl)-3-furan-2-yl-5-oxo-1,5-dihydropyrazol-4-ylidene]hydrazino}-2-hydroxy-3'-tetrazol-5-ylbiphenyl;

N-(2'-hydroxy-3'-{N'-[3-methyl-5-oxo-1-(4-trifluoromethyl-phenyl)-1,5-dihydro-pyrazol-4-ylidene]hydrazino}biphenyl-3-yl)-1,1,1-trifluoromethanesulfonamide;

N-(2'-hydroxy-3'-{N'-[1-(3-fluoro-4-methylphenyl)-3-methyl-5-oxo-1,5-dihydro-pyrazol-4-ylidene]hydrazino}biphenyl-3-yl)-1,1,1-trifluoromethanesulfonamide;

N-(2'-hydroxy-3'-{N'-[1-(4-fluoro-3-methylphenyl)-3-methyl-5-oxo-1,5-dihydro-pyrazol-4-ylidene]hydrazino} biphenyl-3-yl)-1,1,1-trifluoromethanesulfonamide;

N-(2'-hydroxy-3'-{N'-[1-(3,4-difluorophenyl)-3-methyl-5-oxo-1,5-dihydro-pyrazol-4-ylidene]hydrazino} biphenyl-3-yl)-1,1,1-trifluoromethanesulfonamide;

N-(3-{N'-[1-(3,4-dimethylphenyl)-3-methyl-5-oxo-1,5-dihydropyrazol-4-ylidene]hydrazino}-2'-hydroxybiphenyl-3-yl)guanidine;

3'-{N'-[1-(3,4-dimethylphenyl)-3-ethyl-5-oxo-1,5-dihydropyrazol-4-ylidene]hydrazino}-2'-hydroxybiphenyl-3-carboxylic acid;

3-{N'-[1-(3,4-dimethylphenyl)-3-ethyl-5-oxo-1,5-dihydropyrazol-4-ylidene]hydrazino}-2-hydroxy-3'-tetrazol-5-ylbiphenyl;

3'-{N'-[1-(3,4-dimethylphenyl)-5-oxo-3-thien-2-yl-1,5-dihydropyrazol-4-ylidene]hydrazino}-2'-hydroxybiphenyl-3-carboxylic acid;

3'-{N'-[3-cyclopropyl-1-(3,4-dimethylphenyl)-5-oxo-1,5-dihydropyrazol-4-ylidene]hydrazino}-2'-hydroxybiphenyl-3-carboxylic acid;

3'-{N'-[1-(3,4-dimethylphenyl)-5-oxo-3-thiazol-2-yl-1,5-dihydropyrazol-4-ylidene]hydrazino}-2'-hydroxybiphenyl-3-carboxylic acid;

3'-{N'-[1-(3,4-dimethylphenyl)-5-oxo-1,5-dihydropyrazol-4-ylidene]hydrazino}-2'-hydroxybiphenyl-3-carboxylic acid;

3'-{N'-[1-(3,4-dimethylphenyl)-3-(1-methylethyl)-5-oxo-1,5-dihydropyrazol-4-ylidene]hydrazino}-2'-hydroxybiphenyl-3-carboxylic acid;

3'-{N'-[3-(benzyloxymethyl)-1-(3,4-dimethylphenyl)-5-oxo-1,5-dihydropyrazol-4-ylidene]hydrazino}-2'-hydroxybiphenyl-3-carboxylic acid;

3'-{N'-[3-ethyl-5-oxo-1-(4-trifluoromethylphenyl)-1,5-dihydropyrazol-4-ylidene]hydrazino}-2'-hydroxybiphenyl-3-carboxylic acid;

3'-{N'-[5-oxo-1-(4-trifluoromethylphenyl)-1,5-dihydropyrazol-4-ylidene]hydrazino}-2'-hydroxybiphenyl-3-carboxylic acid;

3'-{N'-[-1-(3,4-dimethylphenyl)-3-hydroxymethyl-5-oxo-1,5-dihydropyrazol-4-ylidene]hydrazino}-2'-hydroxybiphenyl-3-carboxylic acid;

3'-{N'-[3-benzyloxymethyl-5-oxo-1-(4-trifluoromethylphenyl)-1,5-dihydropyrazol-4-ylidene]hydrazino}-2'-hydroxybiphenyl-3-carboxylic acid;

3'-{N'-[-1-(3,4-dimethylphenyl)-3-methylsulfanylm-
ethyl-5-oxo-1,5-dihydropyrazol-4-ylidene]hydrazino}-
2'-hydroxybiphenyl-3-carboxylic acid;

3'-{N'-[-1-(3,4-dimethylphenyl)-5-oxo-3-thiophen-3-yl-
1,5-dihydropyrazol-4-ylidene]hydrazino}-2'-hydroxy-
biphenyl-3-carboxylic acid;

3'-{N'-[5-oxo-1-(4-trifluoromethylphenyl)-3-thiophen-3-
yl-1,5-dihydropyrazol-4-ylidene]hydrazino}-2'-hy-
droxybiphenyl-3-carboxylic acid;

3'-{N'-[5-oxo-1-(4-trifluoromethylphenyl)-3-methylsul-
fanylmethyl-1,5-dihydropyrazol-4-ylidene]hy-
drazino}-2'-hydroxybiphenyl-3-carboxylic acid;

N-(3'-{N'-[1-(3,4-dimethylphenyl)-3-methyl-5-oxo-1,5-
dihydro-pyrazol-4-ylidene]hydrazino}-2'-hydroxybi-
phenyl-3-yl)methanesulfonamide;

3'-[N'-(1-benzo[1,3]dioxol-5-yl-3-methyl-5-oxo-1,5-di-
hydropyrazol-4-ylidene)hydrazino]-2'-hydroxybiphe-
nyl-3-carboxylic acid;

3'-{N'-[1-(3,5-dimethylphenyl)-3-methyl-5-oxo-1,5-di-
hydropyrazol-4-ylidene]hydrazino}-2'-hydroxybiphe-
nyl-3-carboxylic acid;

3'-{N'-[1-(3,4-dimethylphenyl)-3-methyl-5-oxo-1,5-di-
hydropyrazol-4-ylidene]hydrazino}-4'-hydroxybiphe-
nyl-4-carboxylic acid;

3'-{N'-[1-(3-chloro-4-methylphenyl)-3-methyl-5-oxo-1,
5-dihydropyrazol-4-ylidene]hydrazino}-2'-hydroxybi-
phenyl-3-carboxylic acid;

3'-{N'-[1-(3,4-dimethylphenyl)-3-methyl-5-oxo-1,5-di-
hydropyrazol-4-ylidene]hydrazino}-4'-hydroxybiphe-
nyl-3-carboxylic acid;

3'-{N'-[1-(3,4-dimethylphenyl)-3-methyl-5-oxo-1,5-di-
hydropyrazol-4-ylidene]hydrazino}-2'-hydroxybiphe-
nyl-3-phosphonic acid;

3'-{N'-[1-(3,4-dimethylphenyl)-3-methyl-5-oxo-1,5-di-
hydropyrazol-4-ylidene]hydrazino}-2'-hydroxybiphe-
nyl-3,4-dicarboxylic acid;

2',6-dihydroxy-3'-{N'-[1-(3,4-dimethylphenyl)-3-methyl-
5-oxo-1,5-dihydropyrazol-4-ylidene]
hydrazino}biphenyl-3-carboxylic acid;

4-aza-3'-{N'-[1-(3,4-dimethylphenyl)-3-methyl-5-oxo-1,
5-dihydropyrazol-4-ylidene]hydrazino}-2'-hydroxybi-
phenyl-5-carboxylic acid;

3'-{N'-[1-(3,4-dimethylphenyl)-3-methyl-5-oxo-1,5-di-
hydropyrazol-4-ylidene]hydrazino}-2'-hydroxybiphe-
nyl-3-sulfonic acid; and 5-(3'-{N'-[1-(3,4-Dimethylphenyl)-3-methyl-5-oxo-1,5-
dihydropyrazol-4-ylidene]hydrazino}-2'-hydroxybi-
phenyl-3-ylmethylene)thiazolidine-2,4-dione;

and or a pharmaceutically acceptable salt, hydrate, solvaten or esterthereof.

8. The method of claim 1 wherein the compound is administered orally.

9. The method of claim 1 wherein the compound is administered parenterally.

10. A method of claim 1 further comprising co-administering a therapeutically effective amount of an agent selected from the group consisting of: a colony stimulating factor, cytokine, chemokine, and an interleukin or cytokine receptor agonist or antagonists.

11. The method of claim 10 wherein the agent is selected from the group consisting of: G-CSF, GM-CSF, TPO, M-CSF, EPO, Gro-beta, IL-11, SCF, FLT3 ligand, LIF, IL-3, IL-6, IL-1, NESP, SD-01, IL-8, and IL-5.

12. A method of claim 1 wherein said thrombocytopenia is due to myelosuppression caused by chemotherapy or radiation therapy.

13. A method of claim 1 wherein said thrombocytopenia is due to an organ transplant.

14. A method of claim 1 wherein said thrombocytopenia is due to bone marrow, stem cell, or liver transplant.

15. A method of claim 1 wherein said thrombocytopenia is due to idiopathic thrombocytopenia purpura (ITP).

16. A method of claim 1 wherein said thrombocytopenia is due to myelodysplastic syndromes (MDS), aplastic anemia or leukemia.

17. A method of claim 1 wherein said thrombocytopenia is due to viral, fungal, microbial or parasitic infection.

18. A method of claim 1 wherein said thrombocytopenia is due to liver dysfunction.

19. A method of claim 1 wherein said thrombocytopenia is due to surgical procedures.

20. A method of claim 1 wherein said thrombocytopenia is due to treatment with antiviral or antibiotic agents.

21. A method of treating thrombocytopenia in a human in need thereof which comprises administering to such human a therapeutically effective amount of a compound selected from:

4'-{N'-[1-(3,4-Dimethylphenyl)-3-methyl-5-oxo-1,5-di-
hydropyrazol-4-ylidene]hydrazino}-3'-hydroxybiphe-
nyl-3-carboxylic acid;

2-Aza-3'-{N'-[1-(4-tert-butylphenyl)-3-methyl-5-oxo-1,
5-dihydropyrazol-4-ylidene]hydrazino}-5'-chloro-2'-
hydroxybiphenyl-3-carboxylic acid;

2-Aza-3'-{N'-[1-(4-tert-butylphenyl)-3-methyl-5-oxo-1,
5-dihydropyrazol-4-ylidene]hydrazino}-2'-hydroxybi-
phenyl-3-carboxylic acid;

2-Aza-5'-chloro-3'-{N'-[1-(3,4-dimethylphenyl)-3-me-
thyl-5-oxo-1,5-dihydropyrazol-4-ylidene]hydrazino}-
2'-hydroxybiphenyl-3-carboxylic acid;

2-Aza-3'-{N'-[1-(4-tert-butylphenyl)-3-methyl-5-oxo-1,
5-dihydropyrazol-4-ylidene]hydrazino}-2'-hydroxy-5'-
methylbiphenyl-3-carboxylic acid;

2-Aza-3'-{N'-[1-(3,4-dimethylphenyl)-3-methyl-5-oxo-1,
5-dihydropyrazol-4-ylidene]hydrazino}-2'-hydroxy-5'-
methylbiphenyl-3-carboxylic acid;

3'-{N'-[1-(4-tert-Butylphenyl)-3-methyl-5-oxo-1,5-dihy-
dropyrazol-4-ylidene]hydrazino}-2'-hydroxy-5'-meth-
ylbiphenyl-3-carboxylic acid;

3-{N'-[1-(3,4-dimethylphenyl)-3-methyl-5-oxo-1,5-dihy-
dropyrazol-4-ylidene]hydrazino}-5'-fluoro-2'-hy-
droxybiphenyl-3-carboxylic acid;

7-({N'-[1-(3,4-dimethylphenyl)-3-methyl-5-oxo-1,5-di-
hydropyrazol-4-ylidene]hydrazino}-2-hydroxyphenyl)
quinolin-4[1H]-one-3-carboxylic acid;

7-({N'-[1-(4-tert-butylphenyl)-3-methyl-5-oxo-1,5-dihy-
dropyrazol-4-ylidene]hydrazino}-2-hydroxyphenyl)
quinolin-4[1H]-one-3-carboxylic acid;

3-Aza-3'-{N'-[1-(3,4-dimethylphenyl)-3-methyl-5-oxo-1,
5-dihydropyrazol-4-ylidene]hydrazino}-2'-hydroxybi-
phenyl-5-carboxylic acid;

3-Aza-3'-(N'-[1-{3-methyl-[4-(1-methylethyl)phenyl]-5-
oxo-1,5-dihydropyrazol-4-ylidene}hydrazino)-2'-hy-
droxybiphenyl-5-carboxylic acid;

3-Aza-3'-{N'-[1-(4-tertbutylphenyl-3-methyl-5-oxo-1,5-
dihydropyrazol-4-ylidene]hydrazino}-2'-hydroxybi-
phenyl-5-carboxylic acid;

5'-Chloro-3'-{N'-{[1-(3,4-dimethylphenyl)-3-methyl-5-
oxo-1,5-dihydropyrazol-4-ylidene]hydrazino}-2'-hy-
droxybiphenyl-3-carboxylic acid;

3'-{N'-[1-(3,4-Dimethylphenyl)-3,5-dioxo-1,5-dihydro-
pyrazol-4-ylidene]hydrazino}-2'-hydroxybiphenyl-3-
carboxylic acid;

3'-{N'-[1-(2-Ethoxy-2-oxoethyl)-3-methyl-5-oxo-1,5-dihydropyrazol-4-ylidene]hydrazino}-2'-hydroxybiphenyl-3-carboxylic acid;

3-{N'-[1-(3,4-dimethylphenyl)-3-methyl-5-oxo-1,5-dihydropyrazol-4-ylidene]hydrazino}-2-hydroxy-4'-(tetrazol-5-yl)biphenyl;

3'-{N'-1-[2-(N-tert-butyl)amino-2-oxoethyl]-3-methyl-5-oxo-1,5-dihydropyrazol-4-ylidene]hydrazino}-2'-hydroxybiphenyl-3-carboxylic acid: and 3'-{N'-[3-Chloro-1-(3,4-dimethylphenyl)-5-oxo-1,5-dihydropyrazol-4-ylidene]hydrazino}-2'-hydroxybiphenyl-3-carboxylic acid;

or a pharmaceutically acceptable salt, hydrate, solvate or ester thereof.

22. The method of claim 1 wherein R is a phenyl substituted with —$(CH_2)_gC(O)OR^8$, where —$(CH_2)_g$ represents a linear or branched, saturated or unsaturated hydrocarbon chain containing 0 to 6 carbons and $R^8$ is hydrogen or alkyl.

23. A method of treating thrombocytopenia in a human in need thereof which comprises administering to such human a therapeutically effective amount of a compound of Formula (V):

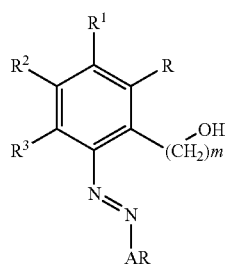

(V)

wherein:
R, $R^1$, $R^2$ and $R^3$ are each independently selected from hydrogen, $C_{1-6}$alkyl, $C_{1-6}$alkoxy, —$(CH_2)_pOR^4$, —$C(O)OR^4$, formyl, nitro, cyano, halogen, aryl, substituted aryl, substituted alkyl, —$S(O)_nR^4$, cycloalkyl, —$NR^5R^6$, protected —OH, —$CONR^5R^6$, phosphonic acid, sulfonic acid, phosphinic acid and —$SO_2NR^5R^6$, where,
p is 0-6,
n is 0-2,
$R^4$ is selected from: hydrogen, alkyl, cycloalkyl, $C_1$-$C_{12}$aryl, substituted alkyl, substituted cycloalkyl and substituted $C_1$-$C_{12}$aryl, and
$R^5$ and $R^6$ are each independently selected from hydrogen, alkyl, substituted alkyl, $C_{3-6}$cycloalkyl, and aryl,
or $R^5$ and $R^6$ taken together with the nitrogen to which they are attached represent a 5 to 6 member saturated ring containing up to one other heteroatom selected from oxygen and nitrogen;
m is 0-6; and
AR is a cyclic or polycyclic aromatic ring containing from 3 to 16 carbon atoms and containing one or more heteroatoms, provided that when the number of carbon atoms is 3 the aromatic ring contains at least two heteroatoms, and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, —$C(O)OR^4$, —$C(O)NR^{10}R^{11}$, —$S(O)_2NR^{10}R^{11}$, —$S(O)_nR^4$ and protected —OH,
where n is 0-2,
$R^4$ is hydrogen, alkyl, cycloalkyl, $C_1$-$C_{12}$aryl, substituted alkyl, substituted cycloalkyl and substituted $C_1$-$C_{12}$aryl; and
$R^{10}$ and $R^{11}$ are independently hydrogen, cycloalkyl, $C_1$-$C_{12}$aryl, substituted cycloalkyl, substituted $C_1$-$C_{12}$aryl, alkyl or alkyl substituted with one or more substituents selected from the group consisting of: alkoxy, acyloxy, aryloxy, amino, N-acylamino, oxo, hydroxy, —$C(O)OR^4$, —$S(O)_nR^4$, —$C(O)NR^4R^4$, —$S(O)_2NR^4R^4$, nitro, cyano, cycloalkyl, substituted cycloalkyl, halogen, aryl, substituted aryl and protected —OH,
or $R^{10}$ and $R^{11}$ taken together with the nitrogen to which they are attached represent a 5 to 6 member saturated ring containing up to one other heteroatom selected from oxygen and nitrogen,
where $R^4$ is as described above and n is 0-2;
or a pharmaceutically acceptable salt, hydrate, solvate or ester thereof;
provided that at least one of R, $R^1$, $R^2$ and $R^3$ is a substituted aryl group.

24. The method to claim 23 wherein, when a single substituent is present on a substituted aryl group defined by any of R, $R^1$, $R^2$ and $R^3$, said substituent is selected from the group consisting of: —$CO_2R^{20}$, aryl, —$C(O)NHS(O)_2R^{20}$, —$NHS(O)_2R^{20}$, hydroxyalkyl, alkoxy, —$C(O)NR^{21}R^{22}$, acyloxy, amino, N-acylamino, hydroxy, —$(CH_2)_gC(O)OR^8$, —$S(O)_nR^8$, nitro, tetrazole, cyano, oxo, halogen, trifluoromethyl and protected —OH, where g is 0-6, $R^8$ is hydrogen or alkyl, $R^{20}$ is selected form hydrogen, $C_1$-$C_4$alkyl, aryl and trifluoromethyl, and $R^{21}$ and $R^{22}$ are independently selected form hydrogen, $C_1$-$C_4$alkyl, aryl and trifluoromethyl, and n is 0-2.

25. The method of claim 23 wherein R is a phenyl substituted with —$(CH_2)_gC(O)OR^8$, where —$(CH_2)_g$ represents a linear or branched, saturated or unsaturated hydrocarbon chain containing 0 to 6 carbons and $R^8$ is hydrogen or alkyl.

26. The method of claim 1 wherein the compound is selected from:
5-chloro-3-{N'-[1-(3,4-dimethylphenyl)-3-methyl-5-oxo-1,5-dihydropyrazol-4-ylidene]hydrazino}-2-hydroxy-4'-(tetrazol-5-yl)biphenyl;

3'-{N'-[1-(3,4-Dimethylphenyl)-3-methyl-5-oxo-1,5-dihydropyrazol-4-ylidene]hydrazino}-2'-hydroxybiphenyl-3,5-dicarboxylic acid;

3-Aza-3'-{N'-[1-(3,4-dimethylphenyl)-3-methyl-5-oxo-1,5-dihydropyrazol-4-ylidene]hydrazino}-2'-hydroxy-5'-methylbiphenyl-5-carboxylic acid;

3'-{N'-[1-(3,4-Dimethylphenyl)-3-methyl-5-oxo-1,5-dihydropyrazol-4-ylidene]hydrazino}-2'-hydroxybiphenyl-4-carboxylic acid;

3'-{N'-[1-(3,4-Dimethylphenyl)-3-methoxy-5-oxo-1,5-dihydropyrazol-4-ylidene]hydrazino}-2'-hydroxybiphenyl-3-carboxylic acid;

3'-{N'-[1-(4-methoxyphenyl)-3-methyl-5-oxo-1,5-dihydropyrazol-4-ylidene]hydrazino}-2'-hydroxybiphenyl-3-carboxylic acid;

3-{N'-[1-(3,4-Dimethylphenyl)-3-methyl-5-oxo-1,5-dihydropyrazol-4-ylidene]hydrazino}-2-hydroxy-3'-trifluoromethanesulfonamidobiphenyl;

3'-{N'-[1-(3,4-Dichlorophenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(3-trifluoromethylphenyl)-1,5-dihydropyrazol-4-ylidene]hydrazino}-2'-hydroxybiphenyl-3-carboxylic acid;

8-{N'-[1-(3,4-dimethylphenyl)-3-methyl-5-oxo-1,5-dihydropyrazol-4-ylidene]hydrazino} quinolin-4[1H]-one-3-carboxylic acid;

3'-{N'-[3-methyl-5-oxo-1-(4-trifluoromethylphenyl)-1,5-dihydropyrazol-4-ylidene]hydrazino}-2'-hydroxybiphenyl-3-carboxylic acid;

3'-{N'-[3-methyl-5-oxo-1-(4-N-methylcarboxamidophenyl)-1,5-dihydropyrazol-4-ylidene]hydrazino}-2'-hydroxybiphenyl-3-carboxylic acid;

N-[1-(3'-{N'-[1-(3,4-dimethylphenyl)-3-methyl-5-oxo-1,5-dihydropyrazol-4-ylidene]hydrazino}-2'-hydroxybiphenyl-3-yl)methanoyl]methanesulfonamide;

3'-{N'-[3-methyl-5-oxo-1-phenyl-1,5-dihydropyrazol-4-ylidene]hydrazino}-2'-hydroxybiphenyl-3-carboxylic acid;

3'-{N'-[3-methyl-1-(4-methylphenyl)-5-oxo-1,5-dihydropyrazol-4-ylidene]hydrazino}-2'-hydroxybiphenyl-3-carboxylic acid;

3'-{N'-[1-(4-chlorophenyl)-3-methyl-5-oxo-1,5-dihydropyrazol-4-ylidene]hydrazino}-2'-hydroxybiphenyl-3-carboxylic acid;

3'-{N'-[1-(4-fluorophenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(4-trifluoromethoxyphenyl)-1,5-dihydropyrazol-4-ylidene]hydrazino}-2'-hydroxybiphenyl-3-carboxylic acid;

3'-{N'-[1-(3,4-dimethylphenyl)-3-ethoxy-5-oxo-1,5-dihydropyrazol-4-ylidene]hydrazino}-2'-hydroxybiphenyl-3-carboxylic acid;

3'-{N'-[1-(3,4-dimethylphenyl)-3-(1-methylethoxy)-5-oxo-1,5-dihydropyrazol-4-ylidene]hydrazino}-2'-hydroxybiphenyl-3-carboxylic acid;

3'-{N'-[3-tert-butyl-1-(3,4-dimethylphenyl)-5-oxo-1,5-dihydropyrazol-4-ylidene]hydrazino}-2'-hydroxybiphenyl-3-carboxylic acid;

3'-{N'-[3-methyl-1-(4-methyl-2,3,5,6-tetrafluorophenyl)-5-oxo-1,5-dihydropyrazol-4-ylidene]hydrazino}-2'-hydroxybiphenyl-3-carboxylic acid;

3'-{N'-[1-(4-fluoro-3-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-phenyl-5-oxo-1,5-dihydropyrazol-4-ylidene]hydrazino}-2'-hydroxybiphenyl-3-carboxylic acid;

3-{N'-[1-(3,4-dimethylphenyl)-5-oxo-3-phenyl-1,5-dihydropyrazol-4-ylidene]hydrazino}-2-hydroxy-3'-tetrazol-5-ylbiphenyl;

3-{N'-[1-(3,4-dimethylphenyl)-3-methoxy-5-oxo-1,5-dihydropyrazol-4-ylidene]hydrazino}-2-hydroxy-3'-tetrazol-5-ylbiphenyl;

3-{N'-[1-(3,4-dimethylphenyl)-3-ethoxy-5-oxo-1,5-dihydropyrazol-4-ylidene]hydrazino}-2-hydroxy-3'-tetrazol-5-ylbiphenyl;

3-{N'-[1-(3,4-dimethylphenyl)-3-(1-methylethoxy)-5-oxo-1,5-dihydropyrazol-4-ylidene]hydrazino}-2-hydroxy-3'-tetrazol-5-ylbiphenyl;

3-{N'-[1-(4-fluorophenyl)-3-methyl-5-oxo-1,5-dihydropyrazol-4-ylidene]hydrazino}-2-hydroxy-3'-tetrazol-5-ylbiphenyl;

3-{N'-[1-(4-fluoro-3-methylphenyl)-3-methyl-5-oxo-1,5-dihydropyrazol-4-ylidene]hydrazino}-2-hydroxy-3'-tetrazol-5-ylbiphenyl;

3-{N'-[3-methyl-5-oxo-1-(4-trifluoromethylphenyl)-1,5-dihydropyrazol-4-ylidene]hydrazino}-2-hydroxy-3'-tetrazol-5-ylbiphenyl;

3'-{N'-[1-(3,4-dimethylphenyl)-3-(pyridin-4-yl-5-oxo-1,5-dihydropyrazol-4-ylidene]hydrazino}-2'-hydroxybiphenyl-3-carboxylic acid;

3-{N'-[1-(3,4-dimethylphenyl)-3-pyridin-4-yl-5-oxo-1,5-dihydropyrazol-4-ylidene]hydrazino}-2-hydroxy-3'-tetrazol-5-ylbiphenyl;

3-{N'-[1-(3,4-dimethylphenyl)-3-pyridin-2-yl-5-oxo-1,5-dihydropyrazol-4-ylidene]hydrazino}-2-hydroxy-3'-tetrazol-5-ylbiphenyl;

3'-{N'-[1-(3,4-dimethylphenyl)-3-(pyridin-2-yl-5-oxo-1,5-dihydropyrazol-4-ylidene]hydrazino}-2'-hydroxybiphenyl-3-carboxylic acid;

3-{N'-[1-(3-fluoro-4-methylphenyl)-3-methyl-5-oxo-1,5-dihydropyrazol-4-ylidene]hydrazino}-2-hydroxy-3'-tetrazol-5-ylbiphenyl;

3'-{N'-[1-(3-fluoro-4-methylphenyl)-3-methyl-5-oxo-1,5-dihydropyrazol-4-ylidene]hydrazino}-2'-hydroxybiphenyl-3-carboxylic acid; and 3'-{N'-[3-methyl-5-oxo-1-(4-trifluoromethylpyrimidin-2-yl)-1,5-dihydropyrazol-4-ylidene]hydrazino}-2'-hydroxybiphenyl-3-carboxylic acid;

or a pharmaceutically acceptable salt, hydrate, solvate or ester thereof.

* * * * *